(12) United States Patent
Wang et al.

(10) Patent No.: US 8,227,662 B2
(45) Date of Patent: Jul. 24, 2012

(54) MARKERS FOR APHID RESISTANT GERMPLASM IN SOYBEAN PLANTS

(75) Inventors: Dechun Wang, Okemos, MI (US); Clarice Mensah, Ankeny, IA (US); Christina DiFonzo, Williamston, MI (US); Guorong Zhang, East Lansing, MI (US); Menghan Liu, Okemos, MI (US); Zhenyu Yang, Okemos, MI (US)

(73) Assignee: Board Of Trustees Of Michigan State University, East Lansing, MI (US)

( * ) Notice: Subject to any disclaimer, the term of this patent is extended or adjusted under 35 U.S.C. 154(b) by 616 days.

(21) Appl. No.: 12/261,951

(22) Filed: Oct. 30, 2008

(65) Prior Publication Data

US 2009/0241214 A1  Sep. 24, 2009

(51) Int. Cl.
*A01H 1/00* (2006.01)
*A01H 1/02* (2006.01)
*C12Q 1/68* (2006.01)
*C12N 5/04* (2006.01)

(52) U.S. Cl. ........ 800/265; 800/302; 800/279; 800/298; 435/415; 435/419

(58) Field of Classification Search ........................ None
See application file for complete search history.

(56) References Cited

U.S. PATENT DOCUMENTS

2006/0015964 A1 * 1/2006 Hill et al. ..................... 800/279

OTHER PUBLICATIONS

Narvel et al (Crop Science 41:1931-1939 (2001).*

* cited by examiner

Primary Examiner — Medina A Ibrahim
(74) Attorney, Agent, or Firm — Medlen & Carroll, LLP

(57) ABSTRACT

The present invention relates to compositions and methods for providing and using markers of aphid resistant germplasm, particularly for identifying aphid resistance germplasm in soybean plants. Specifically, the inventions related to providing aphid resistant germplasm identified by markers associated with decreased damage from aphid feeding, as well as enhanced tolerance to aphid infestation of soybean plants. More particularly, the invention relates to compositions and methods for using genetic markers in breeding methods for producing plants with increased resistance to aphid damage and tolerance, while retaining and acquiring desired agronomic traits, Furthermore, the invention relates to plants produced by these breeding programs for use in commercial soybean production.

12 Claims, 22 Drawing Sheets

(9 of 22 Drawing Sheet(s) Filed in Color)

Soybean aphid resistance in progeny of elite cultivars.

| Population | Cross | Generation | No. of Individuals | Week 3 No. of Resistant | Week 3 No. of susceptible | Week 4 No. of Resistant | Week 4 No. of susceptible |
|---|---|---|---|---|---|---|---|
| 020137 | PI567598B x PI567543C | F2 | 68 | 68 | 0 | 68 | 0 |
| 020138-1 | PI567598B x PI567541B | F2 | 311 | 311 | 0 | 311 | 0 |
| 020138-2 | PI567598B x PI567541B | F2 | 160 | 160 | 0 | 160 | 0 |
| 020138-3 | PI567598B x PI567541B | F2 | 183 | 183 | 0 | 183 | 0 |
| 020138-4 | PI567598B x PI567541B | F2 | 167 | 167 | 0 | 157 | 10 |
| 020139-1 | PI567543C x Loda | F2 | 42 | 42 | 0 | 37 | 5 |
| 020139-2 | PI567543C x Loda | F2 | 274 | 122 | 155 | 25 | 239 |
| 020142-1 | PI567597C x Titan | F2 | 22 | 15 | 7 | 7 | 15 |
| 020142-2 | PI567597C x Titan | F2 | 59 | 43 | 16 | 2 | 57 |
| 020143-1 | PI567543C x Titan | F2 | 67 | 42 | 25 | 0 | 67 |
| 030042 | E99034 x PI567598B | F1 | 3 | 3 | 0 | 3 | 0 |
| 030100 | PI567598B x PI567597C | F1 | 3 | 3 | 0 | 3 | 0 |
| 030104 | Titan x PI567598B | F1 | 7 | 7 | 0 | 7 | 0 |

Note: this data were obtained in 2004 in a choice test in a field cage. The test procedure was described in: Note: this data were obtained in 2004 in a choice test in a field cage. The test procedure was described in: Mensah, et al., 2005, Resistance to soybean aphid in early maturing soybean germplasm. Crop Sci. 45:2228-2233 (2005) and published online 23 September 2005; herein incorporated by reference. Week 3 = 3 weeks after inoculation; Week 4 = 4 weeks after inoculation.

FIG 3

| Accession names and identifiers | Source History and Observations | Reference |
|---|---|---|
| PI 567597 C<br>Unverified name: Xiao huang dou<br><br>Type: UNVERIFIED.<br><br>Type: Inventory.<br>03U 2306, 93U 2010 | Type: Collected. From: Shandong, China.<br><br>Observations at world wide web.ars-grin.gov/cgi-bin/npgs/html/obs.pl?1500972 | USDA, ARS, National Genetic Resources Program. Germplasm Resources Information Network - (GRIN). [Online Database] National at world wide web.ars-grin.gov2/cgi-bin/npgs/html/acc_search.pl?accid=PI+567597+C (31 March 2005) |
| PI 567543 C<br>Unverified name: He nan chun<br><br>Type: UNVERIFIED.<br><br>Type: Inventory.<br>93U 1768, 94U 473 | Type: Collected. From: Shandong, China.<br><br>Observations at world wide web.ars-grin.gov/cgi-bin/npgs/html/obs.pl?1500927 | USDA, ARS, National Genetic Resources Program. Germplasm Resources Information Network - (GRIN). [Online Database] National Germplasm Resources Laboratory, Beltsville, Maryland. Available: at world wide web.ars-grin.gov2/cgi-bin/npgs/html/acc_search.pl?accid=PI+567543+C (31 March 2005) |
| PI 567598 B<br>Unverified name: Xiao jin huang lu dou<br><br>Type: UNVERIFIED.<br><br>Type: Inventory.<br>03U 2307, 93U 2012<br><br>PI assigned: 1993 | Type: Collected. From: Shandong, China.<br><br>Observations at world wide web.ars-grin.gov/cgi-bin/npgs/html/obs.pl?1500974 | USDA, ARS, National Genetic Resources Program. Germplasm Resources Information Network - (GRIN). [Online Database] National Germplasm Resources Laboratory, Beltsville, Maryland. Available: at world wide web.ars-grin.gov2/cgi-bin/npgs/html/acchtml.pl?1500974 (31 March 2005) |
| PI 567541 B<br>Unverified name: Gun li huang<br><br>Type: UNVERIFIED.<br><br>Type: Inventory.<br>93U 1759, 95U 470<br><br>PI assigned: 1993. | Type: Collected. From: Shandong, China.<br><br>Observations at world wide web.ars-grin.gov/cgi-bin/npgs/html/obs.pl?1500923 | USDA, ARS, National Genetic Resources Program. Germplasm Resources Information Network - (GRIN). [Online Database] National Germplasm Resources Laboratory, Beltsville, Maryland. Available: at world wide web.ars-grin.gov2/cgi-bin/npgs/html/acchtml.pl?1500923 (31 March 2005) |

* At world wide web.ars-grin.gov/cgi-bin/npgs/html/site.pl?SOY. NPGS received: 01-Apr-1993. Inventory volume: 202. Life form: Annual. Improvement status: Cultivated material. Reproductive uniformity: Pureline. Form received: Seed. Accession backed up at second site.

FIG 4

MARKERS FOR APHID RESISTANT GERMPLASM IN SOYBEAN PLANTS

This application claims priority to U.S. Non-Provisional patent application Ser. No. 11/436,262, which claims priority to U.S. Provisional Patent Application Ser. No. 60/682,583, filed 18 May 2005, which is herein incorporated by reference in its entirety.

FIELD OF THE INVENTION

The present invention relates to compositions and methods for providing and using markers of aphid resistant germplasm, particularly for identifying aphid resistance germplasm in soybean plants. Specifically, the inventions related to providing aphid resistant germplasm identified by markers associated with decreased damage from aphid feeding, as well as enhanced tolerance to aphid infestation of soybean plants. More particularly, the invention relates to compositions and methods for using genetic markers in breeding methods for producing plants with increased resistance to aphid damage and tolerance, while retaining and acquiring desired agronomic traits, Furthermore, the invention relates to plants produced by these breeding programs for use in commercial soybean production.

BACKGROUND OF THE INVENTION

Soybean is the leading oilseed crop produced and consumed worldwide (Wilcox World distribution and trade of soybean, 2004, Soybeans: Improvement, production, and Uses, 3rd ed., Agron. Monogr. 16, ASA, CSSA, and SSSA, Madison, Wis. p: 1-14; Hymowitz, 2004, Speciation and Cytogenetics. p. 97-136. In H. R. Boerma and J. E. Specht (ed) Soybeans: Improvement, production, and Uses. 3rd ed. Agron. Monogr. 16. ASA, CSSA, and SSSA). In the past half century, the USA has been the world's leading producer. In 2003, the USA produced 35% (65.8 million metric tons (MT)) of the world's total soybean (FAOSTAT, 2004, Production Crops). Soybean has many insect pests limiting its production in other parts of the world, including the soybean aphid.

Around 2000 A.D., the soybean aphid (*Aphis glycines* Matsumura) a native to eastern Asia, became a major sucking pest of soybean [*Glycine max* (L.) Merr.] in North America. Since then, this insect pest has rapidly spread to the major soybean production areas in the USA and Canada (Plant Health Initiative, 2004, Soybean Aphids Research Update "Aphids discovered in Wisconsin" from the North Central Soybean Research Program (NCSRP) published online by the Plant Health Initiative Available at planthealth.info/soyaphid.htm (verified Oct. 5, 2004). Aphid outbreaks have been severe in the northern part of the Midwestern USA and in Ontario, particularly in years 2001 and 2003.

Several factors affect soybean aphid outbreaks, including environmental conditions, over-wintering success, cultural practices, natural enemies, and the synchronization of soybean and aphid development (Wu et al., 1999, How Peasants Can Increase Wealth [Nongmin zhifu zhiyou] 6:20). The soybean aphid develops large colonies on soybean plants. Plant damage occurs when large numbers of aphids remove significant amounts of water and nutrients as they feed (suck) on leaves and stems, causing leaves to wilt, curl, yellow, and even drop off. Other symptoms of direct feeding damage include plant stunting, poor pod fill, reduced pod and seed counts, smaller seed size, and nutrient deficiencies resulting in overall yield and quality reduction (DiFonzo and Hines, 2002, Michigan State University Extension Bulletin E-2746). Significant yield loss (8-25%) occurs when the aphid heavily infests the soybean plants during the early reproductive stage (DiFonzo and Hines, 2002, Michigan State University Extension Bulletin E-2746). Honeydew, a sticky substance excreted by soybean aphids onto the leaves, leads to the development of sooty mold, which affects photosynthesis and results in yield loss (Baute, 2004, (Soybean Aphid Factsheet and Soybean Webpage sponsored by the Ontario Ministry of Agriculture, Food and Rural Affairs (OMAFRA), published online). During the feeding process, soybean aphids are capable of transmitting viruses including alfalfa mosaic virus, soybean mosaic virus, and bean yellow mosaic virus. These viruses commonly occur together and form a disease complex that leads to plant stunting, leaf distortion and leaf and stem mottling, reduced pod numbers, and seed discoloration (Glogoza, 2002, North Dakota State University Extension Bulletin E-1232).

Aphids are particularly difficult to control because of their rapid reproduction rates and ability to disperse over wide areas. Populations build rapidly (females give live birth, young mature in 3-7 days, doubling time 2-5 days under favorable conditions). Winged forms appear and disperse to other fields under high insect densities and when infested plants are stressed. Since aphids are relatively weak fliers, long-distance dispersal is often at the mercy of prevailing winds.

Aerial applicators frequently report having to stop to clean their windshields from flying into clouds of these aphids above heavily infested fields. In 2001, the influx of winged soybean aphids into the open dome of the Toronto Blue Jays even caused an early end to a Toronto Blue Jays game. It's these flights that lead to rapid, progressive colonization of soybean, almost like a wave moving across the countryside. Under favorable conditions for aphid infestations, the settling of winged aphids into uninfested fields has been described as "aphid rain." (Ostlie, Soybean Aphid Pages published online by Just for Growers, MN (University of Minnesota) Soybean Production, published online by the University of Minnesota, the University of Minnesota Extension Service, and the MN Soybean Research and Promotion Council Jul. 6, 2004).

Insecticides are the primary available method of controlling soybean aphids in the USA. Although the use of insecticides can be a quick and easy way to control aphids, the ideal time to spray is not well defined. Insecticides also have many adverse effects such as killing beneficial insects, environmental contamination, and increased production costs (Sun et al., 1991, Soybean Sci. 10 (2):98-103). Aphid populations may resurge when applications of insecticides are poorly timed or applied.

In the USA, there are currently no commercial soybean cultivars with aphid resistance and there are no reported resistance sources in early maturing soybean germplasm. Although there have been recent reports of aphid resistant soybean plants, (Hill et al., J. of Econ. Entomol. 97:1071-1077 (2004); Hill et al., Crop Sci. 44:98-106 (2004); Mueller, et al., The 2003 Entomological Society of America Annual Meeting and Exhibition Cincinnati, Ohio, October 2003, all of which are herein incorporated by reference), with further reports showing the results of studies on their effectiveness, (Li et al., J Econ Entomol. 2004 June; 97(3):1106-1111). These soybean plants are late maturing and not well suited for commercial development.

Currently none of the commercial soybean varieties show resistance to the aphid and further there are no sources of resistance reported in early maturing soybean germplasm in the USA. Therefore, developing soybean varieties that are resistant to the aphid is a long-term solution to the aphid problem.

SUMMARY OF THE INVENTION

The present invention relates to compositions and methods for providing and using markers of aphid resistant germplasm, particularly for identifying aphid resistance germplasm in soybean plants. Specifically, the inventions related to providing aphid resistant germplasm identified by markers associated with decreased damage from aphid feeding, as well as enhanced tolerance to aphid infestation of soybean plants. More particularly, the invention relates to compositions and methods for using genetic markers in breeding methods for producing plants with increased resistance to aphid damage and tolerance, while retaining and acquiring desired agronomic traits, Furthermore, the invention relates to plants produced by these breeding programs for use in commercial soybean production.

The present invention relates to compositions and methods for providing aphid resistance in plants. More particularly, the invention relates to compositions and methods for using aphid resistant germplasm for breeding soybean aphid resistant soybean plants, including but not limited to cultivars, varieties, lines and methods of breeding the same for commercial use, the breeding methods further involving identifying and using genetic markers for aphid resistant traits.

The present invention also relates to the field of plant breeding, specifically to methods of soybean breeding and the resulting soybean plants and soybean lines for commercial distribution. The soybean breeding methods include but are not limited to natural breeding, artificial breeding, molecular marker selection, commercial breeding, and transgenics. More particularly, the invention relates to producing soybean aphid-resistant plants, populations, cultivars, varieties, lines and methods of breeding the same, the methods further involving DNA molecular marker analysis.

The invention further relates to soybeans that are resistant to aphids, and in particular to germplasm that was identified as providing aphid resistance, methods of breeding aphid resistant soybean plants, and the resulting new aphid resistant soybean plant varieties, lines and cultivars developed through traditional plant breeding methods that provide for successful commercialization of the aphid resistant soybean germplasm. The present invention is not limited to any particular soybean variety, line, and cultivar having aphid resistance activities.

In some embodiments, the aphid resistant germplasm is deposited under the terms of the Budapest Treaty at the American Type Culture Collection (A.T.C.C./ATCC) 10801 University Boulevard, Manassas, Va., 20110-2209, The United States of America.

In some embodiments, the invention provides a soybean cultivar comprising aphid resistant germplasm, wherein said soybean cultivar is selected from a soybean maturity group consisting of 000, 00, 0, I, II, and III. In other embodiments, the present invention provides a soybean cultivar from an early maturing soybean maturity group of at least 000.1, 000.9, 00.1, 00.9, 0.1, 0.9, I.1 (1.1), I.9 (1.9), II.1 (2.1), II.9 (2.9), III.1 (3.1), and III.9 (3.9), wherein said soybean cultivar is an early maturing soybean. In some embodiments the soybean cultivar is from soybean maturity group III. In some embodiments, the present invention provides a soybean cultivar from soybean maturity group III of at least III (3.0), III.1 (3.1), III.2 (3.2), III.3 (3.3), III.4 (3.4), III.5 (3.5), III.6 (3.6), III.7 (3.7), III.8 (3.8), III.9 and (3.9). The present invention is not limited to any particular type of aphid resistance germplasm. Indeed, a variety of aphid resistance germplasm traits are contemplated, including, but not limited to antibiosis resistance toxicity to aphids, antixenosis resistance, and repellency to aphids. In some embodiments the soybean cultivar comprises aphid resistance germplasm wherein the aphid resistance is antibiosis resistance. In some embodiments the aphid resistance germplasm provides antibiosis resistance toxicity to aphids. In some embodiments the aphid resistance germplasm provides an aphid toxin. In some embodiments the soybean cultivar comprises aphid resistance germplasm wherein the aphid resistance is antixenosis resistance. In some embodiments the aphid resistance germplasm provides repellency to aphids. In some embodiments the aphid resistance germplasm provides an aphid repellant. In some embodiments the soybean cultivar comprises aphid resistant germplasm, wherein aphid resistant germplasm derives from an Asian soybean cultivar. In some embodiments the soybean cultivar is a *Glycine max* subsp *max*. In some embodiments the soybean cultivar further comprises introgressed germplasm for at least one desired trait. The present invention is not limited to any particular type of trait. Indeed a variety of traits are contemplated including but not limited to tolerance to an herbicide, resistance to an arthropod, resistance to a microorganism, resistance to a fungus, and an agronomic trait. In some embodiments the soybean cultivar further comprises introgressed germplasm for resistance to arthropods in addition to aphid resistance. The present invention is not limited to any particular type of arthropod. Indeed, a variety of arthropods are contemplated, including, but not limited to herbivore arthropods. In some embodiments the soybean cultivar further comprises introgressed germplasm for arthropod resistance to one or more of insecta including but not limited to Coleopteran, for example, *Matsumuraeses* sp., for example, bean pod worm (*Matsumuraeses phaseoli*), *Anthomomus* sp., such as a cotton boll weevil (*Anthomomus grandis*), *Cerotoma* sp., such as Bean Leaf Beetle (*Cerotoma trifurcate*), *Epilachna* sp. such as Mexican Bean Beetle (*Epilachna varivestris*), etc., *Melanoplus* sp., for example, red-legged grasshopper (*Melanoplus femurrubrum*), differential grasshopper (*Melanoplus differentialis*), American bird grasshopper or American grasshopper or American locust or American locust grasshopper (*Shistocerca Americana*), etc., and two-spotted spider mite (*Tetranychus urticae* Koch), etc.; Lepidopteran, such as *Anticarsia* sp. for example, Velvetbean Caterpillar (*Anticarsia gemmatalis*), *Pseudoplusia* sp., for example, Soybean Looper (*Pseudoplusia includens*), soybean pod borer (*Leguminivora glycinivorella*), *Plathypena* sp., green cloverworm (*Plathypena scabra* (F.)), *Heliothis* sp. for example, Tobacco budworm (*Heliothis virescens* (Fabricius)), cotton bollworm or corn earworm or soybean podworm (*Heliothis* (*Helicoverpa*)*zea*), etc.; *Spodoptera* sp., for example, fall armyworm (*Spodoptera frugiperda*), common cutworm (*Spodoptera litura* Fabricius), etc.; Hemiptera, for example, alfalfa hopper (*Spissistilus festinus*, Say), Pentatominae, such as green stink bug (Clemson) (*Acrosternum hilare* (Say)); brown stink bug (*Euschistus servus* (Say)); and southern green stink bug (*Nezara viridula* (L.)), East Asian stink bug or yellow-brown stink bug (Pentatomidae: *Halyomorpha halys*), etc.; and Cicadellidae, such as leafhoppers, for example, a potato leafhopper, a soybean leafhopper, for example, *Empoasca decipiens* Paoli, *Macrosteles quadripunctulatus* (KIrschbaum), *M. laevis* (Rib). *Psammotettix alienus* (Dahlbom), *P. Striatus* (Linne), and *Neoaliturus tenellus* (Baker).

In some embodiments the soybean cultivar further comprises introgressed germplasm for nematode resistance, for example, resistance to soybean cyst nematode (*Heterodera glycines*) and root knot nematode (*Meloidogyne* sp.).

In some embodiments the soybean cultivar further comprises introgressed germplasm for resistance to microorganisms and diseases caused by microorganisms. The present invention is not limited to any particular microorganism or disease. Indeed, a variety of microorganisms and diseases are contemplated, including, but not limited to microorganisms such as bacteria, viruses, fungi, and the like, and diseases thereof. In some embodiments the soybean cultivar further comprises introgressed germplasm for resistance to one or more of microorganisms such as fungi, including but not limited to *Phytophthora* sp., *Sclerotinia* sp., *Phytophthora* sp., *Fusarium* sp., *Phialophora* sp., *Peronospora* sp., *Cercospora* sp., *Diaporthe* sp., *Pythium* sp., soybean rust or Asian soybean rust fungus (*Phakopsora pachyrhizi*); bacteria, including but not limited to *Xanthomonas* sp.; virus including but not limited to Soybean mosaic virus, Bean Pod Mottle Virus, Peanut Mottle Virus, Soja virus, et cetera. In some embodiments the soybean cultivar further comprises introgressed germplasm for disease resistance to one or more diseases of leaf rot, brown leaf spot, frogeye leaf spot, stem rot, brown stem rot, stem canker, root rot, pod rot, powdery mildew, sudden death syndrome, bacterial pustule, reaction to bacterial pustule, bacterial blight, seedling blight, pod blight, stem blight, purple seed stain, mottling, stem mottling, pod mottling, leaf mottling, rust, soybean rust, rust, Asian soybean rust fungus a viral infection, a bacterial infection, a fungal infection, a nematode infection, insect feeding, and the like.

In some embodiments the aphid resistant soybean cultivar further comprises a selected agronomic trait. The present invention is not limited to any particular type of agronomic trait. Indeed, a variety of agronomic traits are contemplated, including, but not limited to a preferred oil content, protein content, seed protein content, seed size, seed color, seed coat thickness, seed sugar content, seed free amino acid content, seed germination rate, seed texture, seed fiber content, food-grade quality, hilium color, seed yield, maturity group, plant type, drought resistance, water resistance, cold weather resistance, hot weather resistance, and growth in a hardiness zone. In some embodiments the aphid resistant soybean plant comprises an agronomic trait comprising a seed trait, including, but not limited to a soybean seed with altered fatty acid content, such as altered linoleic acid content, altered polyunsaturated fat content, altered lipoxygenase activity, and the like. In some embodiments the soybean cultivar further comprises a plant part. The present invention is not limited to any particular type of plant part. Indeed, a variety of soybean plant parts are contemplated, including, but not limited to pollen, an ovule, a tissue, a pod, a seed, and a cell. In some embodiments the soybean cultivar further comprises an introgressed heterologous gene. The present invention is not limited to any particular type of heterologous gene. Indeed a variety of heterologous genes are contemplated, including, but not limited to a gene encoding an insecticidal protein, herbicide tolerance, and agronomic trait. In some embodiments the heterologous gene comprises one or more of a gene encoding an insecticidal protein, herbicide tolerance, and agronomic trait. In some embodiments the heterologous gene is a transgene. In some embodiments the transgene comprises one or more of a gene encoding an insecticidal protein, herbicide tolerance, and agronomic trait. In some embodiments the heterologous gene comprises one or more of a gene encoding a modified phosphinothricin acetyltransferase (PAT) from the soil bacterium *Streptomyces viridochromogenes*, fatty acid desaturase (GmFad2-1) from soybean, a modified 5-enolpyruvylshikimate-3-phosphate synthase (EPSPS) from the soil bacterium *Agrobacterium tumefaciens*, one or more of a *Bacillus thuringiensis* (Bt) insecticidal crystal protein tIC851, Bt Δ-endotoxin with insecticidal activity, mutant Bt Δ-endotoxins with insecticidal activity, crystal protein (Cry) Bt toxins with insecticidal activity, for example, a cryIIIC toxin, cryET1 toxin, PS63B, PS176 toxin, NRRL B-1 8721 toxin, Bt protease resistant toxins such as BTS02618Aa or BTS02618Ab Bt nematode-active toxins, an enzyme for altering a fatty acid, Δ-12 desaturase, plant acyl-ACP thioesterase, FAN1 protein for altering seed linolenic acid content, a palmitoyl-ACP thioesterase, an enzyme for reducing linolenic acid, an enzyme for reducing palmitic acid, an enzyme for increasing protein in a soybean seed, a protein for modifying an agronomic trait, a protein for providing an agronomic trait, and the like. In some embodiments, the invention provides an aphid resistant germplasm, wherein said aphid resistant germplasm is selected from an early maturing soybean cultivar. In other embodiments, the early maturing soybean cultivar is selected from the maturity group consisting of 000, 00, 0, I, II, and III. In other embodiments, the present invention provides aphid resistant germplasm from an early maturing soybean maturity group of at least 000.1, 000.9, 00.1, 00.9, 0.1, 0.9, I.11 (1.1), I.9 (1.9), II.1 (2.1), II.9 (2.9), III.1 (3.1), III.9 (3.9), wherein said aphid resistant germplasm is an early maturing soybean. In other embodiments, the aphid resistant germplasm derives from a soybean cultivar of the soybean maturity group III. In some embodiments, the present invention provides aphid resistance germplasm from soybean maturity group III is of at least III (3.0), III.1 (3.1), III.2 (3.2), III.3 (3.3), III.4 (3.4), III.5 (3.5), III.6 (3.6), III.7 (3.7), III.8 (3.8), III.9 and (3.9). In other embodiments, the aphid resistant germplasm provides antibiosis resistance. In other embodiments, the aphid resistance germplasm provides an aphid toxin. In other embodiments, the aphid resistance germplasm provides antixenosis resistance. In other embodiments, the aphid resistance germplasm provides an aphid repellant. In other embodiments, the aphid resistant germplasm derives from an Asian soybean cultivar. In other embodiments, the aphid resistant germplasm derives from a *Glycine max* subsp *max*.

In some embodiments, the invention provides a transgenic aphid resistant soybean plant. The present invention is not limited to any particular transgene of a transgenic aphid resistant soybean plant. Indeed, a variety of transgenes are contemplated, including, but not limited to a transgene encoding an insecticidal protein, herbicide tolerance, and an agronomic trait. In some embodiments the transgene comprises one or more of a gene encoding a modified phosphinothricin acetyltransferase (PAT) from the soil bacterium *Streptomyces viridochromogenes*, fatty acid desaturase (GmFad2-1) from soybean, a modified 5-enolpyruvylshikimate-3-phosphate synthase (EPSPS) from the soil bacterium *Agrobacterium tumefaciens*, one or more of a *Bacillus thuringiensis* (Bt) insecticidal crystal protein tIC851, Bt Δ-endotoxin with insecticidal activity, mutant Bt Δ-endotoxins with insecticidal activity, crystal protein (Cry) Bt toxins with insecticidal activity, for example, a cryIIIC toxin, cryET1 toxin, PS63B, PS176 toxin, NRRL B-1 8721 toxin, Bt protease resistant toxins such as BTS0261 8Aa or BTS02618Ab Bt nematode-active toxins, an enzyme for altering a fatty acid, Δ-12 desaturase, plant acyl-ACP thioesterase, FAN1 protein for altering seed linolenic acid content, a palmitoyl-ACP thioesterase, an enzyme for reducing linolenic acid, an enzyme for reducing palmitic acid, an enzyme for increasing protein in a soybean seed, a protein for modifying an agronomic trait, a protein for providing an agronomic trait, and the like. The present invention is not limited to any particular transgenic aphid resistant soybean plant. Indeed, a variety of transgenic aphid resistant soybean plants are contemplated, including, but not limited to an aphid resistant soybean plant comprising aphid resistant germplasm derived from one or more of soybean cultivars or lines designated PI567598B, PI567543C, PI567541B, PI567597C, line E06906, line E06902 deposited under American Type Culture Collection (ATCC) 10801 University Boulevard, Manassas, Va., 20110-2209, The United States of America, accession No: PTA-8794, line E06907, line E06901, and line E06904.

In some embodiments, the invention provides a method for producing a transgenic aphid resistant plant, comprising: an aphid resistant soybean plant, a transgene, and introducing the transgene into the aphid resistant soybean plant. The present invention is not limited to any particular aphid resistant soybean plant. Indeed, a variety of aphid resistant soybean plants are contemplated, including, but not limited to an aphid resistant soybean plant comprising aphid resistant germplasm derived from one or more of soybean cultivars or lines designated PI567598B, PI567543C, PI567541B, PI567597C, line E06906, line E06902 deposited under ATCC accession No: PTA-8794, line E06907, line E06901, and line E06904. The present invention is not limited to any particular transgene for producing a transgenic aphid resistant plant. Indeed, a variety of transgenes are contemplated, including, but not limited to a transgene encoding an insecticidal protein, herbicide tolerance, and an agronomic trait In some embodiments the transgene comprises one or more of a gene encoding a modified phosphinothricin acetyltransferase (PAT) from the soil bacterium Streptomyces viridochromogenes, fatty acid desaturase (GmFad2-1) from soybean, a modified 5-enolpyruvylshikimate-3-phosphate synthase (EPSPS) from the soil bacterium Agrobacterium tumefaciens, one or more of a Bacillus thuringiensis (Bt) insecticidal crystal protein tIC851, Bt Δ-endotoxin with insecticidal activity, mutant Bt Δ-endotoxins with insecticidal activity, crystal protein (Cry) Bt toxins with insecticidal activity, for example, a cryIIIC toxin, cryET1 toxin, PS63B, PS176 toxin, NRRL B-1 8721 toxin, Bt protease resistant toxins such as BTS02618Aa or BTS02618Ab Bt nematode-active toxins, an enzyme for altering a fatty acid, Δ-12 desaturase, plant acyl-ACP thioesterase, FAN1 protein for altering seed linolenic acid content, a palmitoyl-ACP thioesterase, an enzyme for reducing linolenic acid, an enzyme for reducing palmitic acid, an enzyme for increasing protein in a soybean seed, a protein for modifying an agronomic trait, a protein for providing an agronomic trait, and the like. The present invention is not limited to any particular method for introducing a transgene into an aphid, resistant soybean plant. Indeed, a variety of introduction methods are contemplated, including, but not limited to particle acceleration mediated transformation, biolistic transformation, Agrobacterium-mediated transformation, incubation in transformation medium, electroporation, microinjection, protoplast fusion, viral infection, and the like.

In some embodiments, the invention provides a method for producing an aphid resistant plant line, comprising: identifying germplasm conferring aphid resistance, wherein the aphid resistant germplasm derives from an aphid resistant soybean cultivar from the maturity group consisting of 000, 00, 0, I, II, and III; and introducing said germplasm into an elite soybean cultivar. In some embodiments the identifying aphid resistant germplasm conferring aphid resistance comprises molecular marker analysis of DNA samples isolated from one or more of an aphid resistant soybean plant, an aphid resistant soybean cultivar, a non-aphid resistant soybean plant, and a non-aphid resistant soybean cultivar, wherein said analysis identifies DNA molecules associated with aphid resistance. The present invention is not limited to any particular type of molecular marker. Indeed, a variety of molecular markers are contemplated, including, but not limited to a simple sequence repeat (SSR) analysis, a single nucleotide polymorphism analysis (SNP), a random amplified polymorphic DNA analysis (RAPD), and an amplified fragment length polymorphism analysis (AFLP). In some embodiments the identifying aphid resistant germplasm conferring aphid resistance comprises identifying linkage groups associated with aphid resistant germplasm. In some embodiments the identifying aphid resistant germplasm conferring aphid resistance comprises using simple sequence repeat markers for identifying linkage groups comprising aphid resistant germplasm. In some embodiments, a simple sequence repeat marker is selected from one or more of soybean "Satt," "Sat," "Sctt," "Satgt," "Scaa," "Staga," or "Sct" markers. The present invention is not limited to any particular type of Satt marker. Indeed, a variety of simple sequence repeat markers are contemplated, including, but not limited to a Satt271, Satt280, Satt304, Satt439, Satt468, Satt529, Satt686, and Satt628 marker and their PCR primer pairs. In some embodiments, a Satt marker is selected from one or more of a PCR primer pair of Satt271 (SEQ ID NO:01 Forward primer and SEQ ID NO:02 Reverse primer), Satt280 (SEQ ID NO:03 Forward primer and SEQ ID NO:04 Reverse primer), Satt304 (SEQ ID NO:05 Forward primer and SEQ ID NO:06 Reverse primer), Satt439 (SEQ ID NO:07 Forward primer and SEQ ID NO:08 Reverse primer), Satt468 (SEQ ID NO:09 Forward primer and SEQ ID NO:10 Reverse primer), Satt529 (SEQ ID NO:11 Forward primer and SEQ ID NO:12 Reverse primer), Satt628 (SEQ ID NO:13 Forward primer and SEQ ID NO:14 Reverse primer), and Satt686 (SEQ ID NO:15 Forward primer and SEQ ID NO:16 Reverse primer). In some embodiments, the association of a Satt marker to a linkage group comprising aphid resistant germplasm is demonstrated by using one or more of a PCR primer pair of Satt271 (SEQ ID NO:01 Forward primer and SEQ ID NO:02 Reverse primer), Satt280 (SEQ ID NO:03 Forward primer and SEQ ID NO:04 Reverse primer), Satt304 (SEQ ID NO:05 Forward primer and SEQ ID NO:06 Reverse primer), Satt439 (SEQ ID NO:07 Forward primer and SEQ ID NO:08 Reverse primer), Satt468 (SEQ ID NO:09 Forward primer and SEQ ID NO:10 Reverse primer), Satt529 (SEQ ID NO:11 Forward primer and SEQ ID NO:12 Reverse primer), Satt628 (SEQ ID NO:13 Forward primer and SEQ ID NO:14 Reverse primer), and Satt686 (SEQ ID NO:15 Forward primer and SEQ ID NO:16 Reverse primer). In some embodiments the molecular marker analysis provides a DNA fingerprint of aphid resistant germplasm. In some embodiments the DNA molecule is a marker for an allele of a quantitative trait locus associated with aphid resistant germplasm. In some embodiments the allele provides enhanced aphid resistance. In some embodiments, the invention provides an isolated DNA molecule associated with germplasm conferring aphid resistance. The present invention is not limited to any particular elite soybean cultivars or varieties or maturity group. Indeed, a variety of elite soybean cultivars are contemplated, including, but not limited to PI257345 and its progeny S1346, PI71506, Hutcheson, Resnik, Lincoln, Richland, Patoka, PI 81041, Illini, PI 54610, PI 88788, Mukden, Palmetto, Haberlandt No. 171, PI 257345, PI 71506, Lincoln, Mandarin (Ottawa), PI 90763, CNS, PI 209332, Richland, Tokyo, S-100, Minsoy, Ogden, Noir 1, A.K. (Harrow), Archer, Dunfield, Evans, Mukden, Clark, Jackson, Harosoy, Illini, Essex, Roanoke, PI 88788, Peking, Asgrow AG4201, Asgrow AG3703, Croplan Genetics RC4432, A2704-12, A2704-21, A5547-35 (Aventis Crop Science), A5547-127, GU262, W62, W98, (Bayer Crop Science (Aventis Crop Science (AgrEvo))), G94-1, G94-19, G168 (DuPont Canada Agricultural Products), GTS 40-3-2 (Monsanto Company), OT96-15 (Agriculture & Agri-Food Canada), Maple Glen, PI361088B and Roundup Ready Soybeans. In some embodiments the aphid resistant soybean cultivar is an Asian soybean cultivar. In some embodiments the aphid resistant soybean cultivar is a Glycine max subsp. Max. In some embodiments the aphid resistant germplasm comprises soybean germplasm derived from one or more of PI 567543C, PI 567597C, PI 567541B, and PI 567598B cultivars obtained from the USDA Soybean Germplasm. In some embodiments, the aphid resistant soybean cultivar derives from one or more of soybean line E06906, E06902 deposited under ATCC accession No: PTA-8794, E06907, E06901, and E06904, a soybean progeny plant from crossing PI 567598B×PI 567597C and soybean plants of population Identification (ID) numbers 020138-1, 030100-1, 030100-2, 030100-3, and 030100-4. In some embodiments producing an aphid resistant plant line further comprises crossing a first soybean plant, wherein said first soybean plant provides aphid resistant germplasm, with a second soybean plant and harvesting the resultant hybrid soybean seed. In some embodiments the first soybean plant comprises aphid resistant germplasm from one or more of PI 567543C, PI 567597C, PI 567541B, and PT 567598B. In some embodiments the first soybean plant comprises aphid resistant germplasm from one or more of soybean line E06906, E06902 deposited under ATCC accession No: PTA-8794, E06907, E06901, and E06904.

In some embodiments the second soybean plant is one or more of accession PI 567598B, accession PI 567543C, accession PI 567541B, accession PI 567597C, a line E06906, a line E06902, a line E06907, a line E06901, a line E06904, a variety Titan, a variety Loda, a line E00075 and a line E99034. In some embodiments the second soybean plant is one or more of an elite soybean plant. In some embodiments the crossing further comprises introgressing aphid resistance into hybrid soybean seed. In some embodiments the crossing further comprises one or more of a backcrossing, an outcrossing, and a self-crossing. In some embodiments the identifying aphid resistant germplasm further comprises molecular marker analysis of DNA samples isolated from one or more of a progeny plant, a second soybean plant, an aphid resistant donor soybean cultivar, a parental aphid resistant soybean cultivar, and a non-aphid resistant soybean cultivar, wherein said analysis identifies DNA molecules associated with aphid resistance. The present invention is not limited to any particular type of molecular marker. Indeed, a variety of molecular markers are contemplated, including, but not limited to a simple sequence repeat (SSR) analysis, a single nucleotide polymorphism analysis (SNP), a random amplified polymorphic DNA analysis (RAPD), and an amplified fragment length polymorphism analysis (AFLP). In some embodiments, the molecular marker analysis is selected from one or more of a simple sequence repeat (SSR) analysis, a single nucleotide polymorphism analysis (SNP), a random amplified polymorphic DNA analysis (RAPD), and an amplified fragment length polymorphism analysis (AFLP). In some embodiments, an SSR marker is selected from one or more of a "Satt," "Sat," "Sctt," "Satgt," "Scaa," "Staga," or "Sct" marker. The present invention is not limited to any particular type of Satt marker. Indeed, a variety of molecular markers are contemplated, including, but not limited to a Satt271, Satt280, Satt304, Satt439, Satt468, Satt529, Satt686, and Satt628 marker. In some embodiments, a Satt marker is selected from one or more of a Satt271 (SEQ ID NO:01 Forward primer and SEQ ID NO:02 Reverse primer), Satt280 (SEQ ID NO:03 Forward primer and SEQ ID NO:04 Reverse primer), Satt304 (SEQ ID NO:05 Forward primer and SEQ ID NO:06 Reverse primer), Satt439 (SEQ ID NO:07 Forward primer and SEQ ID NO:08 Reverse primer), Satt468 (SEQ ID NO:09 Forward primer and SEQ ID NO:10 Reverse primer), Satt529 (SEQ ID NO:11 Forward primer and SEQ ID NO:12 Reverse primer), Satt628 (SEQ ID NO:13 Forward primer and SEQ ID NO:14 Reverse primer), and Satt686 (SEQ ID NO:15 Forward primer and SEQ ID NO:16 Reverse primer). In some embodiments the molecular marker analysis provides a DNA fingerprint of aphid resistant germplasm. In some embodiments the DNA molecule is a marker for an allele of a quantitative trait locus. In some embodiments the allele provides enhanced aphid resistance. In some embodiments, the invention provides a method for isolating an aphid resistant DNA molecule, comprising, providing, a soybean genomic DNA library selected from germplasm of one or more of soybean populations designated 030100-1, 030100-2, 030100-3, and 030100-4 and isolating said DNA molecule from said library.

In some embodiments, the invention provides a method for isolating an aphid resistant DNA molecule, comprising, providing, a soybean linkage group germplasm selected from germplasm of one or more of soybean populations designated 030100-1, 030100-2, 030100-3, and 030100-4 and isolating said DNA molecule from said library.

In some embodiments, the invention provides a method for isolating an aphid resistant DNA molecule, comprising, providing, a soybean linkage group germplasm selected from germplasm of one or more of linkage groups J, K, B2, D1a, and D1b and isolating said DNA molecule from said linkage group.

In some embodiments the aphid resistant germplasm comprises a linkage group selected from one of more of linkage groups J, K, B2, D1a, and D1b.

In some embodiments, the invention provides an isolated DNA molecule associated with aphid resistant germplasm of a soybean plant, wherein said soybean plant is a cultivar selected from the soybean maturity group consisting of 000, 00, 0, I, II, and III. In some embodiments the soybean cultivar is an Asian soybean cultivar. In some embodiments the soybean cultivar is a Glycine max subsp. Max.

In some embodiments, the invention provides a soybean cultivar, wherein at least one ancestor of the soybean cultivar comprises aphid resistant germplasm of one or more of a soybean cultivar designated PI 567543C, PI 567597C, PI 567541B, and PI 567598B. In some embodiments, the invention provides a soybean cultivar, wherein at least one ancestor of the soybean cultivar comprises aphid resistant germplasm of one or more of a soybean line E06906, line E06902 deposited under ATCC accession No: PTA-8794, line E06907, line E06901, and line E06904. In some embodiments, the invention provides a soybean cultivar with resistance to a soybean aphid comprising germplasm of one or more of a soybean cultivar designated PI 567543C, PI 567597C, PI 567541B, and PI 567598B. In some embodiments, the invention provides a soybean cultivar with resistance to a soybean aphid comprising germplasm of one or more of a soybean line designated E06906, E06902 deposited under ATCC accession No: PTA-8794, E06907, E06901, and E06904. In some embodiments, the invention provides a soybean line with resistance to a soybean aphid comprising germplasm of one or more of a soybean line designated E06906, E06902 deposited under ATCC accession No: PTA-8794, E06907, E06901d, and E06904. In some embodiments the resistant germplasm comprises antibiosis resistance germplasm. In some embodiments the resistant germplasm comprises antixenosis resistance. In some embodiments the soybean cultivar is selected from the soybean maturity group comprising 000, 00, 0, I, II, III, IV, V, VI, VII, VIII, IX, and X. In other embodiments, the present invention provides the soybean cultivar is selected from the soybean maturity group of at least 000.1, 000.9, 00.1, 00.9, 0.1, 0.9, I.11 (1.1), I.9 (1.9), II.1 (2.1), II.9 (2.9), III.1 (3.1), III.9 (3.9), IV.1 (4.1), IV.9 (4.9), V.1 (5.1), V.9 (5.9), VI.1 (6.1), VI.9 (6.9), VII.1 (7.1), VII.9 (7.9), VIII.1 (8.1), VIII.9 (8.9), IX.1 (9.1), IX.9 (9.9), X.1 (10.1), and X.9 (10.9). In some embodiments the soybean cultivar further comprises a selected agronomic trait. In some embodiments the agronomic trait comprises one or more of a preferred oil content, protein content, seed protein content, seed size, seed color, seed coat thickness, seed sugar content, seed free amino acid content, seed germination rate, seed texture, seed fiber content, food-grade quality, hilium color, seed yield, maturity group, plant type, drought resistance, water resistance, cold weather resistance, hot weather resistance, and growth in a hardiness zone. In some embodiments the aphid resistant soybean plant comprises an agronomic trait comprising a seed trait, including, but not limited to a soybean seed with altered fatty acid content, such as altered linoleic acid content, altered polyunsaturated fat content, altered lipoxygenase, and the like.

In some embodiments, the invention provides an aphid toxin, comprising germplasm from one or more of a soybean cultivar designated PI 567541B and PI 567598B. In some embodiments, the invention provides an aphid toxin, comprising germplasm from one or more of a soybean line designated E06906, E06902 deposited under ATCC accession No: PTA-8794, E06907, E06901, and E06904.

In some embodiments, the invention provides a soybean cultivar with resistance to a soybean aphid comprising germplasm designated PI 567543C and PI 567597C, wherein said resistance is an antixenosis resistance.

In some embodiments, the invention provides an aphid repellant, comprising germplasm from one or more of a soybean cultivar designated PI 567543C and PI 567597C.

In some embodiments, the invention provides an aphid repellant, comprising germplasm from one or more of a soybean line designated E06906, deposited under ATCC accession No: PTA-8794, E06907, E06901, and E06904.

In some embodiments, the invention provides a soybean plant part comprising aphid resistant germplasm of one or more of a soybean cultivar designated PI 567543C, PI 567597C, PI 567541B, and PI 567598B.

In some embodiments, the invention provides a soybean plant part comprising aphid resistant germplasm of one or more of a soybean line designated E06906, E06902 deposited under ATCC accession No: PTA-8794, E06907, E06901, and E06904.

In some embodiments the soybean plant part is one or more of a pollen grain, an ovule, a tissue, a pod, a seed, and a cell.

In some embodiments, the invention provides a breeding method for producing a commercial variety of an aphid resistant soybean plant, wherein said aphid resistant soybean plant comprises crossing a first hybrid plant comprising aphid resistant germplasm from one or more of a soybean cultivar germplasm designated PI 567543C, PI 567597C, PI 567541B, and PI 567598B with a second soybean plant.

In some embodiments, the invention provides a breeding method for producing a commercial variety of an aphid resistant soybean plant, wherein said aphid resistant soybean plant comprises crossing a first hybrid plant comprising aphid resistant germplasm from one or more of soybean germplasm designated line designated E06906, E06902 deposited under ATCC accession No: PTA-8794, E06907, E06901, and E06904, with a second soybean plant. In some embodiments the second soybean plant comprises aphid resistant germplasm from one or more of a soybean cultivar germplasm designated PI 567543C, PI 567597C, PI 567541B, and PI 567598B. In some embodiments the second soybean plant comprises aphid resistant germplasm from one or more of a soybean line germplasm designated E06906, E06902 deposited under ATCC accession No: PTA-8794, E06907, E06901, and E06904 with a second soybean plant. In some embodiments the first soybean plant and said second soybean plant are different soybean plants. In some embodiments the first soybean plant and said second soybean plant are unrelated soybean plants. In some embodiments the first soybean plant and said second soybean plant are the same soybean plant. In some embodiments the first soybean plant and said second soybean plant are related soybean plants. In some embodiments the crossing comprises one or more a backcrossing, an outcrossing, and a self-crossing. In some embodiments the producing further comprises using a molecular marker for identifying a gene associated with aphid resistance in a first soybean plant. In some embodiments the commercial variety of an aphid resistant soybean plant further comprises a selected agronomic trait. In some embodiments the agronomic trait further comprises one or more of a preferred oil content, protein content, seed protein content, seed size, seed color, seed coat thickness, seed sugar content, seed free amino acid content, seed germination rate, seed texture, seed fiber content, food-grade quality, clear hilium, seed yield, drought resistance, water resistance, cold weather resistance, hot weather resistance, and growth in a hardiness zone.

In some embodiments, the invention provides a DNA molecular marker associated with aphid resistance of a soybean plant comprising germplasm from one or more of a soybean cultivar designated PI 567543C, PI 567597C, PI 567541B, and PI 567598B, wherein the DNA molecule provides aphid resistance in a soybean plant.

In some embodiments, the invention provides an isolated DNA molecule associated with aphid resistance of a soybean plant comprising germplasm from one or more of a soybean cultivar designated PI 567543C, PI 567597C, PI 567541B, and PI 567598B, wherein the DNA molecule provides enhanced aphid resistance in a soybean plant.

In some embodiments, the invention provides a DNA molecule associated with aphid resistance of a soybean plant comprising germplasm from one or more of a soybean cultivar designated PI 567543C, PI 567597C, PI 567541B, and PI 567598B, wherein said DNA molecule is a marker for an allele of a quantitative trait locus. In some embodiments the allele provides enhanced aphid resistance in a soybean plant. In some embodiments the quantitative trait locus provides enhanced aphid resistance in a soybean plant.

In some embodiments, the invention provides a method for isolating an aphid resistant DNA molecule, comprising, providing, a soybean genomic DNA library selected from germplasm of one or more of soybean cultivars designated PI 567543C, PI 567597C, PI 567541B, and PI 567598B and isolating said DNA molecule from said library.

In some embodiments, the invention provides a soybean plant of cultivar PI 567543C.

In some embodiments, the invention provides a soybean plant part of cultivar PI 567543C, and said soybean plant part is one or more of a pollen, an ovule, a tissue, a pod, a seed, and a cell.

In some embodiments, the invention provides a soybean plant of cultivar PI 567597C.

In some embodiments, the invention provides a soybean plant part of cultivar PI 567597C, and said soybean plant part is one or more of a pollen, an ovule, a tissue, a pod, a seed, and a cell.

In some embodiments, the invention provides a soybean plant of cultivar PI 567541B.

In some embodiments, the invention provides a soybean plant part of cultivar PI 567541 and said soybean plant part is one or more of a pollen, an ovule, a tissue, a pod, a seed, and a cell.

In some embodiments, the invention provides a soybean plant of cultivar PI 567598B.

In some embodiments, the invention provides a soybean plant part of cultivar PI 567598B, and said soybean plant part is one or more of a pollen, an ovule, a tissue, a pod, a seed, and a cell.

In some embodiments, the invention provides an aphid resistant germplasm of a soybean plant part of cultivar PI 567541B, and said soybean plant part is one or more of a pollen, an ovule, a tissue, a pod, a seed, and a cell.

In some embodiments, the invention provides an aphid resistant germplasm of a soybean plant of cultivar PI 567541B.

In some embodiments, the invention provides an aphid resistant germplasm of a soybean plant part of cultivar PI 567597C, and said soybean plant part is one or more of a pollen, an ovule, a tissue, a pod, a seed, and a cell.

In some embodiments, the invention provides an aphid resistant germplasm of a soybean plant of cultivar PI 567597C.

In some embodiments, the invention provides an aphid resistant germplasm of a soybean plant part of cultivar PI 567543C, and said soybean plant part is one or more of a pollen, an ovule, a tissue, a pod, a seed, and a cell.

In some embodiments, the invention provides an aphid resistant germplasm of a soybean plant of cultivar PI 567543C.

In some embodiments, the invention provides an aphid resistant germplasm of a soybean plant part of cultivar PI 567598B, and said soybean plant part is one or more of a pollen, an ovule, a tissue, a pod, a seed, and a cell.

In some embodiments, the invention provides an aphid resistant germplasm of a soybean plant of cultivar PI 567598B.

In some embodiments, the invention provides an aphid resistant germplasm of a soybean plant part of line E06906, and said soybean plant part is one or more of a pollen, an ovule, a tissue, a pod, a seed, and a cell.

In some embodiments, the invention provides an aphid resistant germplasm of a soybean plant of line E06906 and seed of said cultivar.

In some embodiments, the invention provides an aphid resistant germplasm of a soybean plant part of line E06902, wherein seed of said cultivar having been deposited under ATCC accession No: PTA-8794, and said soybean plant part is one or more of a pollen, an ovule, a tissue, a pod, a seed, and a cell.

In some embodiments, the invention provides an aphid resistant germplasm of a soybean plant of line E06902, wherein seed of said cultivar having been deposited under ATCC accession No: PTA-8794.

In some embodiments, the invention provides an aphid resistant germplasm of a soybean plant part of line E06907, and said soybean plant part is one or more of a pollen, an ovule, a tissue, a pod, a seed, and a cell.

In some embodiments, the invention provides an aphid resistant germplasm of a soybean plant of line E06907, and seed of said cultivar.

In some embodiments, the invention provides an aphid resistant germplasm of a soybean plant part of line E06901, and said soybean plant part is one or more of a pollen, an ovule, a tissue, a pod, a seed, and a cell.

In some embodiments, the invention provides an aphid resistant germplasm of a soybean plant of line E06901, and seed of said cultivar.

In some embodiments, the invention provides an aphid resistant germplasm of a soybean plant part of line E06904, and said soybean plant part is one or more of a pollen, an ovule, a tissue, a pod, a seed, and a cell.

In some embodiments, the invention provides an aphid resistant germplasm of a soybean plant of line E06904, and seed of said cultivar.

The present inventions provide a composition, comprising, aphid resistant plant germplasm and a molecular marker selected from the linkage groups consisting of F, M, and J. In some embodiments the marker is selected from the group consisting of simple sequence repeat (SSR), single nucleotide polymorphism (SNP), random amplified polymorphic DNA (RAPID), and amplified fragment length polymorphism (AFLP). In some embodiments the marker is a polymerase chain reaction primer sequence selected from the group consisting of SEQ ID NOs: 1-90 and at least one primer which is a variant of any one of said SEQ ID NOs: 1-90. In some embodiments the germplasm is isolated from a soybean plant selected from the group consisting of accession PI567598B, accession PI567543C, accession PI567541B, accession PI567597C, line E06902 deposited under ATCC accession No: PTA-8794, hybrids thereof and progeny thereof. In some embodiments the composition is created from the group consisting of a polymerase chain reaction product, a restriction fragment length polymorphism analysis, amplification fragment length polymorphism analysis, a microsatellite amplification, hybridization, and a southern blot.

The present inventions provide a method of identifying a marker for aphid resistance, comprising, a) providing, i) a molecular marker, and ii) a first soybean plant germplasm, wherein said germplasm comprises nucleic acid sequences isolated from a soybean plant having a phenotype of aphid resistance, and iii) a second soybean plant germplasm, wherein said germplasm comprises nucleic acid sequences isolated from a soybean plant having less aphid resistance than the first soybean plant, and b) detecting a product that is different from the second soybean plant germplasm. In one embodiment, the method further comprises hybridizing the molecular marker to said nucleic acid sequences from said first soybean plant and said second soybean plant, wherein said detecting is the presence and absence of a hybridization product. In one embodiment, the method further provides a second molecular marker and comprising hybridizing said second molecular marker to said nucleic acid sequences from said first and said second soybean plant, wherein said detecting is the presence and absence of a hybridization product. In one embodiment, the method further comprises nucleic acid amplification. In some embodiments the molecular marker comprises a primer set consisting of a forward and reverse primer to replicate at least a portion of the nucleic acid sequences. In some embodiments the primer set is selected from the group consisting of SEQ ID NOs: 1-90 and at least one primer sequence which is a variant of any one of said SEQ ID NOs: 1-90. In some embodiments the said detecting a product is an observation of a band present in germplasm from an aphid resistant soybean plant that is not present in the germplasm from a soybean plant with less aphid resistance. In some embodiments the said observation of a band is an observation of a band of a certain molecular weight that is not present in the germplasm from a soybean plant with less aphid resistance. In some embodiments the said band is an allele present in germplasm from an aphid resistant soybean plant that is not present in the germplasm from a soybean plant with less aphid resistance. In some embodiments the said observation of a band is an observation of a band pattern. In some embodiments the said detecting is using a technique selected from the group consisting of restriction fragment length polymorphism analysis, amplification fragment length polymorphism analysis, microsatellite amplification, southern blotting, and nucleic acid sequencing. In some embodiments the detected allele is present in a soybean plant having a phenotype of enhanced aphid resistance.

The present inventions provides a method of breeding, comprising, a) providing, i) a first soybean plant comprising aphid resistant germplasm, ii) second soybean plant, and iii) a molecular marker, and b) crossing said first soybean plant with said second soybean plant, and using said molecular marker for identifying germplasm associated with aphid resistance. In some embodiments the first soybean plant is selected from the group consisting of accession PI567598B, accession PI567543C, accession PI567541B, accession PI567597C, line E06902 deposited under ATCC accession No: PTA-8794, hybrids thereof and progeny thereof. In some embodiments the marker identifies a region of a linkage group selected from the group consisting of F, M, and J. In some embodiments the marker identifies a marker selected from the group consisting of Satt343, Satt193. Satt649, Satt150, Satt435, Sat_299, Sat_339, Satt414, Satt654, Satt596, Satt686, Satt622, Satt380, Satt596, Satt456, Satt529, Satt183, Satt215, Sat_366, Sat_350, Satt380, Satt596, Satt456, Satt529, Satt183, Satt215, Sat_366, and Sat_350. In some embodiments the first soybean plant is selected from the group consisting of accession PI 567541B, line E06902 deposited under ATCC accession No: PTA-8794, hybrids thereof and progeny thereof. In some embodiments the marker is selected from a linkage group selected from the group consisting of F and M. In some embodiments the marker for linkage group F is selected from the group consisting of Satt343, Satt193, and Satt649. In some embodiments the marker for linkage group M is selected from the group consisting of Satt150, Satt435, and Sat_299. In some embodiments the second soybean plant is selected from the group consisting of aphid resistant soybean plants and susceptible soybean plants. In some embodiments the crossing further comprises one or more of a backcrossing, an outcrossing, and a self-crossing. In some embodiments the crossing creates soybean seed. In some embodiments the seed is germinated and grown into progeny soybean plants. In some embodiments the progeny soybean plants provide germplasm for use with said markers. In some embodiments the using said markers is identifying the aphid resistant germplasm in the first soybean plants.

The present inventions provides a method, comprising, a) providing, ii) a soybean plant comprising aphid resistant germplasm, iii) a molecular marker, and b) using said molecular marker for identifying aphid resistant germplasm in a soybean plant. In one embodiment, the method further comprises testing a line of said soybean plants for an aphid resistant phenotype.

The present invention comprises a method, comprising, providing, a first aphid resistant soybean plant, wherein said plant aphid resistant germplasm comprises antibiosis aphid resistant germplasm and a second soybean plant, wherein said plant comprises antixenosis aphid resistance germplasm, and growing said first soybean plant until aphids overcome resistance then growing said second soybean plants.

The present invention comprises a method, comprising, providing, a first aphid resistant soybean plant, wherein said plant comprises aphid resistant germplasm derived from accession PI567598B, accession PI567541B, and line E06902 deposited under ATCC accession No: PTA-8794, hybrids thereof and progeny thereof and a second soybean plant, wherein said plant comprises aphid resistant germplasm derived from accession PI 567543C, PI 567597C.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows exemplary results of choice testing soybean aphid resistance in progeny of aphid resistant cultivars.

FIG. 4 shows exemplary resource information for a soybean aphid resistant soybean cultivar accessions PI 567597C, PI 567543C, PI 567598B, and PI 567541B at the time these accessions were obtained from the USDA Soybean Germplasm Database.

DEFINITIONS

Figure 1:
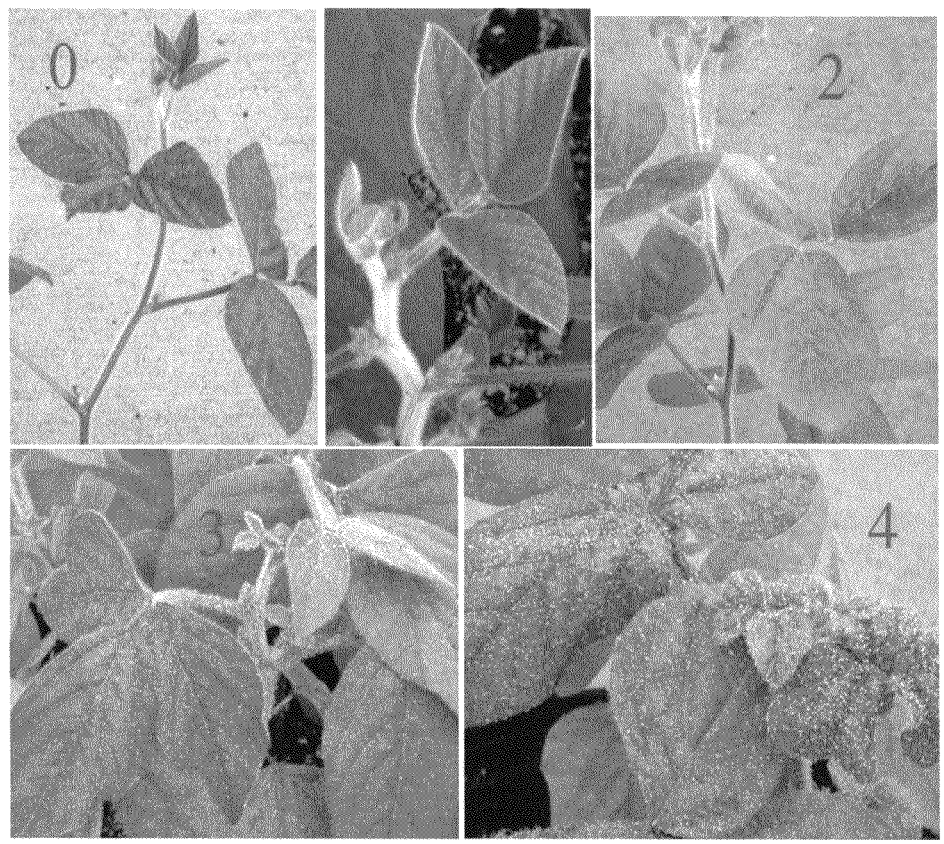
FIG. 1 shows an exemplary illustration of the visual rating scale used to establish the Damage Index (DI). 0=No aphids, plant appears normal and healthy; 1=Less than 100 aphids per plant, plant appears normal and healthy; 2=101-300 aphids per plant, mostly on the young leaves and the tender stem at top of plant, plant appears normal and healthy; 3=301-800 aphids per plant, leaves slightly curly and shiny, young leaves and stems covered with aphids; 4=More than 800 aphids per plant, plants stunted, leaves severely curled, yellow, covered with sooty mold and cast skins.

To facilitate an understanding of the present invention, a number of terms and phrases are defined below:

The use of the article "a" or "an" is intended to include one or more.

As used herein, the term "aphid" refers to any of various small plant-sucking insects with or without wings of the order Homoptera, further of the family Aphididae, wherein examples of Aphididae include but are not limited to a genius of *Aphis, Acyrthosiphum, Brevicoryne, Cavariella, Chaitophorus, Cinara, Diuraphis, Drepanosiphum, Elatobium, Macrosiphum, Megoura, Myzus, Phorodon, Rhopalosiphum, Sitobion, Toxoptera, Therioaphis, Tuberocephalus*, etc. while even further any one or more of the following genus-species of *Aphis*, for example, soybean aphid *Aphis glycines* Matsumura, Black Bean Aphid *Aphis faba*, Groundnut Aphid *Aphis craccivora* Cotton Aphid *Aphis gossypii* cotton/melon aphid, *Aphis gossypii, Acyrthosiphum*, for example, Pea Aphid *Acyrthosiphum pisum, Brevicoryne*, for example, Cabbage Aphid *Brevicoryne brassicae, Cavariella*, for example, Carrot Aphid *Cavariella aegopodii* Willow Aphid *Cavariella* spp. *Chaitophorus*, for example, Willow Leaf Aphids *Chaitophorus* spp., *Cinara*, for example, Black Pine Aphids *Cinara* spp., *Diuraphis*, for example, Russian wheat aphid *Diuraphis noxia, Drepanosiphum*, for example, Sycamore Aphid *Drepanosiphum platanoides, Elatobium*, for example, Spruce Aphids *Elatobium* spp., *Macrosiphum*, for example, English Grain Aphid *Macrosiphum avenae, Megoura*, for example, Vetch aphid Megoura viciae, Myzus, for example, Peach-Potato *Myzus persicae, Phorodon*, for example, Damson hop aphid *Phorodon humuli, Sitobion*, for example, Grain Aphid *Sitobion avenae, Rhopalosiphum* for example, Corn Leaf Aphid *Rhopalosiphum maidis*, the Oat Bird-Cherry Aphid *Rhopalosiphum padi Toxoptera*, for example, Black Citrus Aphid *Toxoptera auranti, Therioaphis*, for example, spotted alfalfa aphid *Therioaphis maculata, Tuberocephalus*, for example, peach aphid *Tuberocephalus momonis*, Giant Willow aphid *Tuberolachnus salignus* (aka *Lachnus salignus*) Gmellin and the like. For the purposes of the present invention, an aphid is a pest.

As used herein, the terms "soybean aphid" and "*Aphis glycines*" and "*Aphis glycines* Matsumura" refers to an aphid that feeds on soybeans, for example, an aphid that derived from an eastern Asian soybean aphid. However for the compositions and methods of the present invention, any aphid that may be found on and thus potentially feed on a soybean plant, such as a cotton/melon aphid, *Aphis gossypii* Glover, is an aphid target for aphid soybean resistance.

As used herein, the terms "arthropoda" and "arthropods" refer to a branch (phylum) of the animal kingdom whose members have jointed legs and are also made up of rings or segments, for example, Insecta, crustaceans, spiders, and the like. As used herein, some arthropod larvae (for example, grubs and maggots) are legless while spiders and ticks have four pairs of jointed legs.

As used herein, the terms "insect" and "Insecta" refer to a Class of Arthropoda whose members have a body with distinct head, thorax and abdomen; the head bears one pair of antennae and paired mouthparts; the thorax bears three pairs of legs and one or two pairs of wings in winged insects (Pterygota) and none in primarily wingless insects (Apterygota); the abdomen bears no legs but other appendages might be present with three pairs of jointed legs and one pair of antennae, at least in the adult phase, for example, aphids, Lepidoptera, such as butterflies and moths, Coleoptera, such as Beetles, have this arrangement in the adult phase. As used herein, some insect larvae (for example, grubs) are legless.

As used herein, the terms "Nematoda" or "nemathelminths" refer to a branch (phylum) of the animal kingdom whose members include "nematode" and "roundworm" organisms that are bilaterally symmetrical and surrounded by a strong and flexible noncellular layer called a cuticle, such as a *Heterodera glycines* soybean cyst nematode.

As used herein, the terms "Sudden Death Syndrome" or "SDS" refer to a fungal disease of soybeans caused by a fungus, such as *Fusarium solani* fungus.

As used herein, the terms "*Sclerotinia* Stem Rot," "SSR" or "white mold" refer to a soilborne disease caused by a fungus *Sclerotinia sclerotiorum*.

As used herein, the term "*Rhizoctonia* Root Rot" refers to a soil borne disease resulting in root rot and stunting of plant growth caused by a fungus *Rhizoctonia solani*.

As used herein, the terms "*Phytophthora* rot" in reference to a plant part, such as *Phytophthora* seed rot, *Phytophthora* stem rot or *Phytophthora* root rot, refers to a disease caused by a *Phytophthora* fungus.

As used herein, the term "damping-off" refers to a fungal disease in the soil causing seedlings to wilt and die, such as caused by *Pythium ultimum*.

As used herein, the terms "*Pythium* rot" in reference to a plant part, such as a *Pythium* seed rot, *Pythium* stem rot or *Pythium* root rot or *Pythium* seed decay, refers to a disease caused by a fungus *Pythium ultimum*.

As used herein, the terms "*Phomopsis* seed rot" refers to a disease caused by seed-borne fungi, *Phomopsis longicolla*, *Diaporthe phaseolorum* var. *sojae*, and *D. phaseolorum* var. *caulivora*.

As used herein, the term "powdery mildew" refers to fungal growth that appears as a white fuzzy coating on the upper leaves.

As used herein, the term "seedling blight" refers to a disease causing weakened or killed seedlings.

As used herein, the term "mottling" refers to a discoloration of a plant part, such as seed mottling, which is not fungal in origin. Mottling of soybean seed is caused by viruses such as Bean Pod Mottle Virus (BPMV) and Soybean Mosaic Virus (SMV).

As used herein, the term "Bean pod mottle virus" and "BPMV" refers to a virus with small isometric particles and a single-stranded RNA genome that is beetle-transmitted, such as Leaf-feeding beetles (Coleoptera) belonging to *Cerotoma trifurcata, Colaspis brunnea, C. lata, Diabrotica balteata, D. undecimpunctata howardi, Epicauta vittata*, and *Epilachna varivestis*, to soybean and causes a mottling of soybean leaves.

As used herein, the term "Soybean Mosaic Virus" and "SMV" refers to a flexuous rod consisting of positive-sense, single-stranded RNA infected cultivars are slightly stunted with fewer pods that are sometimes dwarfed and flattened, without hairs, and without seeds. At least 32 aphid species, belonging to at least 15 different genera, transmit SMV in a nonpersistent manner.

As used herein, the term "Tobacco ringspot virus" and "TRSV" refers to a bud blight causing nepovirus group of plant viruses with two single-stranded positive sense polyadenylated RNA molecules transmitted by nymphs of *Thrips tabaci*.

As used herein, the term "bacterial pustule" refers to an undesired physical condition, primarily of leaves and pods as the result of an infection, primarily a disease of leaves and pods of a plant [caused by *Xanthomonas campestris* pv. *Glycinea*.

As used herein, the term "bacterial blight" refers to a disease caused by bacteria, such as *Pseudomonas savastonoi* pv. *Glycinea*.

As used herein, the terms "rust" or "soybean rust" or "Leaf Rust" or "Asian soybean rust" refer to a fungal disease, such as that caused by fungi such as *Phakopsora pachyrhizi*.

As used herein, the terms "*Bacillus thuringiensis*" and "Bt" in reference to a toxin refers to insecticidal compounds, such as crystals and proteins, naturally produced by a *Bacillus thuringiensis* bacterium and modified by man for agricultural use.

As used herein, the term "host" refers to any organism (animal or plant) fed upon by a parasite or parasitoid. As used herein, when insects or nematodes feed upon plants they are considered parasites of those plants, and the plants are then referred to as "host plants."

As used herein, the term "plant" is used in it broadest sense. It includes, but is not limited to, any species of woody, ornamental or decorative, crop or cereal, fruit or vegetable, fruit plant or vegetable plant, flower or tree, macroalga or microalga, phytoplankton and photosynthetic algae (e.g., green algae *Chlamydomonas reinhardtii*). A plant also refers to a unicellular plant (e.g. microalga) and a plurality of plant cells that are largely differentiated into a colony (e.g. volvox) or a structure that is present at any stage of a plant's development. Such structures include, but are not limited to, a fruit, a seed, a shoot, a stem, a leaf, a flower petal, etc.

As used herein, the term "soybean plant" refers to a legume plant of the family Fabaceae, herein used in its broadest sense and includes but is not limited to any species of soybean, for example, a *Glycine* species. A soybean plant may be a *Glycine max*, such as a cultivated soybean plant, a *Glycine soia* [Sieb. & Zucc.], such as a wild form of soybean, and a *Glycine gracilis* Skvortz, such as a weedy form of soybean. The present invention is not meant to limit the type of soybean plant. Indeed numerous varieties of aphid resistant soybean plants are contemplated. In some embodiments, an aphid resistant soybean plant provides human food-grade soybeans, such as for soymilk, soynuts, whole soybeans, miso, tofu (such as soybean curd), tempeh, soy sauce (such as shoyu, tamari and teriyaki sauce), soybean oil, margarine, salad oil, and the like. In some embodiments, a human food-grade aphid resistant soybean provides pharmaceutical products, such as for cancer prevention, for example, providing genistein.

As used herein, the term "soybean" refers to a seed of a soybean plant.

As used herein, the term "seed" refers to a fertilized and ripened ovule of a plant, consisting of an embryo and a casing, such as a bean and a soybean, for example, a soybean is a seed.

As used herein, the term "pod" refers to a seed of a soybean plant.

As used herein, the term "hybrid" in reference to a seed or plant is produced as the result of controlled cross-pollination as opposed to a non-hybrid seed produced as the result of natural pollination, as in a "hybrid soybean seed" produced by breeding methods of the present invention.

The terms "leaf" and "leaves" refer to a usually flat, green structure attached to a stem or branch of a plant wherein photosynthesis and transpiration take place.

The term "stem" refers to a main ascending axis of a plant.

The term "node" refers to the joint of a stem and the region of attachment of leaves on a stem.

As used herein, the term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, and a cell. In some embodiments of the present invention transgenic plants are crop plants.

As used herein, the terms "crop" and "crop plant" is used in its broadest sense. The term includes, but is not limited to, any species of plant or alga edible by humans or used as a feed for animals or fish or marine animals, or consumed by humans, or used by humans (natural pesticides), or viewed by humans (flowers) or any plant or alga used in industry or commerce or education.

As used herein, the term "host plant resistance" refers to any one of the preferred methods for minimizing the damage caused by aphids, insects, pests, bacteria, virus, fungi and the like.

As used herein, the terms "resistant" and "resistance" refer to aphid resistance, arthropod resistance, nematode resistance, such as resistance to a soybean cyst nematode pathogen resistance or disease resistance, such as resistance to Seed Mottling caused by viruses, such as Bean Pod Mottle Virus (BPMV) and Soybean Mosaic Virus (SMV), Sudden Death Syndrome (SDS) caused by a fungus *Fusarium solani*, bacterial pustule caused by *Xanthomonas campestris* pv. *Glycines*, etc., fungus resistance, such as soybean rust resistance, and the like.

As used herein, the term "increasing resistance" refers to increasing the ability of a host plant to repel an insect, such as an aphid, nematode, etc., pathogen, fungus, virus, disease, and the like, including by decreasing the physical impact on or damage to the plant of the particular insect, pathogen, disease, and/or nematode attack on a host plant, such as reducing the feeding activity of an aphid, reducing the feeding activity of an insect, reducing the feeding activity of an insect larvae, reducing the number of parasitic nematodes on a plant, reducing the number of parasitic nematodes on a plant, reducing egg laying activity of an insect, reducing the symptoms of infection such as stem rot, root rot, seed mottling, and the like. Increasing resistance also refers to increasing the ability of the host plant to diminished and/or entirely avoid infestation and damage by an aphid, an insect, a bacterium, a fungi, a virus, and a parasitic organism, for example, increasing soybean cyst nematode resistance in a soybean line see, U.S. Pat. No. 6,096,944, herein incorporated by reference, an infection, a disease, a fungus, and the like.

As used herein, the terms "Soybean Cyst Nematode" or "SCN" refer to small roundworms, such as *Heterodera glycines*, that cause root damage and subsequent above-ground disease symptoms to soybeans. At least sixteen physiological races of the SCN have been identified.

As used herein, the term "resistance" in reference to a plant, means a situation wherein insects and/or pathogens are prevented and/or inhibited from causing plant damage and/or diseases and the associated disease symptoms, or alternatively, some or all of the disease symptoms caused by the pathogen are minimized or lessened. This includes but is not limited to the ability of a host to prevent aphid and/or nematode reproduction.

As used herein, the terms "resistant" and "resistance" in reference to insect resistance, refers to aphid resistance or arthropod resistance.

As used herein, the terms "aphid resistant" and "aphid resistance" refers to a capacity of a host plant to prevent and/or reduce the ability of an aphid to damage a host plant, such as reducing feeding, reducing development and the like, when an aphid is in contact with an aphid resistant plant.

As used herein, the term "antibiosis" "antibiosis resistance" and "antibiosis resistance toxicity" in relation to aphid resistance refers to a trait for preventing the aphids from reproducing on plants, for example, as shown in a no-choice study of the present invention, see, EXAMPLE 5. In some embodiments, aphid resistance in a cultivar is indicated by antibiosis resistance preventing the aphids from reproducing on the plants in a no-choice study as compared to a non-resistant cultivar. Examples of soybean cultivars of the present invention showing antibiosis resistance are PI 567541B and PI 567598B. Antibiosis further refers to adverse effects on an insect's life history after a resistant host plant has been used for food (for example, in Painter, Insect Resistance in Crop Plants, Macmillan, N.Y. (1951)).

As used herein, the term "toxin" refers to any substance (usually a protein or conjugated protein) that is detrimental (i.e., poisonous) to cells and/or organisms, in particular an insect organism, i.e. an aphid insect as in an insecticidal substance. In particularly preferred embodiments, the term refers to extracellular toxins and intracellular toxins produced by various plant species, including, but not limited to a soybean plant toxin that provides toxicity activity toward members of the genus *Glycine*. However, it is not intended that the present invention be limited to any particular toxin or plant species. Indeed, it is intended that the term encompass toxins produced by any organism. In one embodiment, an aphid toxin results in the death of an aphid. In one embodiment, an insecticidal protein results in the death of an insect.

As used herein, the terms "antixenosis" and "antixenosis resistance" in relation to aphid resistance refer to a trait for nonpreference of insects for a host plant (for example, Kogan and Ortman, (1978) Bull. Entomol. Soc. Am. 24:175-176), for example, "repellency to aphids" and "aphid repellent" in reference to soybean cultivars of the present invention demonstrating antixenosis resistance are PI 567543C and PI 567597C.

As used herein, the term "repellent" such as an "insect repellent" and an "aphid repellent" refers to a substance, such as a protein, that will ward off and/or keep away and insect, for example, an aphid, as to "repel" as in "repelling an aphid."

As used herein, the term "agronomic trait" and "economically significant trait" refers to any selected trait that increases the commercial value of a plant part, for example, a preferred oil content, protein content, seed protein content, seed fatty acid content, seed size, seed color, hilium color, seed coat thickness, seed sugar content, seed free amino acid content, seed germination rate, seed texture, seed fiber content, seed Vitamin E content, seed isoflavone content, seed phytate content, seed phytosterol content, seed isoflavone content, lecithin content, food-grade quality, hilium color, seed yield, plant type, plant height, lodging, shatter, herbicide resistance, disease resistance, insect resistance, nematode resistance, drought tolerance, drought resistance, water tolerance, water resistance, temperature tolerance, such as cold weather resistance, hot weather resistance, and the like, growth habit, maturity group, field tolerance, and growth in a hardiness zone.

As used herein, the term "fatty acid" refers to a chemical unit occurring either as a single molecule or a molecule of at least 2 or more combined fatty acid units, wherein a fatty acid unit comprises any number of carbon (C), hydrogen (H), and oxygen (O) atoms arranged as a carbon chain skeleton with a carboxyl group (—COOH) at one end. A fatty acid may be a saturated fatty acid or an unsaturated fatty acid. Examples of fatty acids found in soybeans include but are not limited to palmitic, stearic, oleic, linoleic, and linolenic.

As used herein, the terms "saturated fatty acid," "SFAs," "hydrogenated fatty acid" refer to fatty acid molecules or chains of fatty acid molecules without double bonds between the carbon atoms for example, palmitic acid.

As used herein, the term "monounsaturated fatty acids" "MUFAs" refers to a fatty acid molecule with no more than one double bond, for example, oleic acid.

As used herein, the term "polyunsaturated fatty acids" "PUFAs" refers to a fatty acid molecule having more than one double bond, for example, linoleic acid, and linolenic acid found in soybean oil, wherein linolenic acid is an omega-3 polyunsaturated fatty acid that under certain conditions causes soybean oil to become rancid.

As used herein, the term "lecithin" refers to a naturally occurring emulsifier extracted from crude soybean oil.

As used herein, the terms "isoflavone" and "isoflavonoid" refer to a polyphenol molecule or phytoestrogen molecule or estrogen-like molecule found in soybeans, for example, genistein (genistin) a 4',5,7-trihydroxy-isoflavone or a 5,7-dihydroxy-3-(4-hydroxyphenyl)-4-benzopyrone of molecular formula C15-H10-O5 and CAS Registry Number 446-72-0; daidzein (daidzin) 4',7-dihydroxy-(8CI) Isoflavone or 4',7-dihydroxyisoflavone of molecular formula C15-H10-O4 and CAS Registry Number 486-66-8; glycinin of CAS Registry Number 9007-93-6; and glycitein a 7-hydroxy-3-(4-hydroxyphenyl)-6-methoxy-4H-1-benzopyran-4-one of molecular formula C16-H12-05 and CAS Registry Number 40957-83-3.

As used herein, the term "shatter" in reference to shattering refers to a percentage of open pods determined at the time of harvest.

As used herein, the term "lodging" refers to measurement of soybean plants leaning or having fallen or laying on the ground at harvest.

As used herein, the term "growth habit" refers to indeterminate growth habit or determinate growth habit of a soybean plant, in particular, to a growth habit of a variety of soybean plant. For example, indeterminate soybean plant varieties are adapted to maturity group IV and earlier (northern U.S.) have overlapping vegetative and reproductive growth periods. On the other hand, determinate soybean plant varieties with a determinate growth habit are adapted to maturity group V and later (southern U.S.) having distinct vegetative and reproductive development periods.

As used herein, the term "plant type" refers to a physical characteristic of a plant ranging from highly branching types to thin-line types that produce a single main stem.

As used herein, the term "subgenus" in reference to a soybean plant refers to one or more of a "soja" and a "soia," a "max" and a "glycine," wherein a soja and a soia refer to a wild-type soybean plant and a reseeding soybean plant while max and glycine refer to a cultivated plant.

As used herein, the term "soybean maturity group" refers to an industry division of groups of varieties based on the zones in which the varieties are adapted. Soybean maturity groups range from 000-X, wherein 000 represents the earliest and X the latest. Plants adapted to northern day-lengths are classified as early-maturing; those adapted to the southern regions are classified as late-maturing. Maturity groups may include very long day length varieties (000, 00, 0) and extend to very short day length varieties (VII, VII, IX, X). For example, maturity group I soybean cultivars are typically grown in southern Minnesota, whereas maturity group IV soybean cultivars are typically grown in southern Illinois.

As used herein, the term "early maturing" or "early maturity group" in reference to a variety, line or cultivar of a soybean plant refers to soybean plants assigned to a maturity group ranging from 000 to III.

As used herein, the term "early season" or early season variety" in reference to a U.S. variety refers to a variety, line or cultivar of a soybean plant assigned to a maturity group ranging from 000 to IV.

As used herein, the term "relative maturity" when used in reference to a soybean plant maturity group subdivides a maturity group into tenths and provides a more precise maturity assignment, for example, a relative maturity of 3.3 is assigned to a later maturing early maturity group III soybean cultivar than a 3.0 soybean cultivar. The number following the decimal point refers to the relative earliness or lateness within each maturity group, for example, a 3.0 is an early group III variety, while a 3.9 is a late group III variety.

As used herein, the term "line" refers to a nursery term to describe a group of individuals from similar parentage with similar traits; for example, E98076 is a soybean line developed at Michigan State University from the cross DSC Dairyland 217×Northrup King S19-90 and lines E06906, E06902, E06907, E06901, and E06904 are soybean lines developed at Michigan State University from crossing Titan×PI 567598B.

As used herein, the term "cultivar" refers to an unvarying variety of plant propagated by man using selective hybridization and maintained by vegetative propagation or by inbred seed.

As used herein, the term "soybean cultivar" is used in its broadest sense and includes but is not limited to any species of soybean that is cultivated by man.

As used herein, the term "cultivated" in reference to a plant includes any plant or plant part grown and maintained by man for use in food compositions or in nonfood compositions.

As used herein, the term "group" in reference to a plant refers to an artificial category between species and cultivar used to designate a collection of cultivars with similar parentage.

As used herein, the terms "variety" and "varietas" and "var" refer to a rank of taxa below subspecies but above forma for example a plant which retains most of the characteristics of the species, but differs in some way such as seed oil content, seed color, seed size, insect resistance, soybean aphid resistance, and the like.

As used herein, the terms "F-generation" and "filial generation" refers to any of the consecutive generations of cells, tissues or organisms after a biparental cross. The generation resulting from a mating of the a biparental cross (i.e. parents) is the first filial generation (designated as "F1" and "$F_1$") in reference to a seed and it's plant, while that resulting from crossing of F1 individuals is the second filial generation (designated as "F2" or "$F_2$") in reference to a seed and it's plant. For example, an F2 seed and a resulting plant are produced by self-pollination of F1, while later F generations are produced from self-pollination of the immediate prior generation.

As used herein, the terms "plant introductions" and "PI" refers to a plant accession number that can be assigned by the USDA Plant Introduction Office, for example, PI 567597C; PI 567543C; PI 567598B; and PI 567541B.

As used herein, the terms "germplasm" refers to any genetic material of plants, animals or other organisms containing functional units of heredity in other words germplasm comprises nucleic acid molecules.

As used herein, the term "germplasm" in reference to "aphid resistant germplasm" and "aphid resistance germplasm" refers to and encompasses hereditary material that provides resistance to aphids, in particular resistance to soybean aphids.

As used herein, the term "elite germplasm" in reference to a soybean cultivar or line refers to soybean plant hereditary material of proven genetic superiority, for example, a commercial cultivar of a soybean plant, such as a "Round-up Ready™" soybean plant, a soybean plant having a desired agronomic trait, such as lodging, oil content, nematode resistance, et cetera, and for the purposes of the present inventions, elite germplasm includes aphid resistant germplasm of the present inventions.

As used herein, the term "elite plant," "elite soybean plant," "elite soybean plant line," or "elite soybean plant cultivar" refers to any plant, plant line or plant cultivar, respectively, that has resulted from breeding and selection for superior agronomic performance. For example, elite soybean cultivar and elite soybean germplasm refer to isolated soybean cultivars comprising a transgene that provide resistance to herbicides, nematodes, fungi, or an agronomic trait including but not limited to PI257345 and its progenyS1346, PI71506, Hutcheson, Resnik, Lincoln, Richland, Patoka, PI 81041, Illini, PI 54610, PI 88788, Mukden, Palmetto, Haberlandt No. 171, PI 257345, PI 71506, Lincoln, Mandarin (Ottawa), PI 90763, CNS, PI 209332, Richland, Tokyo, S-100, Minsoy, Ogden, Noir 1, A.K. (Harrow), Archer, Dunfield, Evans, Mukden, Clark, Jackson, Harosoy, Illini, Essex, Roanoke, PI 88788, Peking, Asgrow AG4201, Asgrow AG3703, Croplan Genetics RC4432, FFR RT446, HARTZ™ variety H4994, HARTZ™ variety H5218, HARTZ™ variety H5350, HARTZ™ variety H5545, HARTZ™ variety H5050, HARTZ™ variety H5454, HARTZ™ variety H5233, HARTZ™ variety H5488, HARTZ™ variety HLA572, HARTZ™ variety H6200, HARTZ™ varietyH6104, HARTZ™ variety H6255, HARTZ™ variety H6586, HARTZ™ varietyH6191, HARTZ™ variety H7440, HARTZ™ variety H4452 Roundup Ready™, HARTZ™ variety H4994 Roundup Ready™, HARTZ™ varietyH4988 Roundup Ready™, HARTZ™ variety H5000 Roundup Ready™, HARTZ™ varietyH5147 Roundup Ready™, HARTZ™ variety H5247 Roundup Ready™, HARTZ™ variety H5350 Roundup Ready™, HARTZ™ variety H5545 Roundup Ready™, HARTZ™ variety H5855 Roundup Ready™, HARTZ™ variety H5088 Roundup Ready™, HARTZ™ variety H5164 Roundup Ready™, HARTZ™ variety H5361 Roundup Ready™, HARTZ™ variety H5566 Roundup Ready™, HARTZ™ variety H5181 Roundup Ready™, HARTZ™ varietyH5889 Roundup Ready™, HARTZ™ variety H5999 Roundup Ready™, HARTZ™ variety H16013 Roundup Ready™, HARTZ™ variety H6255 Roundup Ready™, HARTZ™ variety H6454 Roundup Ready™, HARTZ™ varietyH6686 Roundup Ready™, HARTZ™ variety H7152 Roundup Ready™, HARTZ™ variety H7550 Roundup Ready™, HARTZ™ variety H8001 Roundup Ready™ (HARTZ SEED, Stuttgart, Ark., USA); A0868, AG0901, A1553, A1900, AG1901, A1923, A2069, AG2101, AG2201, A2247, AG2301, A2304, A2396, AG2401, AG2501, A2506, A2553, AG2701, AG2702, AG2703, A2704, A2833, A2869, AG2901, AG2902, AG2905, AG3001, AG3002, A3204, A3237, A3244, AG3301, AG3302, A3404, A3469, AG3502, AG3503, A3559, AG3601, AG3701, AG3704, AG3750, A3834, AG3901, A3904, A4045 AG4301, A4341, AG4401, AG4501, AG4601, AG4602, A4604, AG4702, AG4901, A4922, AG5401, A5547, AG5602, A5704, AG5801, AG5901, A5944, A5959, AG6101, AJW2600COR, FPG26932, QR4459 and QP4544 (Asgrow Seeds, Des Moines, Iowa, USA); DKB26-52, DKB28-51, DKB32-52, DKB35-51 and DeKalb variety CX445 (DeKalb, Ill., USA); 91B91, 92B24, 92B37, 92B63, 92B71, 92B74, 92B75, 92B91, 93B01, 93B11, 93B26, 93B34, 93B35, 93B41, 93B45, 93B51, 93B53, 93B66, 93B81, 93B82, 93B84, 94B01, 94B32, 94B53, 95B71, 95B95, 9306, 9294, and 9344 (Pioneer Hi-bred International, Johnstonville, Iowa, USA), A2704-12, A2704-21, A5547-35 (Aventis CropScience), A5547-127, GU262, W62, W98, (Bayer CropScience (Aventis CropScience (AgrEvo))), G94-1, G94-19, G168 (DuPont Canada Agricultural Products), GTS 40-3-2 (Monsanto Company), OT96-15 (Agriculture & Agri-Food Canada), Maple Glen, PI361088B, Ohio FG1, Agracola Farms AF271, Burtch Seed BBF44, H.A.P.I. Ohio GL2930, LG Seed EX230FG, Wellman WFG268, Line Trelay 230 (comprising *Phytophthora* resistance germplasm), Trelay 271 (comprising *Phytophthora* resistance germplasm), and the like. For the purposes of the present inventions, an elite soybean plant also refers to plants related to accessions PI567598B, PI567543C, PI567541B, and PI567597C comprising aphid resistant germplasm of the present inventions.

As used herein, the term "hybrid" refers to a seed and a plant produced as the result of controlled pollination as opposed to a seed and a plant produced as the result of natural pollination.

As used herein, the term "trait" refers to an observable and/or measurable characteristics of an organism, such as a trait of a plant, for example, resistance to a soybean aphid, tolerance to an herbicide, an agronomic trait, insect, and microbe.

As used herein, the terms "marker" and "DNA marker" and "molecular marker" in reference to a "selectable marker" refers to a physiological or morphological trait which may be determined as marker for its own selection or for selection of other traits closely linked to that marker, for example, a gene or trait that associates with aphid resistance, such as a marker, such as a DNA marker including but not limited to simple sequence repeat (SSR), single nucleotide polymorphism analysis (SNP), random amplified polymorphic DNA analysis (RAPID), amplified fragment length polymorphism analysis (AFLP), and the like that will link phenotype information, such as aphid resistance to a QTL locus, to provide a genomic map, for example a fingerprint map, and chromosome location and/or map. Examples of SSR markers include but are not limited to "Satt" markers.

As used herein, "Satt" markers refer to forward and reverse PCR primers used for amplifying a genomic marker fragment, in particular for identifying a "linkage group."

As used herein, the term "linkage group" refers to a group of two or more genetically or physically mapped loci with observed linkage to a trait, for example, one or more of a SSR, SNP, AFLP, and RAPD marker of the present invention that may map to aphid resistant germplasm. Examples of soybean linkages groups that are associated with aphid resistant germplasm comprise, for example, J, B2, D1a, D1b and K.

As used herein, the term "selection" as used herein refers to the process of determining the relative aphid resistance of a soybean cultivar.

As used herein, the term "introgress" and "introgressing" refers to incorporating a genetic substance, such as germplasm, loci, allele, gene, DNA, and the like for introducing a trait into an organism, such as a plant, a soybean cultivar and the like, for example, incorporating aphid resistant germplasm into a previously aphid susceptible plant variety. Introgression may refer to a breeding method for a incorporating a genetic trait, such as aphid resistance, including compositions and methods for using QTL, DNA markers including but not limited to simple sequence repeat (SSR), single nucleotide polymorphism analysis (SNP), random amplified polymorphic DNA (RAPD), amplified fragment length polymorphism analysis (AFLP), DNA fingerprinting, and the like for incorporating aphid resistant germplasm into a formerly aphid-susceptible plant variety.

As used herein, the terms "quantitative trait locus" and "QTL" refer to a genomic region including a gene underlying a trait on which many genes act, in other words a genetic locus that affects a quantitative trait, for example, a QTL is associated with soybean cyst nematode resistance as shown herein and in U.S. Pat. No. 6,538,175, herein incorporated by reference.

As used herein, the term "QTL" in relation to a linkage, such as "QTL J aphid resistant germplasm and the like" refers to a polymorphic location of a banding pattern of a marker unique to the soybean plants showing a specific phenotypic trait, such as an aphid resistant phenotype, and other phenotypes as described herein.

As used herein, the terms "associated region gene" or "ARG" in reference to a mapped QTL refers to the actual gene controlling or influencing a phenotype, in other words the "true QTL"

As used herein, the terms "simple sequence repeat" and "SSR" refer to short, tandem repeat nucleotide sequences that are useful as genetic markers, for example, microsatellite DNA is a highly polymorphic DNA marker comprised of mononucleotides, dinucleotides, trinucleotides or tetranucleotides that are repeated in tandem arrays and distributed throughout the genome, such as CA (alternatively GT) dinucleotide repeats.

As used herein, the terms "single nucleotide polymorphism" and "SNP" refer to a single base difference between two DNA sequences.

As used herein, the terms "random amplified polymorphic DNA" and "RAPD" refer to a common technique for amplifying anonymous stretches of DNA using PCR with arbitrary primers, for example, using random PCR primers used to amplify genomic DNA to provide a pattern of bands, such that one pattern of bands may be different between individuals in a population, such as between aphid resistant and aphid susceptible plants or show germplasm differences between closely related plants.

As used herein, the terms "restriction fragment length polymorphism" and "RFLP" refer to genetic variation between individuals such that DNA fragment sizes resulting from a difference in DNA sequence that affects the recognition sequence for restriction enzymes when cut by specific restriction enzymes. When a particular enzyme digests DNA the fragment sizes will differ depending on the presence or absence of the proper recognition sequence for the enzyme. Polymorphic sequences that result in RFLPs are used as markers on both physical maps and genetic linkage maps. RFLPs can be caused by a change in at least one nucleotide at a cutting site.

As used herein, the terms "amplified fragment length polymorphism" and "AFLP" refer to a highly sensitive method for detecting polymorphisms in DNA. Following restriction enzyme digestion of DNA, a subset of DNA fragments is selected for PCR amplification and visualization.

As used herein, the term "DNA fingerprinting" refers to techniques for uniquely identifying an individual among a population based on one's DNA. This type of method of isolating and visualizing sequences of DNA may show a unique pattern of DNA fragments revealed by Southern hybridization or by a polymerase chain reaction (PCR) analysis.

As used herein, the term "polymerase chain reaction" and "PCR" refer to the method of K. B. Mullis (U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the pre-dominant sequences (in terms of concentration) in the mixture, they are said to be "PCR amplified."

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term plant cell "compartments or organelles" is used in its broadest sense. As used herein, the term includes but is not limited to, the endoplasmic reticulum, Golgi apparatus, trans Golgi network, plastids, sarcoplasmic reticulum, glyoxysomes, mitochondrial, chloroplast, thylakoid membranes and nuclear membranes, and the like.

As used herein, the term "gene" refers to a nucleic acid (e.g., DNA or RNA) sequence that comprises coding sequences necessary for the production of RNA, or a polypeptide or its precursor (e.g., proinsulin). A functional polypeptide can be encoded by a full-length coding sequence or by any portion of the coding sequence as long as the desired activity or functional properties (e.g., enzymatic activity, ligand binding, signal transduction, etc.) of the polypeptide are retained.

As used herein, the term "portion" when used in reference to a gene refers to fragments of that gene. The fragments may range in size from a few nucleotides to the entire gene sequence minus one nucleotide.

As used herein, the term "a nucleotide comprising at least a portion of a gene" may comprise fragments of the gene or the entire gene.

As used herein, the term "gene" encompasses the coding regions of a structural gene and includes sequences located adjacent to the coding region on both the 5' and 3' ends for a distance of about 1 kb on either end such that the gene corresponds to the length of the full-length mRNA.

As used herein, the terms "allele" and "alleles" refer to each version of a gene for a same locus that has more than one sequence. For example, there are multiple alleles for eye color at the same locus.

As used herein, the terms "recessive," "recessive gene," and "recessive phenotype" refers to an allele that has a phenotype when two alleles for a certain locus are the same as in "homozygous" or as in "homozygote" and then partially or fully loses that phenotype when paired with a more dominant allele as when two alleles for a certain locus are different as in "heterozygous" or in "heterozygote."

As used herein, the terms "dominant," "dominant," and "dominant phenotype" refers to an allele that has an effect to suppress the expression of the other allele in a heterozygous (having one dominant and one recessive allele) condition.

As used herein, the term "heterologous" when used in reference to a gene or nucleic acid refers to a gene that has been manipulated in some way. For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Examples of a heterologous gene includes a gene encoding an insecticidal protein, an herbicide resistant protein, or for providing an agronomic trait. Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

As used herein, the term "nucleic acid sequence," "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

As used herein, the term "cDNA" refers to a nucleotide copy of the "messenger RNA" or "mRNA" for a gene. In some embodiments, cDNA is derived from the mRNA. In some embodiments, cDNA is derived from genomic sequences.

As used herein, the term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the term "polynucleotide" refers to refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

As used herein, the term "an oligonucleotide having a nucleotide sequence encoding a gene" or "a nucleic acid sequence encoding" a specified polypeptide refers to a nucleic acid sequence comprising the coding region of a gene or in other words the nucleic acid sequence that encodes a gene product. The coding region may be present either in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers, exogenous promoters, splice junctions, intervening sequences, polyadenylation signals, etc. or a combination of both endogenous and exogenous control elements.

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the terms "in operable combination" and "in operable order" and "operably linked" refer to the linkage of nucleic acid sequences in such a manner that a nucleic acid molecule capable of directing the transcription of a given gene and/or the synthesis of a desired protein molecule is produced. As used herein, the term also refers to the linkage of amino acid sequences in such a manner so that a functional protein is produced.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, (1987), herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al., supra (1987), herein incorporated by reference).

As used herein, the terms "promoter element," "promoter," or "promoter sequence" refer to a DNA sequence that is located at the 5' end (i.e. proceeds) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

As used herein, the term "regulatory region" refers to a gene's 5' transcribed but untranslated regions, located immediately downstream from the promoter and ending just prior to the translational start of the gene.

As used herein, the term "promoter region" refers to the region immediately upstream of the coding region of a DNA polymer, and is typically between about 500 bp and 4 kb in length, and is preferably about 1 to 1.5 kb in length.

Promoters may be "constitutive" or "inducible." As used herein, the term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098, herein incorporated by reference), and ubi3 promoters (see e.g., Garbarino and Belknap, Plant Mol. Biol. 24:119-127 (1994), herein incorporated by reference). Such promoters have been used successfully to direct the expression of heterologous nucleic acid sequences in transformed plant tissue.

In contrast, an "inducible" promoter is one that is capable of directing a level of transcription of an operably linked nucleic acid sequence in the presence of a stimulus (e.g., heat shock, chemicals, light, etc.) that is different from the level of transcription of the operably linked nucleic acid sequence in the absence of the stimulus.

As used herein, the term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, et cetera.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species or from different species).

As used herein, the term "naturally linked" or "naturally located" when used in reference to the relative positions of nucleic acid sequences means that the nucleic acid sequences exist in nature in the relative positions.

As used herein, the term "vector" refers to nucleic acid molecules that transfer DNA segment(s). Transfer can be into a cell, cell-to-cell, etc.

As used herein, the term "vehicle" is sometimes used interchangeably with "vector."

As used herein, the term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment), *Agrobacterium* infection, and the like.

As used herein, the term "stable transfection" or "stably transfected" refers to the introduction and integration of foreign DNA into the genome of the transfected cell. As used herein, the term "stable transfectant" refers to a cell that has stably integrated foreign DNA into the genomic DNA.

As used herein, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes.

As used herein, the term "transient transfectant" refers to cells that have taken up foreign DNA but have failed to integrate this DNA.

As used herein, the term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973), herein incorporated by reference) has been modified by several groups to optimize conditions for particular types of cells. The art is well aware of these numerous modifications.

As used herein, the terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, herein incorporated by reference), and are commercially available (e.g., the helium gas-driven microprojectile accelerator (PDS-1000/He, BioRad).

As used herein, the term "transgene" refers to a foreign gene that is placed into an organism by the process of transfection.

As used herein, the term "foreign gene" refers to any nucleic acid (e.g., gene sequence) that is introduced into the genome of an organism by experimental manipulations and may include gene sequences found in that organism so long as the introduced gene does not reside in the same location as does the naturally-occurring gene.

As used herein, the terms "transformants" or "transformed cells" include the primary transformed cell and cultures derived from that cell without regard to the number of transfers. Resulting progeny may not be precisely identical in DNA content, due to deliberate or inadvertent mutations. Mutant progeny that have the same functionality as screened for in the originally transformed cell are included in the definition of transformants.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

As used herein, the terms "modified" or "mutant" when made in reference to a gene or to a gene product refers, respectively, to a gene or to a gene product which displays modifications in sequence and/or functional properties (i.e., altered characteristics) when compared to the wild-type gene or gene product. Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

As used herein, the term "polymorphic locus" refers to a genetic locus present in a population that shows variation between members of the population (i.e., the most common allele has a frequency of less than 0.95). Thus, "polymorphism" refers to the existence of a character in two or more variant forms in a population. A "single nucleotide polymorphism" and "SNP" refers a genetic locus of a single base that may be occupied by one of at least two different nucleotides. In contrast, a "monomorphic locus" refers to a genetic locus at which little or no variations are seen between members of the population (generally taken to be a locus at which the most common allele exceeds a frequency of 0.95 in the gene pool of the population).

As used herein, the terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual*, Cold Spring Harbor Press, NY, pp 9.31-9.58, herein incorporated by reference).

As used herein, the term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. supra, pp 7.39-7.52, (1989), herein incorporated by reference).

As used herein, the terms "protein," "polypeptide," "peptide," "encoded product," "amino acid sequence," are used interchangeably to refer to compounds comprising amino acids joined via peptide bonds and. A "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence.

As used herein, the term "isolated" when used in relation to a nucleic acid such as an isolated DNA molecule or polypeptide, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

As used herein, an "isolated soybean cultivar" refers to a soybean cultivar of the present invention removed from a Soybean Germplasm Collection, isolated or separated, and are at least 0.1% free, preferably 0.01% free, and most preferably 0.002% free from other soybean cultivars in a collection.

As used herein, an "Asian soybean cultivar" refers to a cultivar developed in and originating from soybean plants from an Asian country, for example, China and Japan.

As used herein, the term "portion" when used in reference to a protein (as in "a portion of a given protein") refers to fragments of that protein. The fragments may range in size from four amino acid residues to the entire amino sequence minus one amino acid.

As used herein, the term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, the term "positional cloning" refers to an identification of a gene based on its physical location in the genome.

GENERAL DESCRIPTION OF THE INVENTION

The present invention relates to compositions and methods for providing and using markers of aphid resistant germplasm, particularly for identifying aphid resistance germplasm in soybean plants. Specifically, the inventions related to providing aphid resistant germplasm identified by markers associated with decreased damage from aphid feeding, as well as enhanced tolerance to aphid infestation of soybean plants. More particularly, the invention relates to compositions and methods for using genetic markers in breeding methods for producing plants with increased resistance to aphid damage and tolerance, while retaining and acquiring desired agronomic traits, Furthermore, the invention relates to plants produced by these breeding programs for use in commercial soybean production.

The present invention relates to compositions and methods for providing aphid resistance in plants. More particularly, the invention relates to compositions and methods for using aphid resistant germplasm for breeding soybean aphid resistant soybean plants, including but not limited to cultivars, varieties, lines and methods of breeding the same for commercial use, the breeding methods further involving identifying and using genetic markers for aphid resistant traits.

Advantages of growing and using an aphid resistant soybean plant includes increased effectiveness since the plant produced toxin would be readily available to any aphid feeding anywhere on the resistant plant, increased safety to people by replacing harmful synthetic insecticides with specially bred resistant plants and economical since the plant provides its own constant insect protection. The potential market is substantial because of the recent uncontrolled introduction of aphid pests into the Midwest, which is a major source of soybean products.

At the time the research of the present invention was initiated in 2002, there were no known sources of host plant resistance in the USA. The objectives of this study were to: (i) screen soybean germplasm, originally imported from northern China where soybean aphids are natural pests, where screened plants were publicly available in the USDA Soybean Germplasm Collection but whose soybean aphid resistance was unknown in order to identify sources of germplasm resistance to soybean aphids in early maturity groups; and (ii) determine the resistance type of the identified sources. Unlike the references that describe late maturing aphid resistant soybean plants discussed below the soybean plants of the present invention are an early maturing variety of soybean plant. Further, the source of aphid resistant germplasm of the present invention is originally from soybean plants of China wherein soybean aphids are natural pests. The objective of this study was to identify sources of resistance to soybean aphids from early maturing soybean germplasm and to determine the type of resistance they possess.

Over a two-year period, 2,147 early maturing soybean accessions, obtained from the USDA public soybean germplasm database, from maturity group (MG) 0 to III, originally from northern China, were screened for aphid resistance in the greenhouse and in field cages. The plants were hand-inoculated and aphid populations were evaluated 10 days after inoculation. A damage index (0-100%) was calculated for each accession. After two years of screening and confirmation in choice tests, four accessions from Shandong province, PI 567543C, PI 567597C, PII 567541B, and PI 567598B, in MG III were found to be resistant to the soybean aphid. Two of these accessions, PI 567541B and PI 567598B, possessed antibiosis resistance preventing the aphids from reproducing on the plants in a no-choice study. These resistant sources can be used to develop commercial varieties with aphid resistance for the North Central States of America where soybean varieties of MG 0 to III are cultivated and other areas of the world.

1. Plants

The discovery and isolation of an early maturing aphid resistant soybean cultivar is disclosed herein. Specifically, soybean plant cultivars corresponding to PI 567543C, PI 567597C, PI 567541B, and PI 567598B were isolated from over 2,000 tested soybean cultivars. Further, novel soybean groups, from crosses of another soybean variety with PI 567543C, PI 567597C, PI 567541B, and PI 567598B, are also disclosed. The invention relates to a seed of one or more of a soybean cultivar PI 567543C, PI 567597C, PI 567541B, and PI 567598B, to the plants, i.e. comprising aphid resistant germplasm, of one or more of a soybean PI 567543C, PI 567597C, PI 567541B, and PI 567598B, and to methods for producing a soybean seed and plant produced by crossing any one of a cultivar of PI 567543C, PI 567597C, PI 567541B, and PI 567598B, with itself or another soybean variety, and further to provide offspring comprising the aphid resistant germplasm of the present invention. The invention further relates to an aphid resistant soybean plant and seed from that plant comprising germplasm of any one of a soybean cultivar PI 567543C, PI 567597C, PI 567541B, and PI 567598B. Examples of offspring comprising the aphid resistant germplasm of the present invention include the soybean lines E06906, E06902, E06907, E06901, and E06904.

The methods of the present invention are not limited to the use of any particular plant. Indeed, a variety of plants are contemplated for introducing aphid resistance, including but not limited to soybean, beans, tomato, pepper, cotton, barley, sorgham, sunflowers, rice, corn, wheat, *Brassica*, and flowers.

In some embodiments, aphid resistant germplasm is introgressed into a food-grade soybean plant that includes but is not limited to Ohio FG1, Agracola Farms AF271, Burtch Seed BBF44, H.A.P.I. Ohio GL2930, LG Seed EX230FG, Welhman WFG268, and the like. In some embodiments an aphid resistant a food-grade soybean plant is a specialty soybean plant, for example, provides Edamame soybeans, and the like. In some embodiments, aphid resistant germplasm is introgressed into a soybean plant that provides food for livestock, poultry, cattle and swine, for example, a conventional soybean plant that includes but is not limited to Asgrow AG2905, Pioneer 93B01, and Public Sandusky. In some embodiments a soybean plant provides a non-food product, for example, a fuel additive, such as a diesel fuel additive, soy biodiesel, soybean ink, soy crayons, soybean based wood adhesive, soybean based lubricants, and the like.

2. Vectors

The methods of the present invention contemplate the use of a heterologous gene such as a gene encoding an insect resistant protein, an herbicide resistant protein, a gene for providing a selected agronomic trait, or more than one gene, such as a linkage group for providing a selected agronomic trait (such as aphid resistant germplasm or germplasm comprising an integrated transgene).

Heterologous genes intended for expression in plants are first assembled in expression cassettes comprising a promoter. Methods which are well known to or developed by those skilled in the art may be used to construct expression vectors containing a heterologous gene and appropriate transcriptional and translational control elements. These methods include in vitro recombinant DNA techniques, synthetic techniques, and in vivo genetic recombination. Exemplary techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., herein incorporated by reference).

In general, these vectors comprise a nucleic acid sequence encoding a heterologous gene, or encoding a sequence designed to decrease endogenous gene expression, (as described above) operably linked to a promoter and other regulatory sequences (e.g., enhancers, polyadenylation signals, etc.) required for expression in a plant.

Promoters include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al., Plant Physiol 120:979-992 (1999), herein incorporated by reference); a chemically-inducible promoter from tobacco, Pathogenesis-Related 1 (PR1) (induced by salicylic acid and BTH (benzothiadiazole-7-carbothioic acid S-methyl ester)); a heat shock promoter (U.S. Pat. No. 5,187,267, herein incorporated by reference); a tetracycline-inducible promoter (U.S. Pat. No. 5,057,422, herein incorporated by reference); and seed-specific promoters, such as those for seed storage proteins (e.g., phaseolin, napin, oleosin, and a promoter for soybean beta conglycin (Beachy et al., (1985) EMBO J. 4: 3047-3053, herein incorporated by reference). All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters such as those disclosed herein. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See e.g., Odell et al., Nature 313:810 (1985); Rosenberg et al., Gene, 56:125 (1987); Guerineau et al., Mol. Gen. Genet. 262:141 (1991); Proudfoot, Cell, 64:671 (1991); Sanfacon et al., Genes Dev., 5:141; Mogen et al., Plant Cell, 2:1261 (1990); Munroe et al., Gene, 91:151 (1990); Ballas et al., Nucleic Acids Res. 17:7891 (1989); Joshi et al., Nucleic Acid Res., 15:9627 (1987), all of which are incorporated herein by reference).

In addition, in some embodiments, constructs for expression of the heterologous gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. Intron sequences have been routinely incorporated into plant transformation vectors, typically within the non-translated leader.

In some embodiments of the present invention, a construct for expression of the heterologous nucleic acid sequence of interest also includes a regulator such as a nuclear localization signal (Kalderon et al., Cell 39:499 (1984); Lassner et al., Plant Molecular Biology 17:229 (1991)), a plant translational consensus sequence (Joshi, Nucleic Acids Research 15:6643 (1987)), an intron (Luehrsen and Walbot, Mol. Gen. Genet. 225:81 (1991)), and the like, operably linked to the nucleic acid sequence encoding an heterologous gene.

In preparing the construct comprising the nucleic acid sequence encoding an heterologous gene, or encoding a sequence designed to decrease heterologous gene expression, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, Gene 19: 259 (1982); Bevan et al., Nature 304:184 (1983), all of which are incorporated herein by reference), the bar gene which confers resistance to the herbicide phosphinothricin (White et al., Nucl Acids Res. 18:1062 (1990); Spencer et al., Theor. Appl. Genet. 79:625 (1990), all of which are incorporated herein by reference), the hph gene which confers resistance to the antibiotic hygromycin (Blochlinger and Diggelmann, Mol. Cell.

Biol. 4:2929 (1984), incorporated herein by reference)), and the dhfr gene, which confers resistance to methotrexate (Bourouis et al., EMBO J., 2:1099 (1983), incorporated herein by reference).

In some preferred embodiments, the Ti (T-DNA) plasmid vector is adapted for use in an *Agrobacterium* mediated transfection process (See e.g., U.S. Pat. Nos. 5,981,839; 6,051,757; 5,981,840; 5,824,877; and 4,940,838; all of which are herein incorporated by reference). Construction of recombinant Ti and Ri plasmids in general follows methods typically used with the more common vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The use of T-DNA as a flanking region in a construct for integration into a Ti- or Ri-plasmid has been described in EPO No. 116,718 and PCT Application Nos. WO 84/02913, 02919 and 02920 all of which are herein incorporated by reference). See also Herrera-Estrella, Nature 303:209-213 (1983); Fraley et al., Proc. Natl. Acad. Sci, USA 80:4803-4807 (1983); Horsch et al., Science 223:496-498 (1984); and DeBlock et al., EMBO J. 3:1681-1689 (1984), all of which are herein incorporated by reference).

The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available. In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967 herein incorporated by reference). One of skill in the art knows that homologous recombination may be achieved using targeting vectors that contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known. *Agrobacterium tumefaciens* is a common soil bacterium that causes crown gall disease by transferring some of its DNA to the plant host. The transferred DNA (T-DNA) is stably integrated into the plant genome, where its expression leads to the synthesis of plant hormones and thus to the tumorous growth of the cells. A putative macromolecular complex forms in the process of T-DNA transfer out of the bacterial cell into the plant cell.

In yet other embodiments, the nucleic acids such as those disclosed herein is utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted heterologous polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention, where a heterologous nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278, herein incorporated by reference).

3. Transformation Techniques

Once a nucleic acid sequence encoding an heterologous gene is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See e.g., U.S. Pat. Nos. 5,451,513; 5,545,817; 5,545,818; PCT application WO 95/16783 all of which are incorporated herein by reference). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., PNAS, 87:8526 (1990); Staub and Maliga, Plant Cell, 4:39 (1992), all of which are incorporated herein by reference). The presence of cloning sites between these markers allowed creation of a plastid targeting vector introduction of foreign DNA molecules (Staub and Maliga, EMBO J., 12:601 (1993)). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, PNAS, 90:913 (1993)). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway, Mol. Gen. Genet, 202:179 (1985)). In still other embodiments, the vector is transferred into the plant cell by using polyethylene glycol (Krens et al., Nature, 296:72 (1982); Crossway et al., BioTechniques, 4:320 (1986)); fusion of protoplasts with other entities, either minicells, cells, lysosomes or other fusible lipid-surfaced bodies (Fraley et al., Proc. Natl. Acad. Sci., USA, 79:1859 (1982)); protoplast transformation (EP 0 292 435); direct gene transfer (Paszkowski et al., EMBO J., 3:2717 (1984); Hayashimoto et al., Plant Physiol. 93:857 (1990)).

In still further embodiments, the vector may also be introduced into the plant cells by electroporation. (Fromm, et al., Pro. Natl Acad. Sci. USA 82:5824 (1985); Riggs et al., Proc. Natl. Acad. Sci. USA 83:5602 (1986)). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (e.g., available from Agracetus, Inc., Madison, Wis. and Dupont, Inc., Wilmington, Del.), see e.g., U.S. Pat. No. 4,945,050; and McCabe et al., Biotechnology 6:923 (1988), all of which are incorporated herein by reference). Examples of methods for transforming crop plants are provided for soybean plants in U.S. Pat. No. 5,015,580, herein incorporated by reference, Christou et al., Plant Physiol., 87:671 (1988) (soybean); McCabe et al., Bio/Technology 6:923 (1988) (soybean); and other plants such as Weissinger et al., Annual Rev. Genet. 22:421 (1988); Sanford et al., Particulate Science and Technology, 5:27 (1987) (onion); Svab et al., Proc. Natl. Acad. Sci. USA, 87:8526 (1990) (tobacco chloroplast); Klein et al., Proc. Natl. Acad. Sci. USA, 85:4305 (1988) (maize); Klein et al., Bio/Technology, 6:559 (1988) (maize); Klein et al., Plant Physiol., 91:4404 (1988) (maize); Fromm et al., Bio/Technology, 8:833 (1990); and Gordon-Kamm et al., Plant Cell, 2:603 (1990) (maize); Koziel et al., Biotechnology, 11:194 (1993) (maize); Hill et al., Euphytica, 85:119 (1995) and Koziel et al., Annals of the New York Academy of Sciences 792:164 (1996); Shimamoto et al., Nature 338: 274 (1989) (rice); Christou et al., Biotechnology, 9:957 (1991) (rice); Datta et al., Bio/Technology 8:736 (1990) (rice); European Application EP 0 332 581 (orchardgrass and other Poaceae); Vasil et al., Biotechnology, 11: 1553 (1993) (wheat); Weeks et al., Plant Physiol., 102: 1077 (1993) (wheat); Wan et al., Plant Physiol. 104: 37 (1994) (barley); Jahne et al., Theor. Appl. Genet. 89:525 (1994) (barley); Knudsen and Muller, Planta, 185:330 (1991) (barley); Umbeck et al., Bio/Technology 5: 263 (1987) (cotton); Casas et al., Proc. Natl. Acad. Sci. USA 90:11212 (1993) (sorghum); Somers et al., Bio/Technology 10:1589 (1992) (oat); Torbert et al., Plant Cell Reports, 14:635 (1995) (oat); Weeks et al., Plant Physiol., 102:1077 (1993) (wheat); Chang et al., WO 94/13822 (wheat) and Nehra et al., The Plant Journal, 5:285 (1994) (wheat), all of which are herein incorporated by reference.

In addition to direct transformation, in some embodiments, the vectors comprising a nucleic acid sequence encoding a heterologous gene are transferred using *Agrobacterium*-mediated transformation (Hinchee et al., Biotechnology, 6:915 (1988); Ishida et al., Nature Biotechnology 14:745 (1996), all of which are herein incorporated by reference). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention) can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell, (1987) Science, 237:1176). Species which are susceptible infection by *Agrobacterium* may be transformed in vitro. Transformation methods for producing transgenic soybean plants using *Agrobacterium*-mediated transformation are provided in U.S. Patent Appln. No. 20020157139, U.S. Pat. Nos. 6,384,301, 5,416,011, 5,569, 834, and 5,824,877, all of which are herein incorporated by reference.

4. Regeneration.

After selecting for transformed plant material that can express a heterologous gene encoding a heterologous gene or variant thereof, whole plants are regenerated, for example methods for regenerating transformed soybean plants are provided in U.S. Pat. No. 5,015,580, herein incorporated by reference. Plant regeneration from cultured protoplasts is described in Evans et al., Handbook of Plant Cell Cultures, Vol. 1: (MacMillan Publishing Co. New York, (1983); and Vasil I. R. (ed.), Cell Culture and Somatic Cell Genetics of Plants, Acad. Press, Orlando, Vol. I, (1984) and Vol. III, (1986), herein incorporated by reference. It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

5. Generation of Transgenic Aphid Resistant Soybean Lines

Transgenic lines are established from transgenic plants by tissue culture propagation. The presence of nucleic acid sequences encoding a heterologous gene or mutants or variants thereof in a transgenic plant line may be introgressed into aphid resistant plants for providing transgenic aphid resistant plants using traditional plant breeding techniques. Transgenic lines of aphid resistant soybean cultivars may be utilized for evaluation of aphid resistant activity, insect resistance ratios, phenotype, pathogen resistance and other agronomic traits, such as agronomic shown for transgenic soybean plants in European Patent No. 301,749, herein incorporated by reference, in the presence of an introgressed transgene.

DETAILED DESCRIPTION OF THE INVENTION

The present invention relates to compositions and methods for providing aphid resistant in plants. More particularly, the invention relates to compositions and methods for using aphid resistant germplasm for breeding soybean aphid resistant soybean plants, including but not limited to cultivars, varieties, lines and methods of breeding the same for commercial use, the breeding methods further involving identifying and using genetic markers for aphid resistant traits.

Specifically, this invention discloses novel soybean lines and cultivars including transgenic, hybrid, outcrossed, backcrossed, inbred and self-fertilized progeny comprising soybean aphid resistant soybean germplasm, specifically founder soybean cultivars of Glycine max (L.) Merr. max, designated accessions PI 567543C, PI 567597C, PI 567541B, and PI 567598B and their progeny, such as lines, E06902, E06907, E06901, and E06904 are disclosed. The invention relates to the seeds and plants of novel aphid resistant lines and cultivars, to the groups of plants comprising aphid resistant lines and cultivars and to methods for producing an aphid resistant soybean plant obtained by crossing the founder cultivars (i.e. accessions PI 567543C, PI 567597C, PI 567541B, and PI 567598B) with another soybean variety (preferably elite soybean varieties), including backcrosses with the founder cultivars, backcrosses with the original soybean variety, and further, crosses within and between a filial generation (F), for example, one or more of an F1-F7, including but not limited to inbreeding using self-pollination. The present invention further relates to the generation of a commercially viable aphid resistant early maturing soybean seed and plant produced by the compositions and methods of the present invention. Additionally, the present invention relates to the generation of molecular markers, including SSR and other DNA markers for identifying linkage groups comprising aphid resistant germplasm, for example, sequences for PCR primers used to amplify SSR loci in Soybean, Zhu et al. Genetics 2003 March; 163(3):1123-34, for genes relating to aphid resistance and using molecular marker analysis for identifying and using genes relating to aphid resistance.

In experiments conducted during the course of the present invention, sources and types of resistance to soybean aphid from early maturing soybean germplasm were identified. Over a two-year period, 2,147 soybean accessions from maturity group (MG) 0 to III, originally from northern China, were evaluated for aphid resistance in a greenhouse and in field cages. The plants were hand-inoculated and aphid populations were evaluated 10 days after inoculation. A damage index (0-100%) was calculated for each accession. After two years of evaluation and confirmation in choice tests, four MG III accessions from Shandong province, accessions PI 567543C, PI 567597C, PI 567541B, and PI 567598B, were found to be resistant to the soybean aphid. Two of these accessions, PI 567541B and PI 567598B, possessed antibiosis resistance, preventing the aphids from reproducing on the plants in a no-choice study. Two additional accessions PI 567543C and PI 567597C possessed antixenosis resistance. These resistant sources can be used to develop commercial cultivars with aphid resistance for the North Central States of America and other areas of the world.

In order to develop aphid resistant varieties, sources of germplasm comprising aphid resistance must be identified. Sources of resistance to the soybean aphid are reported in China. In the late 1980's, two highly resistant varieties were found among 181 varieties evaluated (Yi-heng, (1988) Soybean Science. 7(2):167-169; Fan, (1988) Soybean Sci. 7:152; herein incorporated by reference). In 1991, resistance was also reported in soybean germplasm in China (Sun et al., (1991) Soybean Sci. 10 (2):98-103; Gao, et al., (1991) Chin. J Biol. Control 7:95; Sun, et al., 1991, Study on the resistance in wild soybean to soybean mosaic potyvirus. Soybean Science 10:212-216; herein incorporated by reference). The type of resistance, antixenosis or antibiosis, was not indicated in these studies. Antixenosis is nonpreference of insects for a host plant (Kogan and Ortman, (1978) Bull. Entomol. Soc. Am. 24:175-176). Antibiosis includes all adverse effects on an insect's life history after a resistant host plant has been used for food (Painter, 1951, Insect Resistance in Crop Plants, Macmillan). Knowing the type of resistance is important to fully understand and utilize resistant accessions in a breeding program. Hill et al. (Hill et al., (2004) Crop Sci. 44: 98-106) recently reported three lines with resistance to soybean aphid. PI 71506 (MG IV) has antixenosis and the cultivars Dowling (MG VIII) and Jackson (MG VII) are reported to have antibiosis resistance.

In 2002, there were no known sources of host plant resistance to soybean aphid in the United States of America. Hill (Hill et al., (2004) Crop Sci. 44: 98-106) evaluated 1,542 soybean genotypes, mostly current North American soybean cultivars, and found resistance in three North American soybean ancestral lines: Dowling, Jackson, and PI 71506. These resistant genotypes, which belong to MG IV to VIII, are not well adapted to the northern U.S. where soybean aphids are most prevalent. In experiments conducted during the course of the present invention, four resistant accessions (PI 567543C, PI 567597C, PI 567541B, and PI 567598B) belonging to MG III after evaluating 2,147 soybean accessions in MG 0 to III were identified. These primitive Chinese cultivars originated from Shandong province, but their resistance to the soybean aphid has never been reported.

In experiments conducted during the course of the present invention, the aphid resistance germplasm of the original four accessions, PI 567543C, PI 567597C, PI 567541B, and PI 567598B, are incorporated into elite soybean germplasm of soybean plants grown in the U.S. and Canada. In particular, incorporating the aphid resistance germplasm of these accessions into elite soybean germplasm and the progeny of elite soybean germplasm of soybean plants grown in north central regions and southern regions of the United States is contemplated. Incorporating aphid resistance germplasm into elite soybean plants grown in South America, including Brazil and Argentina, Indonesia, China and other countries where soybean plants are grown is also contemplated.

Aphid Resistant Transgenic Soybean Plants

The present invention contemplates providing commercial lines of transgenic aphid resistant soybean plants by introgressing the aphid resistance germplasm of the present invention into commercially established transgenic soybean lines. In addition, introgressing the germplasm comprising a preferred transgene into aphid resistant soybean plants for developing commercial lines of aphid resistant transgenic soybean plants is contemplated.

Numerous cultivars and lines of transgenic soybean plants have been and are being developed as commercial varieties for use by growers and breeders for providing preferred agronomic traits including such traits as a preferred herbicide resistance, a preferred insect resistance, a preferred nematode resistance, a preferred microorganism, such as fungi or bacterial resistance, a preferred soybean seed oil content and the like. Therefore, one contemplated aspect of the present invention is for providing an aphid resistant transgenic plant by introgressing aphid resistant germplasm of the present invention into a transgenic variety. In one embodiment, the germplasm of a transgenic plant comprising an integrated transgene is used for introgressing said transgene into an aphid resistant soybean plant, for example, transgenic plants comprising a transgenes providing one or more of herbicide resistance, insect resistance, nematode resistance, fungal resistance, bacterial resistance, an agronomic trait and the like. Examples of transgenic plants for providing herbicide resistance transgenes include but are not limited to transgenic soybean lines such as lines A2704-12 (U.S. Pat. No. 4,940, 835, herein incorporated by reference), A2704-21, A5547-35 (Aventis CropScience) developed tolerate the use of glufosinate ammonium, the active ingredient in phosphinothricin herbicides (Basta®, Ignite®, Rely®, Liberty®, Harvest®, and Finale®) as a weed control option and lines A5547-127 (Bayer Crop Science (Aventis Crop Science (AgrEvo))) developed for tolerating the use of glufosinate ammonium, the active ingredient in phosphinothricin herbicides (Basta®, Ignite®, Rely®, Liberty®, Harvest®, and Finale®) as a weed control option, GU262, genetically engineered to express tolerance to glufosinate ammonium, the active ingredient in phosphinothricin herbicides (Basta®, Rely®, Finale®, and Liberty®) (Bayer Crop Science (Aventis Crop Science (AgrEvo))) W62, W98 (Bayer Crop Science (Aventis Crop Science (AgrEvo))) genetically engineered to express tolerance to glufosinate ammonium, the active ingredient in phosphinothricin herbicides (Basta®, Rely®, Finale®, and Liberty®); GTS 40-3-2 (Monsanto Company) developed for tolerating glyphosate, the active ingredient in the herbicide Roundup®, as a weed control option by inserting a modified 5-enolpyruvylshikimate-3-phosphate synthase (EPSPS) encoding gene from the soil bacterium *Agrobacterium tumefaciens*, all of which are herein incorporated by reference. Other glyphosate-resistant plants are provided by U.S. Pat. No. 4,940,835, herein incorporated by reference.

As used herein, the terms "Roundup Ready" and "RR" refer to a registered trademark of Monsanto Chemical Company. The present invention contemplates the use of experimental and commercial Roundup Ready tolerant transgenic soybean lines in compositions and methods of the present invention for providing herbicide tolerance to ROUNDUP, glyphosate-isopropylammonium, MON-0573 in aphid resistant plants. In addition, the present invention provides methods for introgressing aphid resistant germplasm into Roundup Ready soybean plants for providing aphid resistant ROUNDUP tolerant soybean plants for experimental use and commercial development. Numerous varieties of Roundup Ready soybean plants are contemplated for use in the present invention, including, but not limited to, Roundup Ready (RR) soybeans for early maturity varieties of soybeans in maturity group I, Mars 618RR, and High Cycle Roundup Ready soybeans in Maturity/Group 0-1.7, 2111RR, 2133RR, 2143RR, 2154RR, 2162RR, 2163RR, 2174RR, 2175RR; GROUP II, Munsee IVRR, Mohegan 624RR, Apache 626RR, Sioux IIRR, Shawnee 527RR, and Shawnee 527RR, High Cycle Roundup Ready soybeans in maturity/group 1.8-2.4 2183RR, 2184RR, 2194RR, 2202RR, 2213RR, 2222RR, 2223RR, 2224RR, 2232RR, 2245RR; GROUP III Jefferson 630RR, Grant IIIRR, Truman 636RR, Kennedy 538RR, Washington IXRR, AG 3702, AG 3902, DPX 3919RR, DPX 3761RR, DPX 3940RR, Asgrow 3906, Delta King 3968, DPL 3861, Progeny 3900, Dyna-Gro 31J39, Mor Soy 3883N; High Cycle Roundup Ready soybeans, maturity/group 2.5-3 Line High Cycle 2274 (further comprising germplasm conferring white mold tolerances, *Phytophthora* tolerance and Brown stem Rot (BSR) resistance), Line High Cycle 2274 (further comprising germplasm conferring excellent *Phytophthora* field tolerance), Line High Cycle 2293 (further comprising germplasm conferring excellent *Phytophthora* tolerance, Soybean Cyst Nematode (SCN) resistant (Race 3, MR14), all of which are herein incorporated by reference. Examples of early season roundup resistant soybean lines for use in the present invention in maturity group III include, but are not limited to, AG 3901, HTS 3600RR, 3902-4 8390 RR, HTS 3600RR, CX 383RR, H 3090RR and maturity group IV Manokin DP, 4344RR, AP 4602RR, DP 4750RR, CX 444cRR, H 4252RR, 8411 RR, 4001-4, CX 414cRR, CX 433RR, AP 4888RR, and AP 4980RR lines.

In some embodiments, aphid resistant germplasm is for introgressing into Roundup Ready soybean lines. In some embodiments, germplasm comprising the Roundup Ready gene is used for introgressing into aphid resistant plants. In some embodiments, the Roundup Ready gene is used for inserting into an aphid resistant soybean plant part so as to provide ROUNDUP tolerant aphid resistant soybean seeds and plants. The present invention contemplates the use of disclosed transgenic plants comprising heterologous transgenes for providing insect resistance, including but not limited to, Bt derived transgenes (e.g., a gene encoding a Coleopteran inhibitory insecticidal crystal protein tIC851 as described in U.S. Patent Application. Nos. 20020103362, 0030229919 and U.S. Pat. No. 6,541,448); genes and their encoded crystal proteins that exhibit insecticidal activity against lepidopteran insects (see, e.g., U.S. Patent Application. No. 20030237111); genes encoding novel crystal Δ-endotoxin proteins which exhibit insecticidal activity against lepidopteran insects (see, e.g., U.S. Pat. No. 6,593,293); genes encoding Δ-endotoxins, mutant endotoxins and endotoxin derived proteins having pesticidal activity against pests of the order Coleoptera as described in U.S. Patent Application. Nos. 20020151709 and 20030177528; genes encoding Δ-endotoxins such as for Cry9 and derived proteins for having pesticidal activity against insect pests, including but not limited to Lepidoptera (see, e.g., U.S. Patent Application. No. 20050138685); Bt genes encoding Δ-endotoxins having pesticidal activity against insect pests (see, e.g., U.S. Patent Application. No. 20040091505, 20050261188, and 20050261483; genes encoding proteins with toxicity to Coleopteran insects (see, e.g., U.S. Pat. No. 5,763,241); genes encoding synthetic insecticidal crystal protein gene derived from Bt (see, e.g., U.S. Pat. Nos. 5,380,831 5,567, 862); Bt genes encoding protease resistant toxins BTS02618Aa or BTS02618Ab (see, e.g., U.S. Pat. Nos. 5,861,543 and 6,143,550) (all references are herein incorporated by reference).

The present invention contemplates the use of transgenic plants comprising a heterologous transgene for providing nematode resistance and pest resistance, in particular Soybean cyst nematode, as described in International patent application nos. 20020144310, 20030005491, 20060095987, WO96/30517, and WO93/19181, and U.S. Pat. Nos. 6,538, 175, and 6,096,944, all of which are herein incorporated by reference in their entireties. In some embodiments, the present invention provides plants comprising transgenes that provide resistance for a variety of diseases and pathogens. The present invention is not limited to any particular resistance gene. Those known and later discovered resistance genes will find use in the present invention (see, e.g., U.S.

Patent Application Nos. 20060059580 and 20060041954; each of which are incorporated by reference in their entireties). Examples of transgenic plants used for providing germplasm providing an agronomic trait, such as a preferred oil content, include but are not limited to lines G94-1, G94-19, G168 (DuPont Canada Agricultural Products). The present invention further contemplates the use of methods and compositions for identifying soybean plants that are tolerant, have improved tolerance or are susceptible to iron deficient growth conditions (see, e.g., U.S. Patent Application Nos. 20060041951 and 20060005276). Providing experimental transgenic aphid resistant soybean plants for identifying any loss of desirable traits by inserting a particular transgene into an aphid resistant soybean plant is also contemplated.

Another aspect of the present invention is to provide aphid resistant transgenic plants by introgressing the aphid resistant germplasm into transgenic soybean plants comprising a transgene (e.g., a transgene providing for preferred agronomic traits and preferred economic traits, preferred herbicide resistance, preferred insect resistance, preferred nematode resistance, preferred microorganism, such as fungi or bacterial resistance).

Maturity Group Identification

QTL region identification for use in breeding methods and developing commercial cultivars of aphid resistant soybean plants of the present inventions. Q QTL mapping study is to map QTLs underlying a trait of interest on a genetic linkage map, which is a linear map showing the relative positions of genetic markers. Therefore, genetic markers and linkage maps are essential for any QTL mapping study. Several types of genetic markers are available in soybean, including classical markers, isozyme markers, restriction fragment length polymorphism (RFLP) markers, random amplified polymorphic DNA (RAPD) markers, amplification fragment length polymorphism (AFLP) markers, simple sequence repeat (SSR) markers, and single nucleotide polymorphism (SNP) markers. The most abundant markers developed for soybean are RFLP markers (Apuya et al. 1988; Keim et al. 1989), SSR markers (Akkaya et al. 1995), AFLP markers (Keim et al. 1997), and SNP markers (Choi et al. 2007). The first soybean molecular linkage map was published in 1990 by Keim et al. (1990a). This map contained 150 RFLP markers and three classical markers. The map was further expanded to include 355 RFLP markers and 16 other types of markers by 1993 (Shoemaker and Olson 1993). By 1999, the map was expanded to have 501 RFLPs markers, 486 SSRs, and 27 markers of other types (Cregan et al. 1999). This map was integrated with two maps developed with two additional mapping populations (Cregan et al. 1999). The integrated map had 689 RFLPs, 606 SSRs, 79 RAPDs, and 47 markers of other types. Using the three mapping populations and two additional mapping populations, a new version of the integrated map was constructed in 2004 (Song et al. 2004). The new integrated map contained 1015 SSRs, 709 RFLPs, 73 RAPDs, and 52 markers of other types, with a total map length of 2523.6 cM (Song et al. 2004). The most recent version of the integrated map was published in 2007 (Choi et al. 2007). This map contains 2,989 markers, including 1141 SNPs, 1014 SSRs, 709 RFLPs, and 125 other types of markers. The map consists of 20 linkage groups with a total map length of 2550.3 cM (Choi et al. 2007). The molecular markers, especially the SSR markers, from the integrated maps have been widely used in QTL mapping studies in soybean (Diers et al. 1992; Keim et al. 1990a; Neto et al. 2007; Wang et al. 2004a; Zhu et al. 2006).

In addition to the integrated linkage maps, several other molecular linkage maps were developed for soybean. A map with over 600 RFLP markers was developed by the DuPont Corporation (Rafalski and Tingey 1993). A map with 132 RFLP markers and 8 other types of markers was developed by Lark et al. (Lark et al. 1993). A map with 650 AFLPs, 165 RFLPs, and 25 RAPDs was developed by Keim et al. (1997). Liu et al. (2000) developed a map containing 100 RFLPs, 62 RAPDs, 42 AFLPs, 33 SSRs, and three other types of markers. Matthews et al. (2001) developed a map with 105 AFLPs, 39 RFLPs, 25 SSRs, 17 RAPDs, and four classical markers. Yamanaka et al. (2001) developed a map with 401 RFLPs, 96 SSRs, and six other types of markers. Wu et al. (2001) constructed a map with 486 AFLPs, 196 RFLPs, 87 SSRs, 18 RAPDs, and five other types of markers. This map and the mapping population have been used in several QTL mapping studies in China (Fu et al. 2007; Wang et al. 2004b, 2004c; Wang et al. 2004d).

Maturity Group Markers.

QTLs for maturity were found in eight consensus regions on six LGs: C1, C2, D1a, I, L, and M (Tables A-G and FIG. 14). The regions 53-66 cM on LG C1, 37-49 cM on LG D1a, 31-36 cM on LG I, 54-68 cM on LG L, and near 18-20 cM on LG M were each found containing QTLs for maturity in two different mapping populations with three or four mapping parents (Tables A-G). The 111-125 cM region on LG C2 was found with five different mapping populations developed from eight mapping parents (Tables A-G). The region 88-96 cM on LG L and the region 32-40 cM on LG M were each found with three mapping populations developed from five or six mapping parents (Table 1).

TABLE A

Consensus regions for Maturity Groups.

| Trait/QTL Maturity | LG[a] | Start position[b] | End position[b] | Mapping parent 1 | Mapping parent 2 | Reference |
|---|---|---|---|---|---|---|
| Pod mat 1-1 | C1 | 53 | 55 | A81356022 | PI 468916 | Keim et al. (1990a) |
| Pod mat 8-5 | C1 | 64 | 66 | Archer | Minsoy | Orf et al. (1999b) |
| Pod mat 8-1 | C2 | 111 | 113 | Archer | Minsoy | Orf et al. (1999b) |
| Pod mat 13-4 | C2 | 111 | 113 | Minsoy | Noir 1 | Specht et al. (2001) |
| Pod mat 14-3 | C2 | 112 | 114 | IA2008 | PI 468916 | Wang et al. (2004a) |
| Pod mat 4-1 | C2 | 117 | 119 | PI 27890 | PI 290136 | Mansur et al. (1996) |
| Pod mat 1-5 | C2 | 123 | 125 | A81356022 | PI 468916 | Keim et al. (1990a) |

TABLE A-continued

Consensus regions for Maturity Groups.

| Trait/QTL Maturity | LG[a] | Start position[b] | End position[b] | Mapping parent 1 | Mapping parent 2 | Reference |
|---|---|---|---|---|---|---|
| Pod mat 1-2 | D1a | 37 | 39 | A81356022 | PI 468916 | Keim et al. (1990a) |
| Pod mat 13-2 | D1a | 47 | 49 | Minsoy | Noir 1 | Specht et al. (2001) |
| Pod mat 12-1 | I | 31 | 33 | Parker | PI 468916 | Yuan et al. (2002) |
| Pod mat 11-1 | I | 34 | 36 | A81356022 | PI 468916 | Yuan et al. (2002) |
| Pod mat 14-1 | L | 54 | 56 | IA2008 | PI 468916 | Wang et al. (2004a) |
| Pod mat 8-4 | L | 66 | 68 | Archer | Minsoy | Orf et al. (1999b) |
| Pod mat 13-6 | L | 88 | 90 | Minsoy | Noir 1 | Specht et al. (2001) |
| Pod mat 4-3 | L | 91 | 93 | PI 27890 | PI 290136 | Mansur et al. (1996) |
| Pod mat 9-2 | L | 94 | 96 | Archer | Noir 1 | Orf et al. (1999b) |
| Pod mat 8-2 | M | 18 | 20 | Archer | Minsoy | Orf et al. (1999b) |
| Pod mat 13-7 | M | 18 | 20 | Minsoy | Noir 1 | Specht et al. (2001) |
| Pod mat 14-4 | M | 32 | 34 | IA2008 | PI 468916 | Wang et al. (2004a) |
| Pod mat 10-2 | M | 33 | 35 | Minsoy | Noir 1 | Orf et al. (1999b) |
| Pod mat 7-1 | M | 38 | 40 | PI 27890 | PI 290136 | Lark et al. (1994) |

Uniform tests are planted in multiple-row plots with three or four replications, and the center rows are harvested for yield and seed quality determinations. Preliminary Tests are multiple-row plots with two replications. Usually 15 to 20 feet of row are planted and 12 to 16 feet harvested, to eliminate end-of-row effects. Coefficients of variability are included with all replicated test data. Discretion is used in including data with high CVs in the regional means. If the CV is greater than 15, participants should include the reason, such as disease or environmental conditions. Lines may be heterogeneous for morphological traits the first year in the Uniform Tests but must be pure lines the second year of testing. It is the responsibility of the breeder to purify heterogeneous lines. Generation ComDosited is the generation after the final single-plant selection, when seeds from plants or rows are composited. Previous Testing is the number of previous years in the same Uniform Test or, in the case of new entries, a reference to the previous year's test, abbreviated to PT IIA for Preliminary Test IIA, for example. Yield is measured after the seeds have been dried to uniform moisture content and is recorded in bushels (60 pounds) per acre. To convert to kilograms/hectare multiply by 67.25. Maturity is the date when 95% of the pods have ripened, as indicated by their mature pod color. Delayed leaf drop and green stems are not considered in assigning maturity. Maturity is expressed as days earlier (−) of later (+) than the average date of the reference variety. To aid in maturity group classification, one earlier (E) and one later (L) check variety are given in the maturity column for each test, or a maturity check from an earlier or later maturity group is included. Current reference and check varieties and the maturity group limits relative to the reference varieties are:

These maturity group ranges are based on long-term means over many locations. When using data from other environments, the interval between reference varieties may vary, and the division between maturity groups should be estimated in proportion to the above figures. Additional check varieties may be included in specific tests such as IA 1022 (SCN) for resistance to the soybean cyst nematode in UT I, or IA3024 as a 1% linolenic check in PTII and PTIII.

Lodging is rated at maturity according to the following scores: 1. Almost all plants erect. 2 All plants leaning slightly or a few plants down. 3. All plants leaning moderately (45 degrees), or 25% to 50% of the plants down. 4. All plants leaning considerably, or 50% to 80% of the plants down. 5. Almost all plants down.

Height is the average length in inches of mature plants from the ground to the tip of the main stem. To convert to centimeters, multiply by 2.54.

Seed Size (i.e. weight per seed) is recorded in grams per 100 seeds based on a 100- or 200-seed sample. To convert to seeds per pound, divide this into 45,359.2. QTLs for lodging were found in three consensus regions on two LGs: C2 and L (Tables A-G and FIG. 14). All three regions, 107-116 cM on LG C2, 3-11 cM on LG L, and 68-101 cM on LG L were each found in three mapping populations developed from five or six mapping parents (Tables A-G).

| Group | Reference: | Range | Early check | Late check |
|---|---|---|---|---|
| 00 | MN0071 | −7 to +5 | Jim | Trail (L) |
| 0 | Lambert | −6 to +2 | Traill (E) | Parker (L) |
| I | MN1410 | −4 to +4 | Lambert (0) | IA1008 (SCN) |
| II | IA2068 | −3 to +5 | IA1021 (I) | IA3024 (L) |
| III | IA3023 | −6 to +2 | IA3024 | Macon (L) |
| IV | LD00-3309 | −4 to +7 | Macon (III) | |
| 00RR | RG700RR | | | AG0202 |
| 0RR | RG200RR | | | SD1111RR (L) |
| IRR | SD1611RR | | SD1111RR (E) | AG2002 |
| IIRR | AG2403 | | AG2002 | NEX2905A0R (L) |
| IIIRR | AG3505 | | NEX2905A0R (E) | DKB3852 |
| IVRR | AG4103 | | DKB38-52 | AG4403 |

TABLE B

Consensus regions for Lodging.

| Trait/QTL Lodging | LG[a] | Start position[b] | End position[b] | Mapping parent 1 | Mapping parent 2 | Reference |
|---|---|---|---|---|---|---|
| Ldge 6-1 | C2 | 107 | 109 | Archer | Minsoy | Orf et al. (1999b) |
| Ldge 9-1 | C2 | 111 | 113 | Minsoy | Noir 1 | Specht et al. (2001) |
| Ldge 3-2 | C2 | 114 | 116 | PI 27890 | PI 290136 | Orf et al. (1999b) |
| Ldge 5-11 | L | 3 | 5 | PI 416937 | Young | Lee et al. (1996a) |
| Ldge 3-3 | L | 8 | 10 | PI 27890 | PI 290136 | Mansur et al. (1996) |
| Ldge 9-3 | L | 9 | 11 | Minsoy | Noir 1 | Specht et al. (2001) |
| Ldge 1-1 | L | 68 | 87 | PI 27890 | PI 290136 | Mansur et al. (1996) |
| Ldge 8-4 | L | 88 | 90 | Minsoy | Noir 1 | Orf et al. (1999b) |
| Ldge 4-2 | L | 88 | 90 | Coker237 | PI 97100 | Lee et al. (1996c) |
| Ldge 9-5 | L | 88 | 90 | Minsoy | Noir 1 | Specht et al. (2001) |
| Ldge 4-3 | L | 89 | 101 | Coker237 | PI 97100 | Lee et al. (1996c) |
| Ldge 3-1 | L | 91 | 93 | PI 27890 | PI 290136 | Mansur et al. (1996) |

QTLs for plant height were found in 10 consensus regions on eight LGs: C2, D1b, F, I, J, K, L, and M (Tables A-G and FIG. 14). The 107-118 cM region on LG C2 was found in five mapping populations developed from nine mapping parents (Tables A-G The regions 120-133 cM on LG D1b, 66-69 cM on LG F, 34-38 cM on LG I, 36-48 cM on LG K, 8-15 cM on LG L, and 34-44 cM on LG L were each found in two mapping populations developed from four mapping parents (Table 1). The regions 11-29 cM on LG J and 32-40 cM on LG M were each found in three mapping populations developed from six mapping parents (Table 3). The 68-114 cM region on LG L was found in six mapping populations developed from nine mapping parents (Tables A-G).

Regions Controlling Agronomic Traits in QTL Mapping Studies in Soybean Plants.

Based on the data collected in the SoyBase database (Grant et al. 2008), at least 85 traits within over 1,100 QTLs were identified. These agronomic traits were mapped to at least one QTL controlling region for each trait including abnormal seedling, acidic protein fraction, alpha prime conglycinin protein fraction, aluminum tolerance, arabinose, arabinose-galactose basic protein fraction, beginning maturity, beginning pod, beta conglycinin protein fraction, brown stem rot resistance, canopy height, canopy width, carbon isotope discrimination, cell wall polysaccharide, chlorimuron ethyl sen-

TABLE C

Consensus regions for Plant height.

| Trait/QTL Plant height | LG[a] | Start position[b] | End position[b] | Mapping parent 1 | Mapping parent 2 | Reference |
|---|---|---|---|---|---|---|
| Pl ht 8-1 | C2 | 107 | 109 | Archer | Minsoy | Orf et al. (1999b) |
| Pl ht 18-4 | C2 | 112 | 114 | IA2008 | PI 468916 | Wang et al. (2004a) |
| Pl ht 13-2 | C2 | 112 | 114 | Minsoy | Noir 1 | Specht et al. (2001) |
| Pl ht 11-1 | C2 | 116 | 118 | S100 | Tokyo | Mian et al. (1998) |
| Pl ht 6-3 | C2 | 116 | 118 | PI 27890 | PI 290136 | Lark et al. (1995) |
| Pl ht 6-12 | D1b | 120 | 122 | PI 27890 | PI 290136 | Lark et al. (1995) |
| Pl ht 5-5 | D1b | 131 | 133 | PI 416937 | Young | Lee et al. (1996a) |
| Pl ht 5-8 | F | 66 | 68 | PI 416937 | Young | Lee et al. (1996a) |
| Pl ht 11-3 | F | 67 | 69 | S100 | Tokyo | Mian et al. (1998) |
| Pl ht 12-1 | I | 34 | 36 | A81356022 | PI 468916 | Yuan et al. (2002) |
| Pl ht 16-1 | I | 36 | 38 | Essex | Williams | Chapman et al. (2003) |
| Pl ht 13-5 | J | 11 | 13 | Minsoy | Noir 1 | Specht et al. (2001) |
| Pl ht 6-6 | J | 20 | 22 | PI 27890 | PI 290136 | Lark et al. (1995) |
| Pl ht 5-9 | J | 27 | 29 | PI 416937 | Young | Lee et al. (1996a) |
| Pl ht 18-3 | K | 36 | 38 | IA2008 | PI 468916 | Wang et al. (2004a) |
| Pl ht 15-1 | K | 46 | 48 | Flyer | Hartwig | Yuan et al. (2002) |
| Pl ht 6-7 | L | 8 | 10 | PI 27890 | PI 290136 | Lark et al. (1995) |
| Pl ht 13-7 | L | 13 | 15 | Minsoy | Noir 1 | Specht et al. (2001) |
| Pl ht 5-12 | L | 34 | 36 | PI 416937 | Young | Lee et al. (1996a) |
| Pl ht 6-4 | L | 42 | 44 | PI 27890 | PI 290136 | Lark et al. (1995) |
| Pl ht 8-4 | L | 66 | 68 | Archer | Minsoy | Orf et al. (1999b) |
| Pl ht 1-1 | L | 68 | 87 | PI 27890 | PI 290136 | Mansur et al. (1993) |
| Pl ht 8-3 | L | 69 | 71 | Archer | Minsoy | Orf et al. (1999b) |
| Pl ht 6-1 | L | 86 | 88 | PI 27890 | PI 290136 | Lark et al. (1995) |
| Pl ht 4-2 | L | 88 | 90 | Coker237 | PI 97100 | Lee et al. (1996c) |
| Pl ht 13-8 | L | 88 | 90 | Minsoy | Noir 1 | Specht et al. (2001) |
| Pl ht 4-4 | L | 89 | 101 | Coker237 | PI 97100 | Lee et al. (1996c) |
| Pl ht 3-1 | L | 91 | 93 | PI 27890 | PI 290136 | Mansur et al. (1996) |
| Pl ht 5-10 | L | 100 | 102 | PI 416937 | Young | Lee et al. (1996a) |
| Pl ht 9-2 | L | 106 | 108 | Archer | Noir 1 | Orf et al. (1999b) |
| Pl ht 6-2 | L | 112 | 114 | PI 27890 | PI 290136 | Lark et al. (1995) |
| Pl ht 18-6 | M | 32 | 34 | IA2008 | PI 468916 | Wang et al. (2004a) |
| Pl ht 13-9 | M | 33 | 35 | Minsoy | Noir 1 | Specht et al. (2001) |
| Pl ht 6-5 | M | 38 | 40 | PI 27890 | PI 290136 | Lark et al. (1995) | sitivity, common cutworm resistance, conglycinin protein fraction, corn earworm resistance, daidzein content, first flower, flooding tolerance, flowering time, fructose content, galactose content glycinin protein fraction, glycitein content, height/lodging, hypocotyl length, iron efficiency, javanese root-knot nematode resistance, leaf area, leaf ash, leaf chlorosis leaf length, leaf phosphorus content, leaf width, leaflet area, leaflet shape, linoleic acid content, linolenic acid content, lodging, nitrogen accumulation at growth stage R5, oil content, oil/protein ratio, oleic acid concentration, palmitic acid concentration, peanut root-knot nematode resistance, pectin concentration, phomopsis seed decay, photoperiod insensitivity, *phytophthora sojae* partial resistance, plant height, pod dehiscence, pod maturity date, protein concentration, reproductive period, rhizoctonia rot and hypocotyl rot, root necrosis, salt tolerance, sclerotinia stem rot, seed abortion, seed coat hardness, seed filling period, seed number, seed set, seed weight, southern root-knot nematode resistance, soybean cyst nematode resistance, soybean looper resistance (229-M), specific leaf weight, sprout yield, stearic acid concentration, stem diameter, stem length, sucrose concentration, sudden death syndrome resistance, tobacco budworm resistance (229-M), tobacco ringspot virus resistance, trigonelline concentration (dry weight), trigonelline concentration (fresh weight), water use efficiency, and yield, such as Yield/Height, Yield/Seed weight, SoyBase (Grant et al. 2008), Some of the QTLs listed as separate QTLs in SoyBase appear to be the same QTL identified in the same population (e.g. SCN 29-1, SCN 29-4, and SCN 29-8 on linkage group G) while some other QTLs might be the same QTL identified in different populations (see the "consensus QTL regions" section below). The amount of phenotypic variation accounted for by a single QTL varied from 1% to 97% (Table 2). The majority of the QTLs listed in SoyBase were not confirmed by separate studies. However, independent mapping studies with populations developed from different parents frequently identified QTLs for the same trait in a similar region on the integrated linkage map. The consistence of the QTL locations found in independent studies with different mapping populations indicates the existence of a real QTL in the region. For example, a QTL for SCN resistance was identified in the 0-37 cM region on linkage group G in 14 mapping populations. The major SCN resistance gene rhg1 was found in this region (Concibido et al. 2004). Thus the inventors contemplate identifying specific genes contributing to aphid resistance within the QTLs identified during the development of the present inventions. SCN resistance, 99 QTLs were identified (Tables A-G).

TABLE D

Consensus regions for QTLs for soybean cyst nematode resistance listed in SoyBase by Grant et al. (2008)

| QTL | $R^2$ (%)[a] | LOD score | P-value | LG[b] | Start position[c] | End position[c] | Peak marker/ interval | Mapping parent 1 | Mapping parent 2 | Reference |
|---|---|---|---|---|---|---|---|---|---|---|
| SCN 2-3 | 1.0 | | 0.0008 | A1 | 7.8 | 9.8 | A487_1 | Hartwig | Williams 82 | Vierling et al. (1996) |
| SCN 18-1 | 7.4 | 2.78 | 0.0010 | A1 | 30.9 | 53.4 | A262_1, Satt300 | PI 438489B | Hamilton | Yue et al. (2001a) |
| SCN 1-1 | | | 0.0015 | A2 | 31.2 | 33.2 | A085_1 | M85-1430 | M83-15 | Concibido et al. (1994) |
| SCN 19-1 | 19.1 | 7.00 | 0.0010 | A2 | 45.6 | 53.1 | K400_2, T155_2 | PI 438489B | Hamilton | Yue et al. (2001a) |
| SCN 27-2 | 26.2 | 5.20 | | A2 | 47.6 | 49.6 | E(CCG)M(AAC)405 | Essex | Forrest | Meksem et al. (2001) |
| SCN 9-2 | 25.0 | | | A2 | 47.8 | 49.8 | I | Peking | Essex | Mahalingam et al. (1995) |
| SCN 3-1 | 9.0 | 5.80 | | A2 | 47.8 | 49.8 | I | PI 437654 | BSR101 | Webb et al. (1995) |
| SCN 29-5 | 17.7 | 14.50 | | A2 | 49.4 | 60.6 | Sat_400, Satt424 | Hamilton | PI 90763 | Guo et al. (2006) |
| SCN 8-5 | 23.2 | 5.10 | | A2 | 53.2 | 55.2 | BLT065_1 | Essex | Forrest | Chang et al. (1997) |
| SCN 13-2 | 40.0 | | 0.6400 | A2 | 53.2 | 55.2 | BLT065_1 | Flyer | Hartwig | Prabhu et al. (1999) |
| SCN 9-3 | 8.0 | | | A2 | 56.9 | 58.9 | S07a | Peking | Essex | Mahalingam et al. (1995) |
| SCN 30-3 | 29.0 | | 0.0005 | A2 | 59.6 | 61.6 | Satt424 | PI 437654 | Bell | Brucker et al. (2005) |
| SCN 8-4 | 15.1 | 2.80 | | A2 | 65.8 | 67.8 | OW15_400 | Essex | Forrest | Chang et al. (1997) |
| SCN 9-1 | 12.5 | | | A2 | 70.4 | 72.4 | A136_1 | Peking | Essex | Mahalingam et al. (1995) |
| SCN 26-1 | 9.5 | 3.71 | 0.0011 | B1 | 58.9 | 64.8 | A118_1, A006_1 | PI 89772 | Hamilton | Yue et al. (2001) |
| SCN 2-1 | 91.0 | | 0.0001 | B1 | 63.8 | 65.8 | A006_1 | Hartwig | Williams 82 | Vierling et al. (1996) |
| SCN 23-1 | 16.6 | 6.83 | 0.0001 | B1 | 64.8 | 84.2 | A006_1, Satt583 | PI 89772 | Hamilton | Yue et al. (2001b) |
| SCN 24-1 | 6.8 | 2.78 | 0.0035 | B1 | 64.8 | 84.2 | A006_1, Satt583 | PI 89772 | Hamilton | Yue et al. (2001b) |
| SCN 17-1 | 12.7 | 4.20 | 0.0010 | B1 | 84.2 | 101.0 | Satt583, Sat_123 | PI 438489B | Hamilton | Yue et al. (2001a) |
| SCN 18-2 | 7.4 | 2.79 | 0.0010 | B1 | 84.2 | 101.0 | Satt583, Sat_123 | PI 438489B | Hamilton | Yue et al. (2001a) |
| SCN 20-1 | 11.0 | 2.70 | 0.0010 | B1 | 84.2 | 101.0 | Satt583, Sat_123 | PI 438489B | Hamilton | Yue et al. (2001a) |

TABLE D-continued

Consensus regions for QTLs for soybean cyst nematode resistance listed in SoyBase by Grant et al. (2008)

| QTL | $R^2$ (%)[a] | LOD score | P-value | LG[b] | Start position[c] | End position[c] | Peak marker/ interval | Mapping parent 1 | Mapping parent 2 | Reference |
|---|---|---|---|---|---|---|---|---|---|---|
| SCN 29-10 | 11.2 | 6.00 | | B1 | 102.6 | 124.0 | Satt359, Satt453 | Hamilton | PI 90763 | Guo et al. (2006) |
| SCN 2-2 | 1.0 | | 0.0001 | B1 | 125.0 | 127.0 | A567_1 | Hartwig | Williams 82 | Vierling et al. (1996) |
| SCN 17-2 | 11.7 | 2.75 | 0.0010 | B2 | 55.2 | 62.7 | A329_1, Satt168 | PI 438489B | Hamilton | Yue et al. (2001a) |
| SCN 19-2 | 8.1 | 2.56 | 0.0010 | B2 | 55.2 | 62.7 | A329_1, Satt168 | PI 438489B | Hamilton | Yue et al. (2001a) |
| SCN 10-1 | 21.0 | | | B2 | 97.5 | 99.5 | A593_1 | Peking | Essex | Qiu et al. (1999) |
| SCN 10-3 | 15.0 | | | B2 | 117.7 | 119.7 | T005_1 | Peking | Essex | Qiu et al. (1999) |
| SCN 11-3 | 9.0 | | | B2 | 117.7 | 119.7 | T005_1 | Peking | Essex | Qiu et al. (1999) |
| SCN 21-1 | 11.1 | 3.61 | 0.0010 | C1 | 18.6 | 21.0 | A059_1, A463_1 | PI 438489B | Hamilton | Yue et al.(2001a) |
| SCN 18-3 | 10.2 | 2.56 | 0.0010 | C1 | 21.0 | 24.1 | A463_1, Satt396 | PI 438489B | Hamilton | Yue et al. (2001a) |
| SCN 22-1 | 5.0 | 4.40 | | C2 | 1.0 | 1.0 | A121_1 | PI 468916 | A81356022 | Wang et al. (2001) |
| SCN 9-6 | 8.0 | | | C2 | 94.6 | 96.6 | A635_1 | Peking | Essex | Mahalingam et al. (1995) |
| SCN 17-3 | 7.1 | 6.80 | 0.0010 | C2 | 126.2 | 145.5 | Satt202, Satt371 | PI 438489B | Hamilton | Yue et al.(2001a) |
| SCN 20-2 | 8.3 | 3.05 | 0.0010 | C2 | 126.2 | 145.5 | Satt202, Satt371 | PI 438489B | Hamilton | Yue et al. (2001a) |
| SCN 19-3 | 10.7 | 5.47 | 0.0010 | D1a | 6.4 | 34.9 | A398_1, K478_1 | PI 438489B | Hamilton | Yue et al. (2001a) |
| SCN 20-3 | 9.4 | 4.17 | 0.0010 | D1a | 6.4 | 34.9 | A398_1, K478_1 | PI 438489B | Hamilton | Yue et al. (2001a) |
| SCN 21-2 | 7.4 | 4.14 | 0.0010 | D1a | 6.4 | 34.9 | A398_1, K478_1 | PI 438489B | Hamilton | Yue et al. (2001a) |
| SCN 26-2 | 7.8 | 3.30 | 0.0015 | D1a | 43.8 | 48.1 | Satt342, Satt368 | PI 89772 | Hamilton | Yue et al. (2001b) |
| SCN 23-2 | 9.7 | 4.59 | 0.0014 | D2 | 15.0 | 39.4 | B132_4, Satt372 | PI 89772 | Hamilton | Yue et al. (2001b) |
| SCN 16-1 | 41.0 | | 0.0010 | D2 | 86.3 | 88.3 | Satt082 | Hartwig | BR92-31983 | Schuster et al. (2001) |
| SCN 12-2 | 9.0 | | | E | 16.1 | 18.1 | A963_1 | Peking | Essex | Qiu et al. (1999) |
| SCN 22-3 | 23.0 | 3.50 | | E | 33.2 | 35.2 | Satt598 | PI 468916 | A81356022 | Wang et al. (2001) |
| SCN 29-9 | 12.5 | 7.20 | | E | 35.8 | 43.1 | Satt573, Satt204 | Hamilton | PI 90763 | Guo et al. (2006) |
| SCN 18-4 | 8.0 | 2.57 | 0.0010 | E | 37.3 | 45.1 | A656_1, Satt452 | PI 438489B | Hamilton | Yue et al. (2001a) |
| SCN 21-3 | 18.7 | 5.01 | 0.0010 | E | 37.3 | 45.1 | A656_1, Satt452 | PI 438489B | Hamilton | Yue et al. (2001a) |
| SCN 25-1 | 15.7 | 3.56 | 0.0053 | E | 51.0 | 70.2 | A135_3, Satt231 | PI 89772 | Hamilton | Yue et al. (2001b) |
| SCN 29-1 | 14.7 | 7.90 | | G | 0.0 | 12.5 | Satt163, Satt688 | Hamilton | PI 90763 | Guo et al. (2006) |
| SCN 29-4 | 28.1 | 22.10 | | G | 0.0 | 12.5 | Satt163, Satt688 | Hamilton | PI 90763 | Guo et al. (2006) |
| SCN 29-8 | 13.0 | 7.10 | | G | 0.0 | 12.5 | Satt163, Satt688 | Hamilton | PI 90763 | Guo et al. (2006) |
| SCN 4-1 | 26.2 | | 0.0001 | G | 0.8 | 2.8 | C006_1 | Evans | Peking | Concibido et al. (1997) |
| SCN 5-1 | 44.8 | | 0.0001 | G | 0.8 | 2.8 | C006_1 | Evans | PI 90763 | Concibido et al. (1997) |
| SCN 6-1 | 36.3 | | 0.0001 | G | 0.8 | 2.8 | C006_1 | Evans | PI 88788 | Concibido et al. (1997) |
| SCN 13-1 | 6.4 | | 0.0760 | G | 0.8 | 2.8 | Satt038 | Flyer | Hartwig | Prabhu et al. (1999) |
| SCN 8-3 | 12.9 | 2.70 | | G | 1.0 | 3.0 | OI03_450 | Essex | Forrest | Chang et al. (1997) |
| SCN 4-4 | 28.1 | | | G | 1.8 | 8.6 | C006_1, Bng122_1 | Evans | Peking | Concibido et al. (1996) |
| SCN 5-3 | 52.7 | | | G | 1.8 | 8.6 | C006_1, Bng122_1 | Evans | PI 90763 | Concibido et al. (1996) |
| SCN 6-2 | 40.0 | | | G | 1.8 | 8.6 | C006_1, Bng122_1 | Evans | PI 88788 | Concibido et al. (1996) |
| SCN 7-1 | 51.4 | | | G | 1.8 | 8.6 | C006_1, Bng122_1 | Evans | PI 209332 | Concibido et al. (1996) |
| SCN 30-1 | 14.0 | | 0.0400 | G | 3.5 | 5.5 | Satt309 | PI 437654 | Bell | Brucker et al. (2005) |
| SCN 30-2 | 32.0 | | 0.0001 | G | 3.5 | 5.5 | Satt309 | PI 437654 | Bell | Brucker et al. (2005) |
| SCN 14-2 | 97.0 | | 0.0001 | G | 3.5 | 5.5 | Satt309 | Essex | Forrest | Meksem et al. (1999) |
| SCN 23-3 | 26.6 | 13.67 | 0.0001 | G | 4.5 | 5.8 | B053_1, Satt309 | PI 89772 | Hamilton | Yue et al. (2001b) |
| SCN 24-2 | 4.6 | 2.53 | 0.0095 | G | 4.5 | 5.8 | B053_1, Satt309 | PI 89772 | Hamilton | Yue et al. (2001b) |
| SCN 25-2 | 23.0 | 12.65 | 0.0001 | G | 4.5 | 5.8 | B053_1, Satt309 | PI 89772 | Hamilton | Yue et al. (2001b) |

TABLE D-continued

Consensus regions for QTLs for soybean cyst nematode resistance listed in
SoyBase by Grant et al. (2008)

| QTL | $R^2$ (%)[a] | LOD score | P-value | LG[b] | Start position[c] | End position[c] | Peak marker/ interval | Mapping parent 1 | Mapping parent 2 | Reference |
|---|---|---|---|---|---|---|---|---|---|---|
| SCN 26-3 | 10.0 | 5.02 | 0.0001 | G | 4.5 | 5.8 | B053_1, Satt309 | PI 89772 | Hamilton | Yue et al. (2001b) |
| SCN 28-1 | 87.0 | 40.60 | | G | 4.5 | 8.6 | Satt309, Bng122 | Bell | Colfax | Glover et al. (2004) |
| SCN 28-3 | 64.0 | 17.70 | | G | 4.5 | 8.6 | Satt309, Bng122 | Bell | Colfax | Glover et al. (2004) |
| SCN 27-1 | 24.1 | 5.10 | | G | 4.8 | 6.8 | E(ATG)M(CGA)87 | Essex | Forrest | Meksem et al. (2001) |
| SCN 15-1 | | | | G | 5.8 | 35.5 | B053_1, A112_1 | PI 88287 | PI 89008 | Vaghchhipawala et al. (2001) |
| SCN 8-2 | 11.3 | 2.50 | | G | 7.6 | 9.6 | Bng122_1 | Essex | Forrest | Chang et al. (1997) |
| SCN 14-1 | 19.0 | | 0.0730 | G | 7.6 | 9.6 | Bng122_1 | Essex | Forrest | Meksem et al. (1999) |
| SCN 8-1 | 4.2 | 1.20 | | G | 10.6 | 12.6 | OG13_490 | Essex | Forrest | Chang et al. (1997) |
| SCN 3-2 | 22.0 | 15.40 | | G | 11.0 | 13.0 | PHP05354a, PHP05219a | PI 437654 | BSR101 | Webb et al. (1995) |
| SCN 1-3 | 36.0 | | 0.0001 | G | 23.1 | 25.1 | K069_1 | M85-1430 | M83-15 | Concibido et al. (1994) |
| SCN 17-4 | 15.8 | 9.08 | 0.0010 | G | 23.1 | 54.7 | A096_3, Satt130 | PI 438489B | Hamilton | Yue et al. (2001a) |
| SCN 18-5 | 12.8 | 7.52 | 0.0010 | G | 23.1 | 54.7 | A096_3, Satt130 | PI 438489B | Hamilton | Yue et al. (2001a) |
| SCN 19-4 | 13.6 | 4.46 | 0.0010 | G | 23.1 | 66.6 | Satt012, Satt130 | PI 438489B | Hamilton | Yue et al. (2001a) |
| SCN 2-4 | 1.0 | | 0.0018 | G | 34.5 | 36.5 | A112_1 | Hartwig | Williams 82 | Vierling et al. (1996) |
| SCN 20-4 | 5.8 | 2.03 | 0.0010 | G | 62.2 | 66.6 | Satt012, Satt199 | PI 438489B | Hamilton | Yue et al. (2001a) |
| SCN 22-2 | 27.0 | 4.80 | | G | 89.0 | 91.0 | A245_2 | PI 468916 | A81356022 | Wang et al. (2001) |
| SCN 29-3 | 6.7 | 3.00 | | G | 102.6 | 124.0 | Satt453, Satt359 | Hamilton | PI 90763 | Guo et al. (2006) |
| SCN 4-2 | 17.6 | | 0.0002 | G | 108.5 | 110.5 | A378_1 | Evans | Peking | Concibido et al. (1997) |
| SCN 10-5 | 12.0 | | | H | 120.3 | 122.3 | K014_1 | Peking | Essex | Qiu et al. (1999) |
| SCN 11-2 | 9.0 | | | H | 120.3 | 122.3 | K014_1 | Peking | Essex | Qiu et al. (1999) |
| SCN 10-4 | 13.0 | | | H | 123.1 | 125.1 | B072_1 | Peking | Essex | Qiu et al. (1999) |
| SCN 11-1 | 13.0 | | | H | 123.1 | 125.1 | B072_1 | Peking | Essex | Qiu et al. (1999) |
| SCN 12-1 | 11.0 | | | I | 37.1 | 39.1 | K011_1 | Peking | Essex | Qiu et al. (1999) |
| SCN 28-2 | 2.0 | 2.50 | | J | 65.0 | 67.8 | Satt244, Satt547 | Bell | Colfax | Glover et al. (2004) |
| SCN 28-4 | 7.0 | 3.40 | | J | 65.0 | 78.6 | Satt244, Satt431 | Bell | Colfax | Glover et al. (2004) |
| SCN 29-2 | 7.8 | 4.60 | | J | 67.8 | 75.1 | Satt547, Sat_224 | Hamilton | PI 90763 | Guo et al. (2006) |
| SCN 29-6 | 4.2 | 13.90 | | J | 67.8 | 75.1 | Satt547, Sat_224 | Hamilton | PI 90763 | Guo et al. (2006) |
| SCN 1-2 | | | 0.0001 | J | 73.0 | 75.0 | B032_1 | M85-1430 | M83-15 | Concibido et al. (1994) |
| SCN 5-2 | 18.8 | | 0.0001 | J | 73.0 | 75.0 | B032_1 | Evans | PI 90763 | Concibido et al. (1997) |
| SCN 29-7 | 4.0 | 3.00 | | L | 87.4 | 93.9 | Sat_286, Satt229 | Hamilton | PI 90763 | Guo et al. (2006) |
| SCN 3-3 | 7.0 | 4.80 | | M | 74.0 | 76.0 | PHP02275a, PHP02301a | PI 437654 | BSR101 | Webb et al. (1995) |
| SCN 4-3 | 14.3 | | 0.0001 | N | 33.9 | 35.9 | A280_1 | Evans | Peking | Concibido et al. (1997) |
| SCN 10-2 | 16.0 | | | | | | A018_3 | Peking | Essex | Qiu et al. (1999) |
| SCN 9-4 | 6.0 | | | | | | E01c | Peking | Essex | Mahalingam et al. (1995) |
| SCN 9-5 | 6.0 | | | | | | G15d | Peking | Essex | Mahalingam et al. (1995) |

[a]$R^2$ = Phenotypic variation explained by a QTL
[b]LG = linkage group. The linkage group names are from the integrated map by Song et al. (2004).
[c]The start positions and end positions are from the integrated map by Song et al. (2004). When only a single marker that was associated with a QTL in a published study could be placed on the consensus map, an arbitrary 2 cM interval with 1 cM on either side of the marker was defined as the QTL region in SoyBase

TABLE E

Consensus regions for QTLs for nematode resistance and earworm resistance.

Soybean cyst nematode resistance

| | | | | | | |
|---|---|---|---|---|---|---|
| SCN 19-1 | A2 | 46 | 53 | Hamilton | PI 438489B | Yue et al. (2001) |
| SCN 3-1 | A2 | 48 | 50 | BSR101 | PI 437654 | Webb et al. (1995) |
| SCN 9-2 | A2 | 48 | 50 | Essex | Peking | Mahalingam et al. (1995) |
| SCN 29-4 | A2 | 49 | 61 | Hamilton | PI 90763 | Guo et al. (2006) |
| SCN 8-5 | A2 | 53 | 55 | Essex | Forrest | Chang et al. (1997) |
| SCN 13-2 | A2 | 53 | 55 | Flyer | Hartwig | Prabhu et al. (1999) |
| SCN 30-3 | A2 | 60 | 62 | Bell | PI 437654 | Brucker et al. (2005) |
| SCN 2-1 | B1 | 64 | 66 | Hartwig | Williams 82 | Vierling et al. (1996) |
| SCN 24-1 | B1 | 65 | 84 | Hamilton | PI 89772 | Yue et al. (2001) |
| SCN 20-1 | B1 | 84 | 101 | Hamilton | PI 438489B | Yue et al. (2001) |
| SCN 29-7 | B1 | 103 | 124 | Hamilton | PI 90763 | Guo et al. (2006) |
| SCN 22-3 | E | 33 | 35 | A81356022 | PI 468916 | Wang et al. (2001) |
| SCN 29-6 | E | 36 | 43 | Hamilton | PI 90763 | Guo et al. (2006) |
| SCN 21-3 | E | 37 | 45 | Hamilton | PI 438489B | Yue et al. (2001) |
| SCN 25-1 | E | 51 | 70 | Hamilton | PI 89772 | Yue et al. (2001) |
| SCN 29-5 | G | 0 | 13 | Hamilton | PI 90763 | Guo et al. (2006) |
| SCN 4-1 | G | 1 | 3 | Evans | Peking | Concibido et al. (1997) |
| SCN 5-1 | G | 1 | 3 | Evans | PI 90763 | Concibido et al. (1997) |
| SCN 6-1 | G | 1 | 3 | Evans | PI 88788 | Concibido et al. (1997) |
| SCN 13-1 | G | 1 | 3 | Flyer | Hartwig | Prabhu et al. (1999) |
| SCN 8-3 | G | 1 | 3 | Essex | Forrest | Chang et al. (1997) |
| SCN 7-1 | G | 2 | 9 | Evans | PI 209332 | Concibido et al. (1996) |
| SCN 30-2 | G | 4 | 6 | Bell | PI 437654 | Brucker et al. (2005) |
| SCN 23-3 | G | 5 | 6 | Hamilton | PI 89772 | Yue et al. (2001) |
| SCN 15-1 | G | 6 | 36 | PI 88287 | PI 89008 | Vaghchhipawala et al. (2001) |
| SCN 3-2 | G | 11 | 13 | BSR101 | PI 437654 | Webb et al. (1995) |
| SCN 19-4 | G | 23 | 67 | Hamilton | PI 438489B | Yue et al. (2001) |
| SCN 1-3 | G | 23 | 25 | M83-15 | M85-1430 | Concibido et al. (1994) |
| SCN 2-4 | G | 35 | 37 | Hartwig | Williams 82 | Vierling et al. (1996) |
| SCN 28-4 | J | 65 | 79 | Bell | Colfax | Glover et al. (2004) |
| SCN 29-2 | J | 68 | 75 | Hamilton | PI 90763 | Guo et al. (2006) |
| SCN 5-2 | J | 73 | 75 | Evans | PI 90763 | Concibido et al. (1997) |
| SCN 1-2 | J | 73 | 75 | M83-15 | M85-1430 | Concibido et al. (1994) |

Corn earworm resistance

| | | | | | | |
|---|---|---|---|---|---|---|
| CEW 3-1 | C2 | 90 | 102 | Cobb | PI 227687 | Rector et al. (1999) |
| CEW 8-3 | C2 | 111 | 113 | Archer | Minsoy | Terry et al. (2000) |
| CEW 8-1 | E | 2 | 4 | Archer | Minsoy | Terry et al. (2000) |
| CEW 7-1 | E | 8 | 10 | Minsoy | Noir 1 | Terry et al. (2000) |
| CEW 2-2 | H | 49 | 62 | Cobb | PI 171451 | Rector et al. (1999) |
| CEW 3-2 | H | 49 | 62 | Cobb | PI 227687 | Rector et al. (1999) |
| CEW 9-3 | H | 53 | 61 | Cobb | PI 229358 | Narvel et al. (2001) |
| CEW 6-2 | J | 15 | 17 | Cobb | PI 229358 | Rector et al. (2000) |
| CEW 7-4 | J | 20 | 22 | Minsoy | Noir 1 | Terry et al. (2000) |
| CEW 6-3 | M | 59 | 71 | Cobb | PI 229358 | Rector et al. (2000) |
| CEW 4-1 | M | 59 | 71 | Cobb | PI 171451 | Rector et al. (2000) |

TABLE F

Consensus regions for QTLs for diease resistance.

*Phytophthora* resistance

| | | | | | | |
|---|---|---|---|---|---|---|
| Phyto 1-1a | F | 16 | 18 | Conrad | Sloan | Burnham et al. (2003) |
| Phyto 1-1b | F | 16 | 18 | Conrad | Williams | Burnham et al. (2003) |
| Phyto 1-1c | F | 16 | 21 | Conrad | Harosoy | Burnham et al. (2003) |

Sudden death syndrome resistance

| | | | | | | |
|---|---|---|---|---|---|---|
| SDS 8-2 | C2 | 120 | 122 | Douglas | Pyramid | Njiti et al. (2002) |
| SDS 2-6 | C2 | 131 | 133 | Essex | Forrest | Chang et al. (1996) |
| SDS 8-1 | G | 0 | 1 | Douglas | Pyramid | Njiti et al. (2002) |
| SDS 3-2 | G | 1 | 3 | Essex | Forrest | Chang et al. (1996) |

Brown stem rot resistance

| | | | | | | |
|---|---|---|---|---|---|---|
| BSR 1-1 | J | 67 | 69 | BSR101 | PI 437654 | Lewers et al. (1999) |
| BSR 4-1 | J | 78 | 80 | Century | PI 437833 | Bachman et al. (2001) |
| BSR 3-1 | J | 78 | 80 | Century84 | L78-4094 | Bachman et al. (2001) |

*Sclerotinia* stem rot resistance

| | | | | | | |
|---|---|---|---|---|---|---|
| Sclero 5-1 | A2 | 60 | 62 | S19-90 | Williams82 | Arahana et al. (2001) |
| Sclero 6-2 | A2 | 60 | 62 | Vinton81 | Williams82 | Arahana et al. (2001) |
| Sclero 2-2 | A2 | 60 | 62 | Corsoy79 | Williams82 | Arahana et al. (2001) |

TABLE F-continued

Consensus regions for QTLs for diease resistance.

| Sclero 4-1 | D1a | 109 | 110 | DSR173 | Williams82 | Arahana et al. (2001) |
| Sclero 5-3 | D1a | 109 | 110 | S19-90 | Williams82 | Arahana et al. (2001) |
| Sclero 3-5 | D1b | 118 | 120 | Dassel | Williams82 | Arahana et al. (2001) |
| Sclero 2-7 | D1b | 118 | 120 | Corsoy79 | Williams82 | Arahana et al. (2001) |
| Sclero 2-12 | F | 63 | 65 | Corsoy79 | Williams82 | Arahana et al. (2001) |
| Sclero 5-6 | F | 63 | 65 | S19-90 | Williams82 | Arahana et al. (2001) |
| Sclero 5-9 | G | 85 | 97 | S19-90 | Williams82 | Arahana et al. (2001) |
| Sclero 6-7 | G | 96 | 98 | Vinton81 | Williams82 | Arahana et al. (2001) |
| Sclero 2-20 | L | 54 | 56 | Corsoy79 | Williams82 | Arahana et al. (2001) |
| Sclero 3-14 | L | 54 | 56 | Dassel | Williams82 | Arahana et al. (2001) |
| Sclero 6-13 | O | 120 | 129 | Vinton81 | Williams82 | Arahana et al. (2001) |
| Sclero 3-19 | O | 120 | 129 | Dassel | Williams82 | Arahana et al. (2001) |
| Sclero 4-11 | O | 127 | 129 | DSR173 | Williams82 | Arahana et al. (2001) |

Consensus QTL Regions for Seed Protein and Oil Contents

QTLs for protein content were found in 13 consensus regions on 11 LGs: A1, A2, B1, B2, C1, C2, E, G, I, K, and M (Tables A-G and FIG. 14). The regions 93-96 cM on LG A1, 145-151 cM on LG A2, 28-37 cM on LG B1, 28-46 cM on LG B2, 9-34 cM on LG C1, 90-98 cM on LG C1, 123-128 cM on LG C1, 117-123 cM on LG C2, 89-98 cM on LG G, and 31-42 cM on LG K were each found in two mapping populations developed from four mapping parents (Table 3). The 26-32 cM region on LG E and the 33-40 cM region on LG M were each found in three mapping populations developed from five or six mapping parents (Table 3). The 31-40 cM region on LG I was found in four mapping populations developed from seven mapping parents (Table 3).

QTLs for oil content were found in nine consensus regions on eight LGs: A1, C1, E, H, I, K, L, and M (Tables A-G and FIG. 14). The 88-96 cM region on LG A1 was found in four mapping populations developed from seven mapping parents (Table 3). The regions near 9-11 cM on LG C1, 23-36 cM on LG E, 86-91 cM on LG H, 98-106 cM on LG K, 34-38 cM on LG L, and 35-40 cM on LG M were each found in two mapping populations developed from three or four mapping parents (Table 3). The 22-40 cM region on LG I was found in five mapping populations developed from nine mapping parents (Tables A-G). The 91-96 cM region on LG L was found in three mapping populations developed from six mapping parents (Tables A-G).

Consensus QTL Regions for Disease and Insect Resistance

QTLs for resistance to soybean cyst nematode (SCN) were found in five consensus regions on five LGs: A2, B1, E, G, and J (Tables A-G and FIG. 14). The 46-72 cM region on LG A2 was found in seven mapping populations derived from 11 mapping parents (Table 3). This region contains the Rhg4 SCN resistance gene. The regions 64-124 cM on LG B1 and 33-70 cM on LG E were each found in four mapping populations derived from six mapping parents (Table 3). The 0-37 cM region on LG G was found in 14 mapping populations derived from 20 mapping parents (Tables A-G). This region contains the rhg1 SCN resistance gene. The 65-79 cM region on LG J was found in four mapping populations derived from seven mapping parents (Tables A-G).

Figure 14:
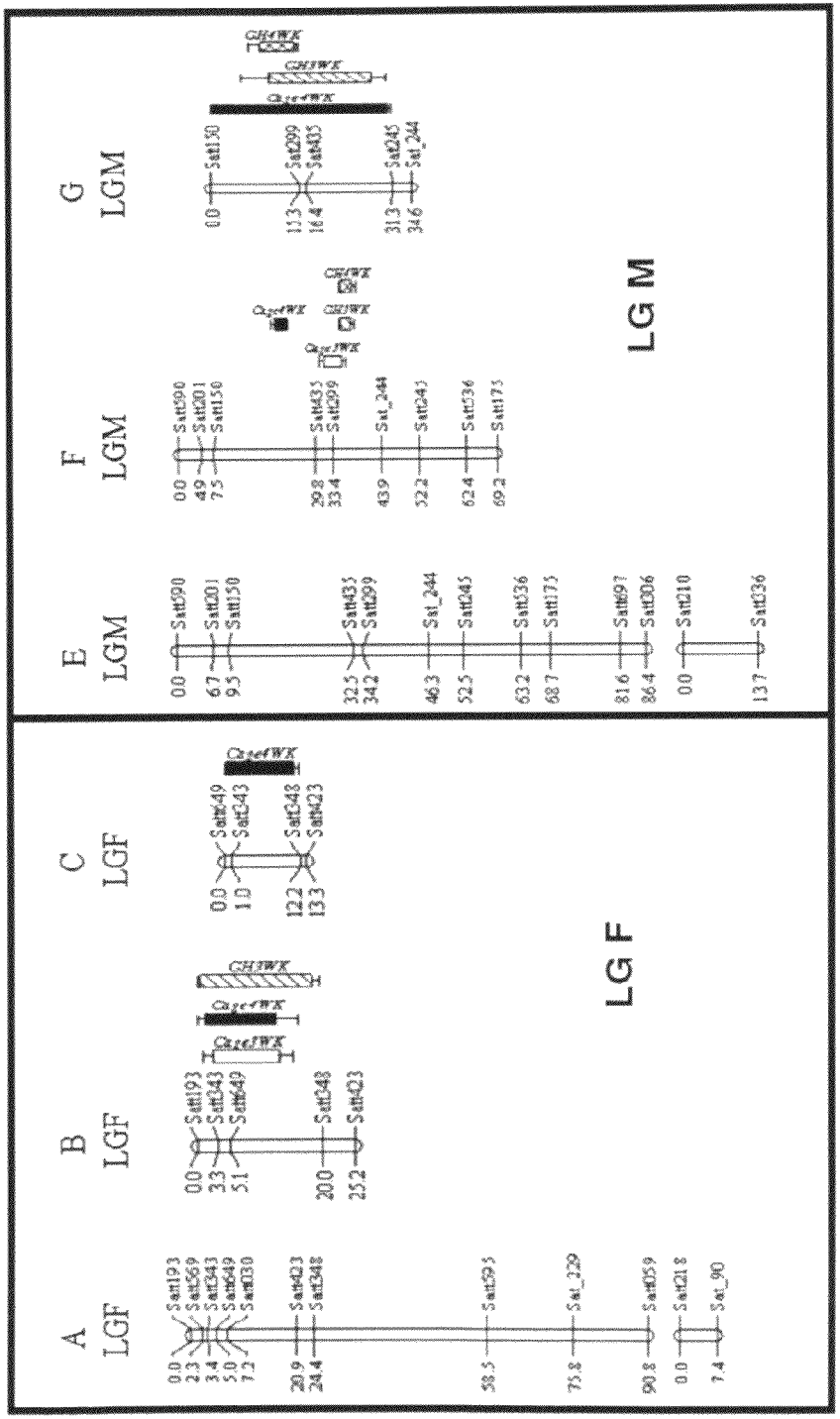
FIG. 14 shows exemplary locations of soybean aphid resistance regions in QTLs F (A-C) and M (E-F) using composite interval mapping method. 1-LOD and 2-LOD support intervals of each QTL are marked by thick and thin bars, respectively. Unfilled bars represent QTLs for the three-week rating in the field cage trial (Cage3WK). Black bars represent QTLs for the four-week rating in the field cage trial (Cage4WK). Bars filled with hatch lines represent QTLs for the three-week rating in the greenhouse trial (GH3WK). Bars filled with cross lines represent QTLs for the four-week rating in the greenhouse trial (GH4WK). A) A and E show maps for linkage groups F and M using a subset of 94 lines selected from within the mapping population PI 567541B×Skylla. B and F: maps for linkage groups F and M using the whole mapping population PI 567541B×Skylla. The QTL positions based on this map are listed at its right side. C and G: maps for linkage groups F and M using the validation population PI 567541B× E00003. The QTL positions based on this map are listed at its right side.
Figure 15:
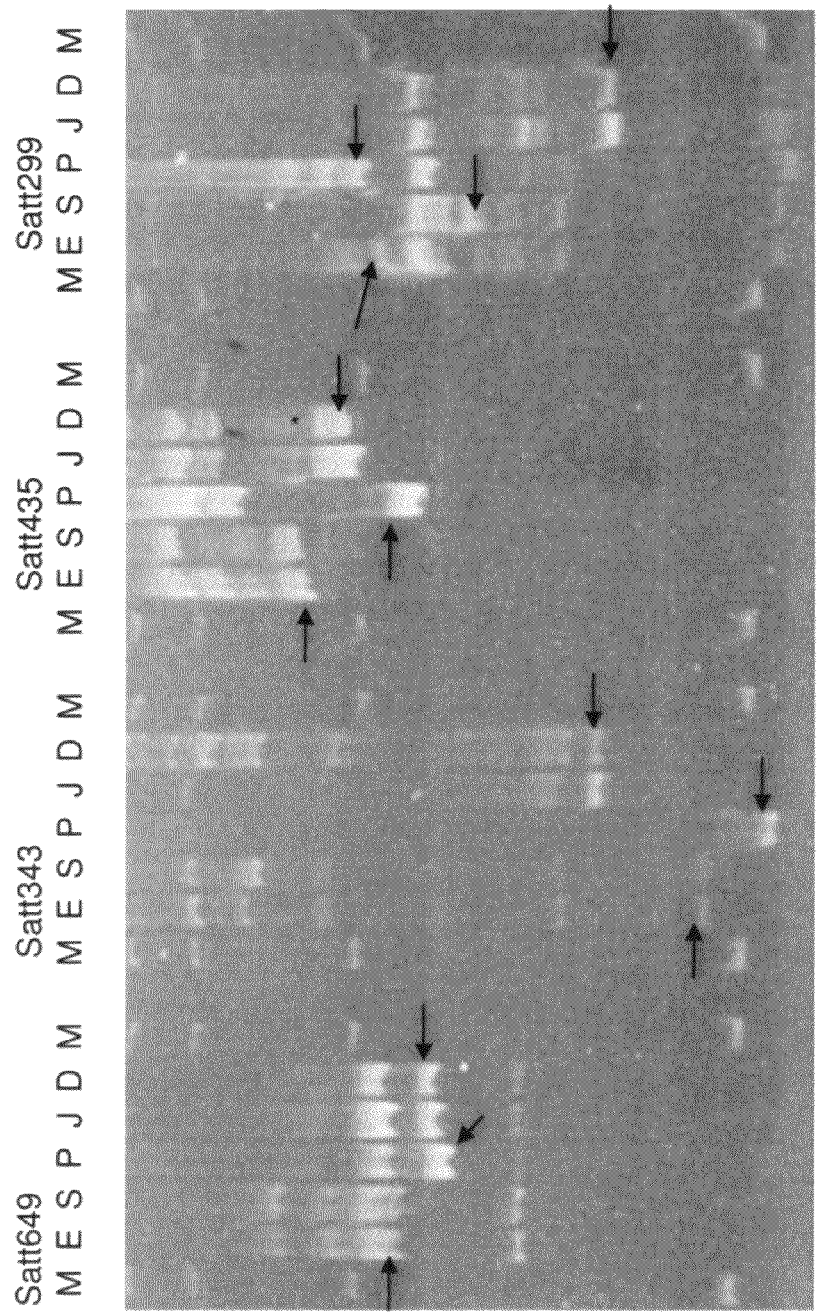
FIG. 15 shows exemplary PCR products amplified by SSR markers Satt299, Satt435, Satt343 and Satt649 within E00003 (E) aphid resistant soybean plants, Skylla (S) susceptible plants, PI567541B (P) aphid resistant soybean plants, Jackson (J), and Dowling (D) soybean plants. M=123 bp PCR marker. Arrows in the figure point to specific bands, collectively a pattern, for differentiating the soybean resistant plants (parents and progeny) of the present inventions from other soybean cultivars (lines) plants. PCR products amplified by SSR markers Satt299, Satt435, Satt649 and Satt343 for E00003 (E), Skylla (S), PI567541B (P), Jackson (J), and Dowling (D). M=123 bp PCR marker. Arrows in the figure points to the particular bands for differentiating among the populations of aphid resistant phenotypes and susceptible phenotypes present in the soybean lines, plants.
Figure 16A:
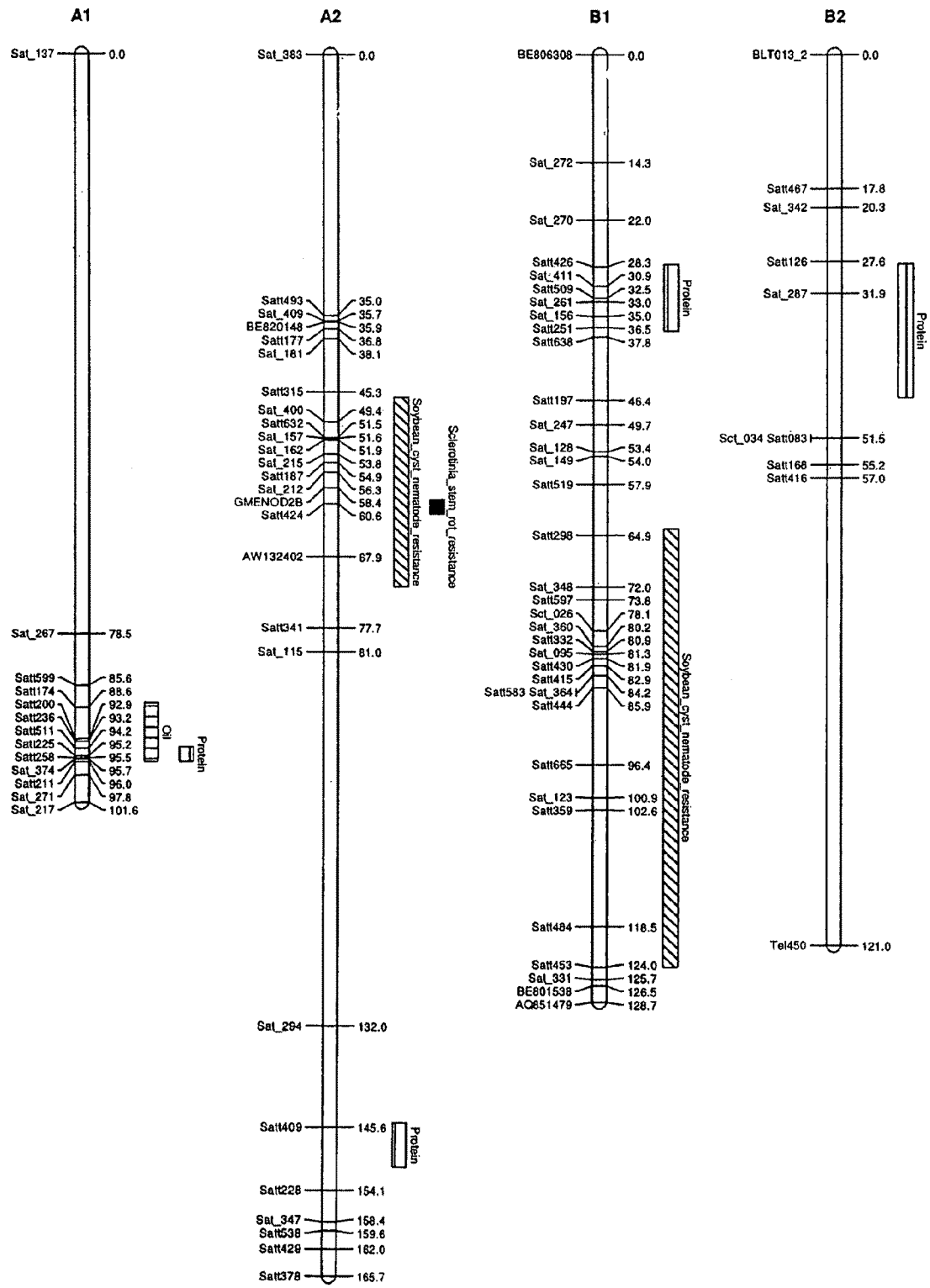
FIG. 16 shows exemplary QTL locations for some embodiments of aphid resistant germplasm.
Figure 16B:
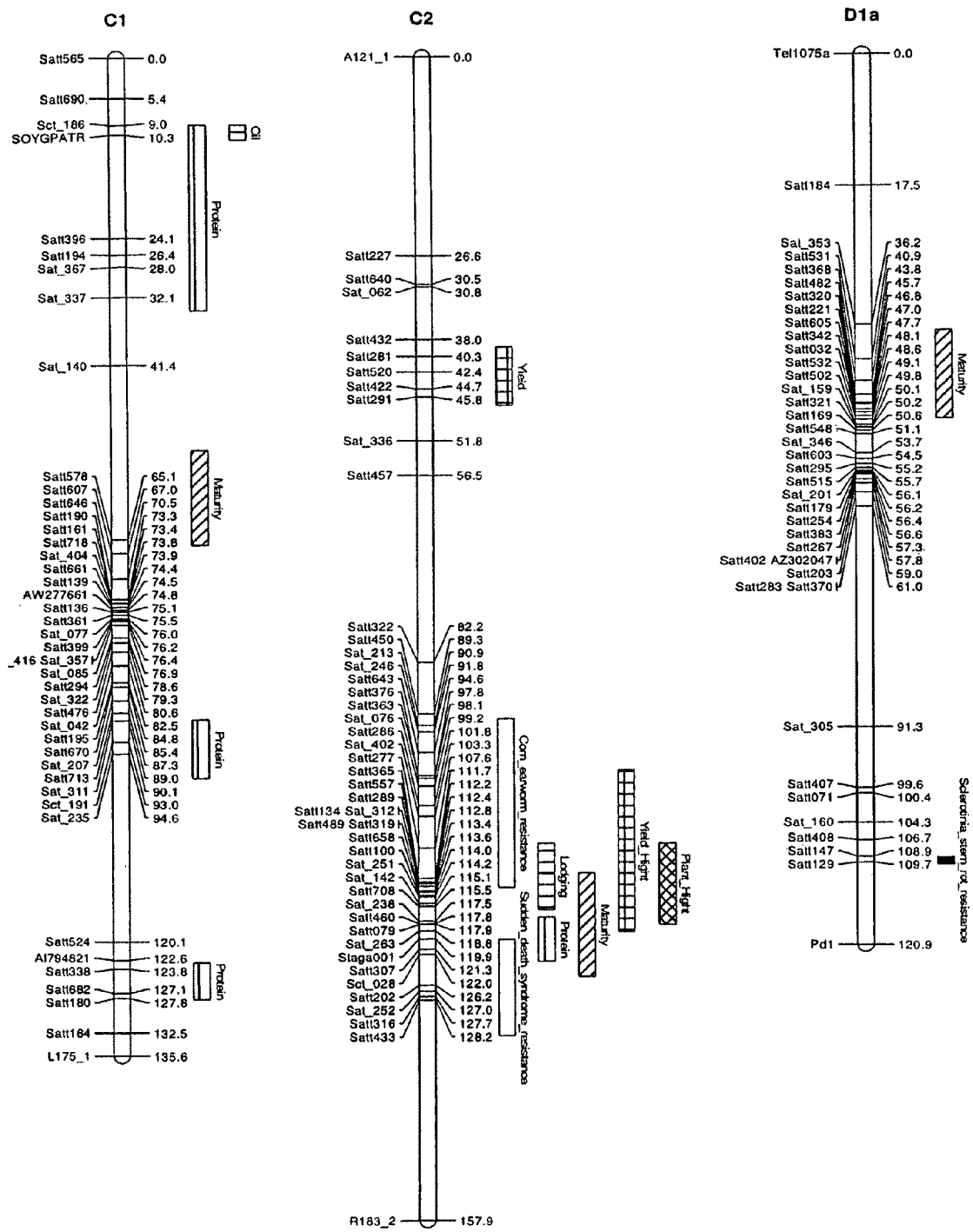
Figure 16C:
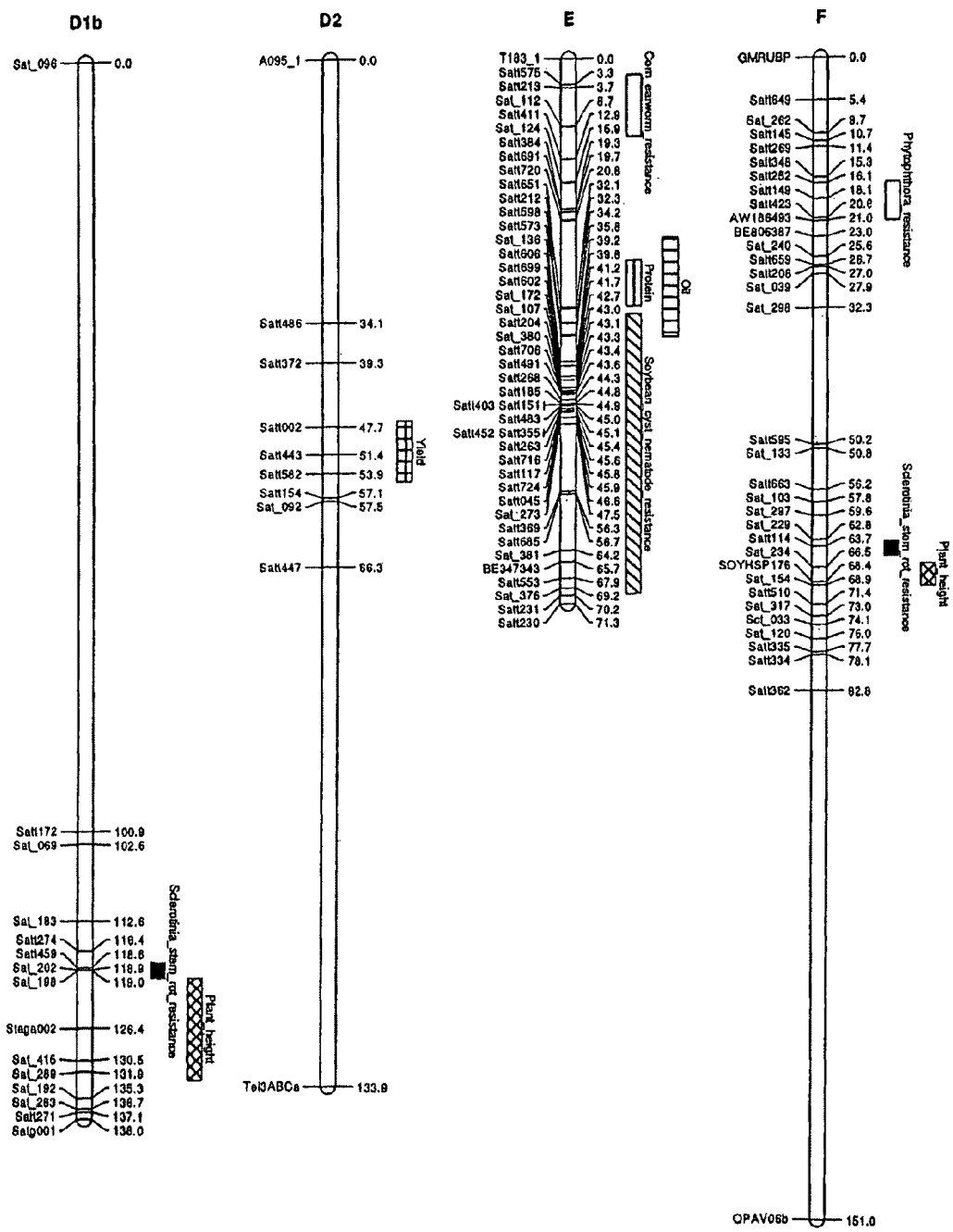
Figure 16D:
Figure 16E:
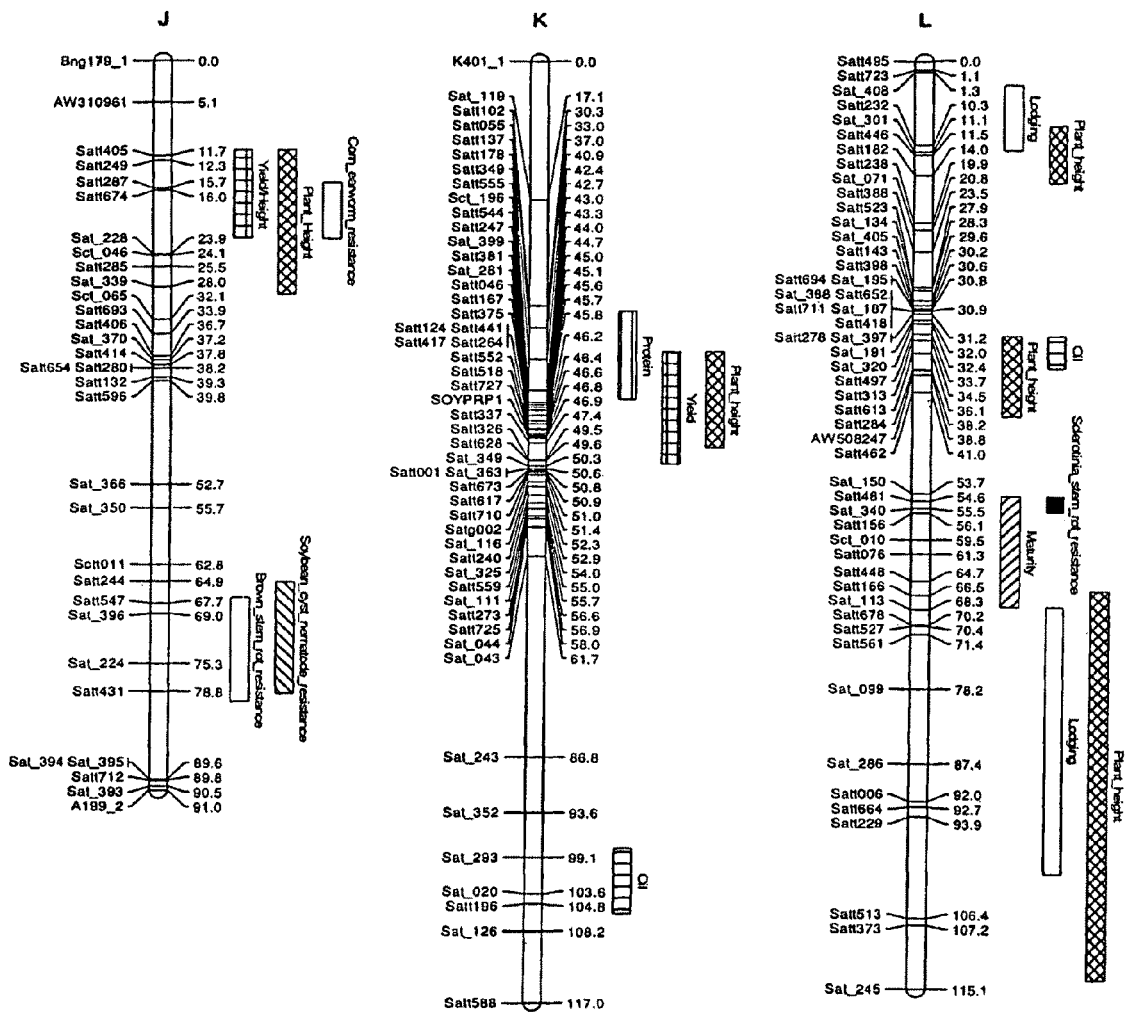
Figure 16F:
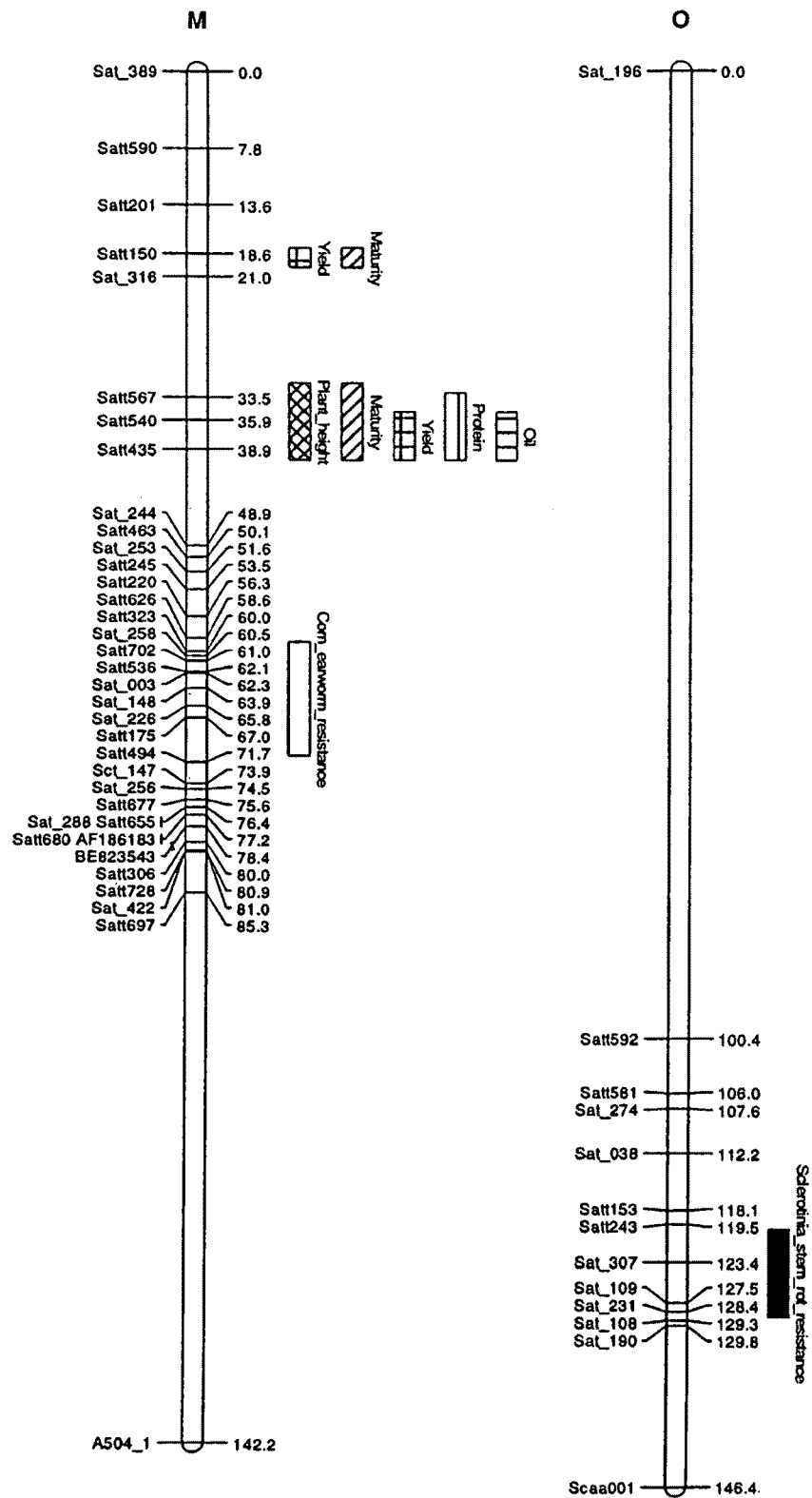

One consensus region, 16-21 cM on LG F, was found to contain a QTL for partial resistance to *Phytophthora* root rot in three mapping populations developed from four mapping parents (Tables A-G and FIG. 14). Two consensus regions, 120-133 cM on LG C2 and 0-3 cM on LG G, were found to contain QTLs for resistance to sudden death syndrome in two mapping populations developed from four mapping parents (Table 1 and FIG. 14). A consensus region, 67-80 cM on LG J, was found to contain a QTL for resistance to brown stem rot in three mapping populations developed from six mapping parents (Tables A-G and FIG. 14).

QTLs for *Sclerotinia* stem rot resistance were found in seven consensus regions on seven LGs: A2, D1a, D1b, F, G, L, and O (Tables A-G and FIG. 14). The near 60-62 cM region on LG A2 and the 120-129 cM region on LG O were each identified in three mapping populations developed from four mapping parents (Tables A-G). The regions near 109-110 cM on LG D1a, near 118-120 cM on LG D1b, near 63-65 cM on LG F, 85-98 cM on LG G, and near 54-56 cM on LG L were each identified in two mapping population developed from three mapping parents (Tables A-G).

QTLs for corn earworm resistance were found in five consensus regions on five LGs: C2, E, H, J and M (Tables A-G and FIG. 14). The regions 90-113 cM on LG C2, 2-10 cM on LG E, 15-22 cM on LG J, and 59-71 cM on LG M were each identified in two mapping populations developed from three or four mapping parents (Tables A-G). The 49-61 cM region on LG H was identified in three mapping populations developed from four mapping parents (Tables A-G).

Consensus QTL Regions Containing QTLs for Multiple Traits

Figure 2:
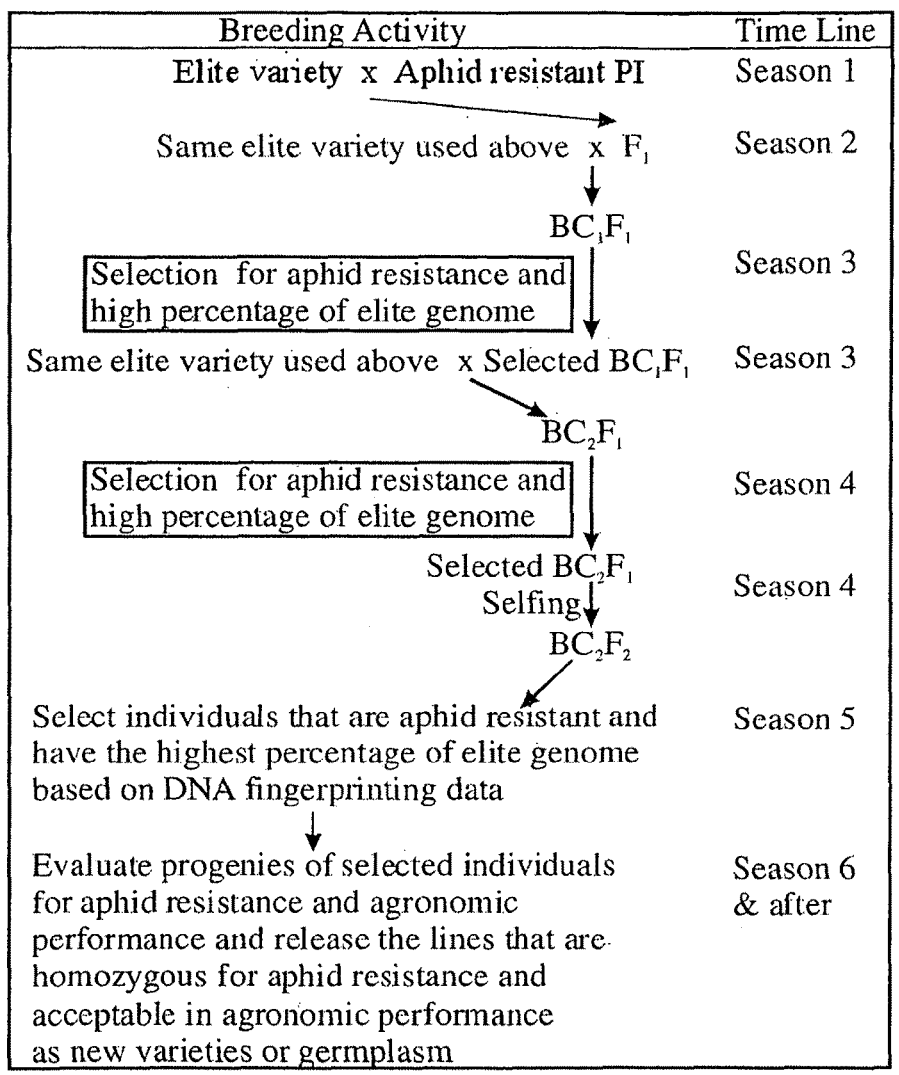
FIG. 2 shows an exemplary illustration of a general method to transfer the aphid resistance from the aphid resistant PIs to elite soybean germplasm.
Figure 5:
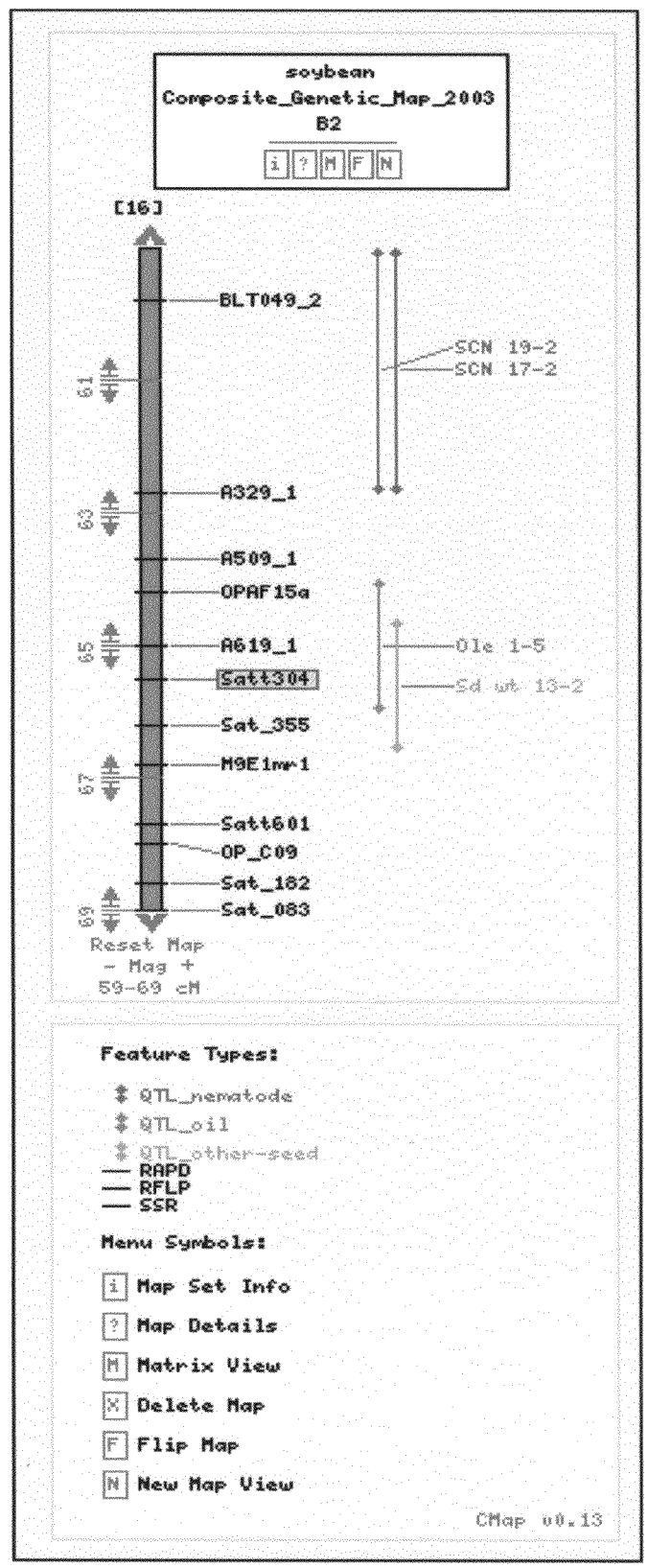
FIG. 5 shows exemplary Satt304 marker information of Linkage Group B2 in association to aphid resistant germplasm.
Figure 6:
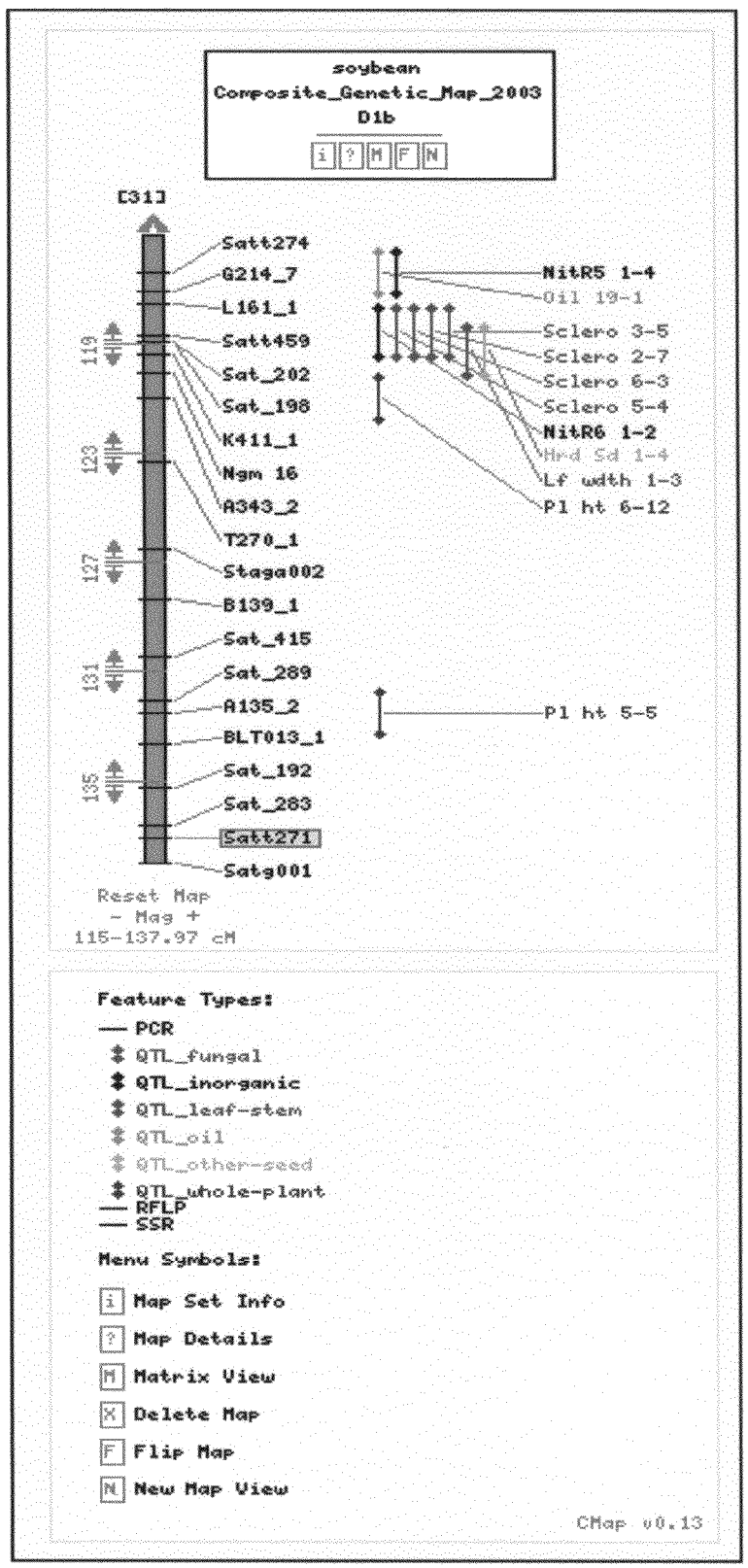
FIG. 6 shows exemplary Satt271 marker information associating Linkage Group D1b in association to aphid resistant germplasm.
Figure 7:
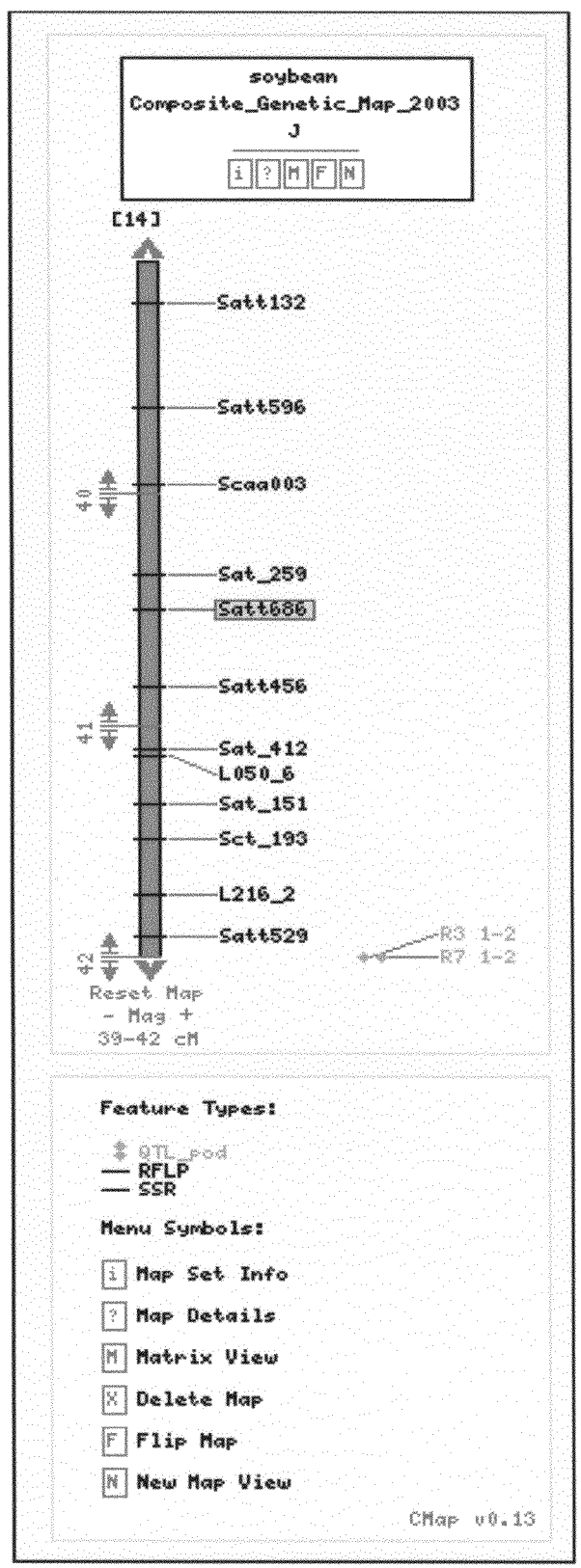
FIG. 7 shows exemplary Satt280 marker information associating Linkage Group J with aphid resistant germplasm.
Figure 8:
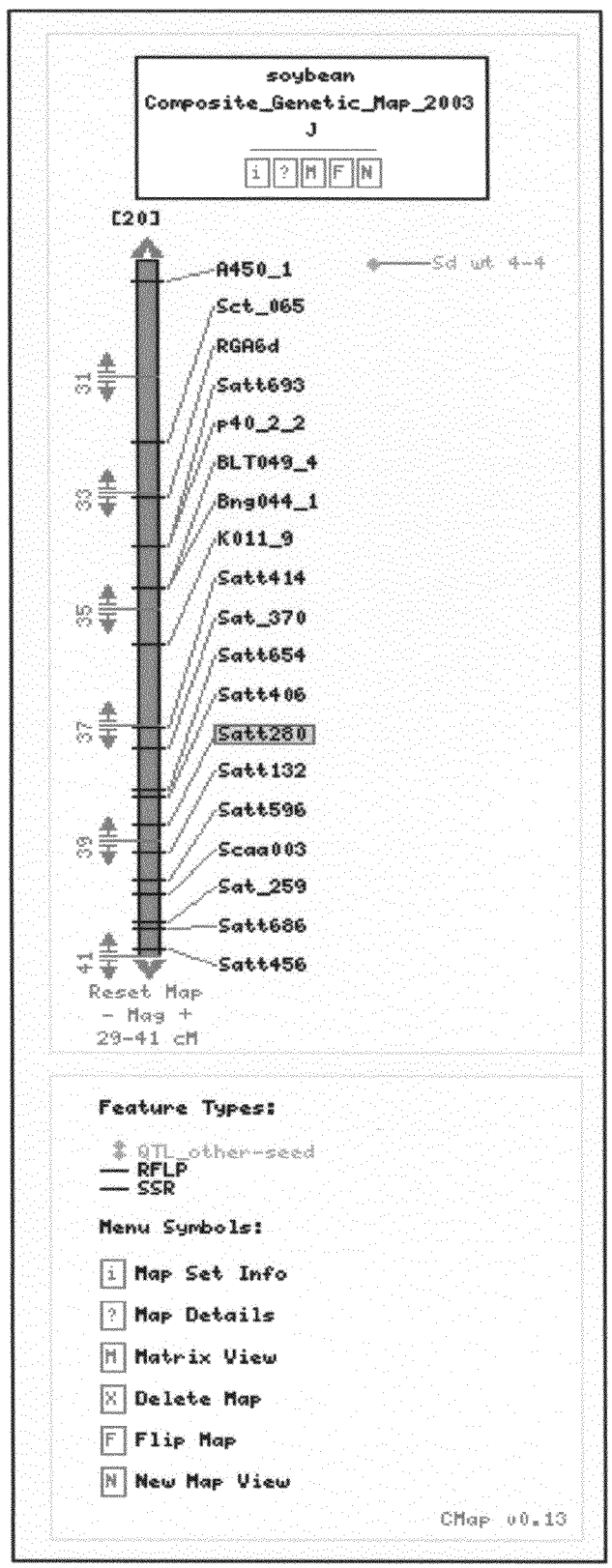
FIG. 8 shows exemplary Satt529 marker information associating Linkage Group J with aphid resistant germplasm.
Figure 9:
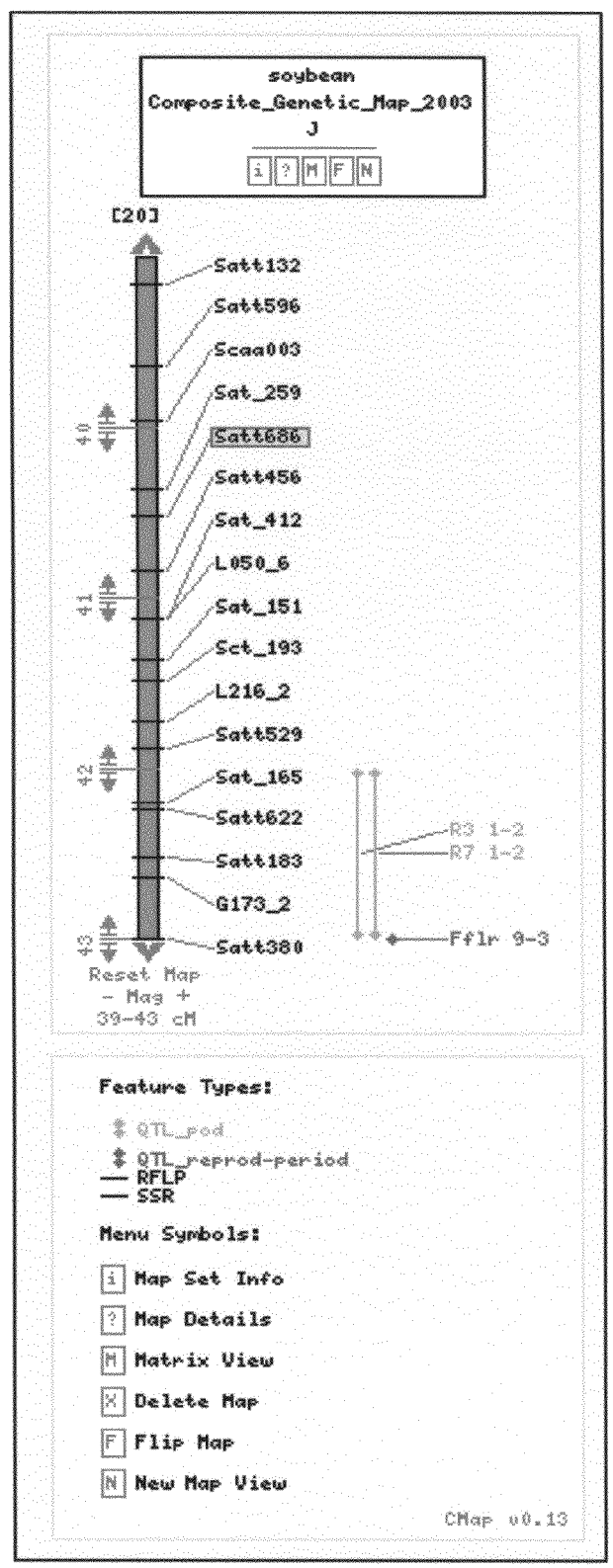
FIG. 9 shows exemplary rSatt686 marker information associating Linkage Group J with aphid resistant germplasm.
Figure 10:
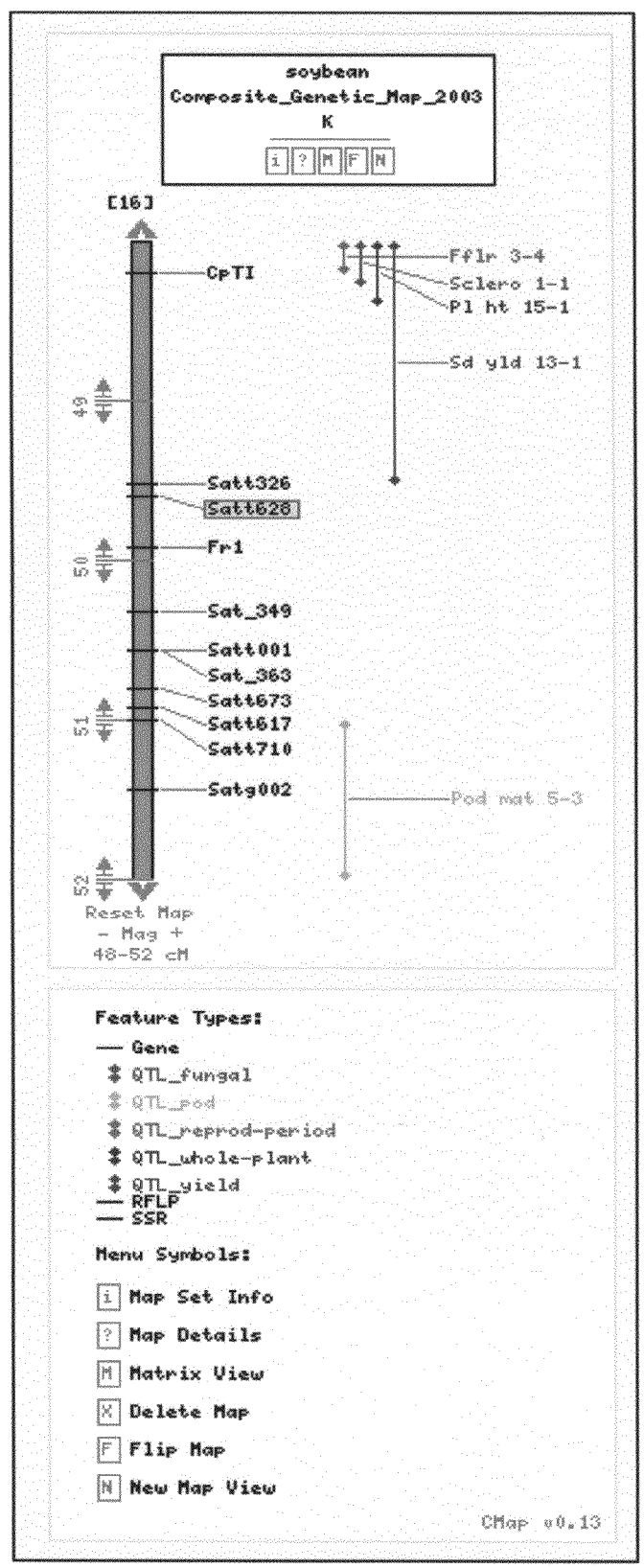
FIG. 10 shows exemplary Satt628 marker information associating Linkage Group K with aphid resistant germplasm.
Figure 11:
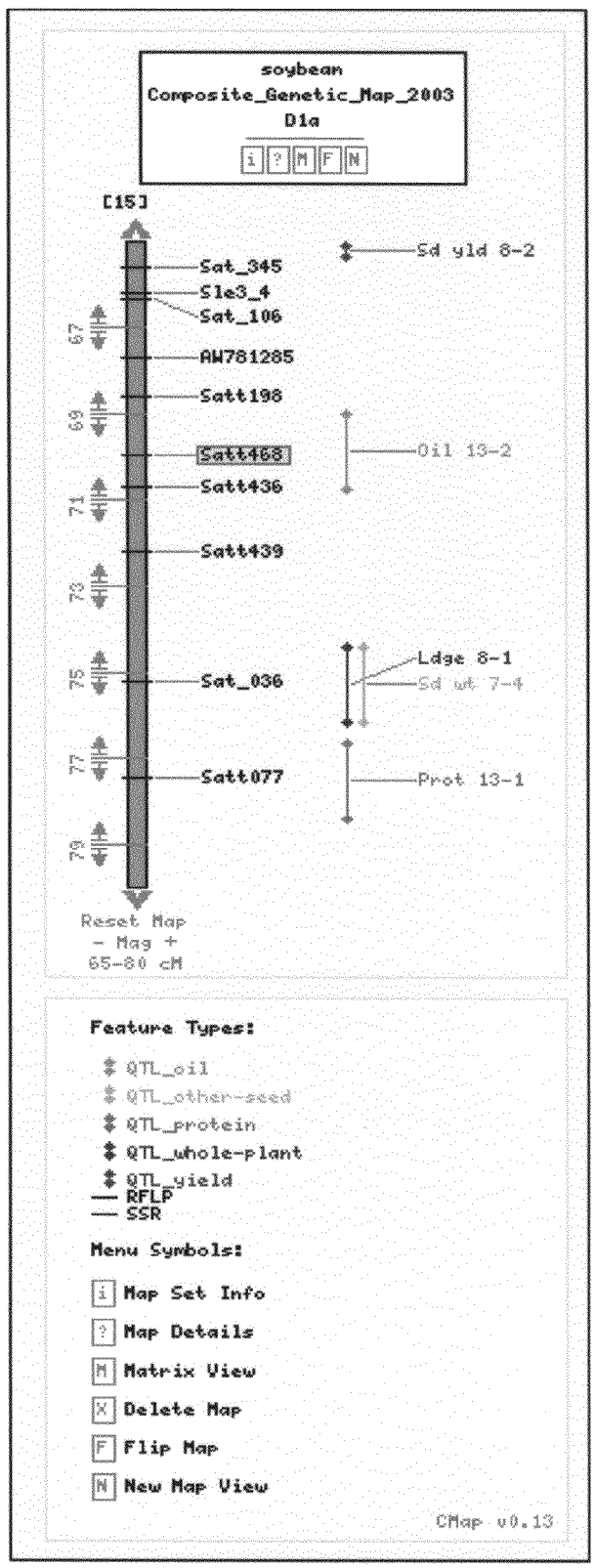
FIG. 11 shows exemplary Satt468 marker information associating Linkage Group D1a with aphid resistant germplasm.
Figure 12:
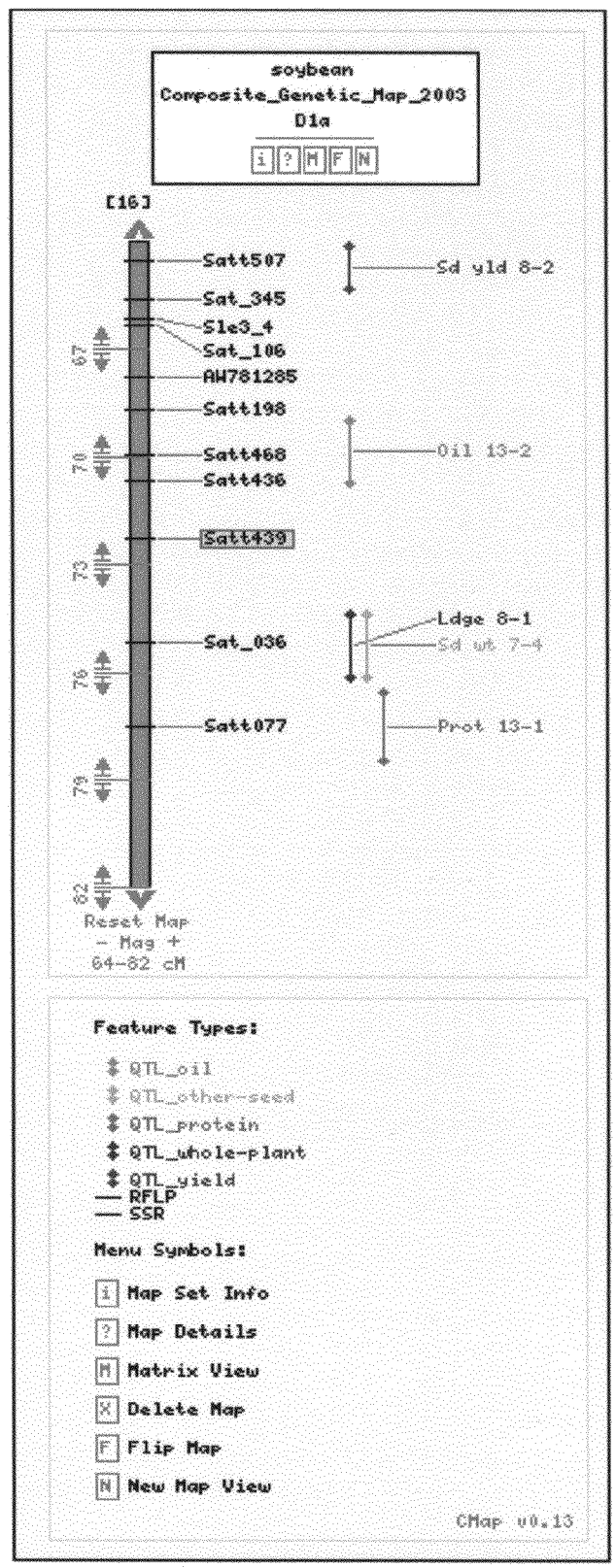
FIG. 12 shows exemplary Satt439 marker information associating Linkage Group D1a with aphid resistant germplasm.

In QTL mapping studies, it is common to find QTLs for different traits mapped to a common genomic region. In many cases, the traits affected by the co-localized QTLs are correlated, while in other cases, the trait correlation may not be obvious. While it remains to be resolved whether the co-localized QTLs are tightly linked QTLs or the same QTL with pleiotropic effects, it is useful to document the genomic regions containing QTLs for multiple traits. When the consensus QTL regions for each trait were compared, over 20 genomic regions were found containing QTLs for multiple traits (Table 1 and FIG. 14). Five genomic regions, 88-96 cM on LG A1, near 9-11 cM on LG C1, 26-36 cM on LG E, 31-40 cM on LG I, and 35-40 cM on LG M contain QTLs for both seed protein and seed oil contents (FIG. 14). Soybean protein content and oil content are highly negatively correlated with a correlation coefficient as high as $-0.98$ ($P<0.001$) (Mansur et al. 1996). It is, therefore, expected to have some QTLs for the two traits mapped to common genomic regions. Four genomic regions, near 34-36 cM on LG I, 15-22 cM on LG J, 36-42 cM on LG K, and 35-40 cM on LG M, contain QTLs for both yield and plant height (FIG. 2). Yield was correlated ($r=0.59$, $P<0.001$) with plant height in the study by Mansur et al. (1996). Yield was also correlated ($r=0.48$, $P<0.001$) with maturity (Mansur et al. 1996). Three genomic regions, near 34-36 cM on LG I, near 18-20 cM on LG M, and 35-40 cM on LG M, contain QTLs for both yield and maturity (FIG. 2). Yield was negatively correlated ($r=-0.58$, $P<0.001$) with protein content and positively correlated ($r=0.60$, $P<0.001$) with oil content (Mansur et al. 1996). Two genomic regions, near 34-36 cM on LG I and 35-40 cM on LG M, contain QTLs for yield, protein content, and oil content. Another region, 36-42 cM on LG K, contains QTLs for yield and protein content (FIG. 2). Lodging was highly correlated with plant height (r=0.84, P<0.001) (Mansur et al. 1996). Three genomic regions, 107-113 cM on LG C2, 8-11 cM on LG L, and 68-101 cM on LG L, contain QTLs for these two traits (FIG. 2).

QTLs for *Sclerotinia* stem rot resistance were co-localized with QTLs for plant height near 120 cM on LG D1b and near 65 cM on LG F, for maturity near 54-56 cM on LG L, for SCN resistance near 60-62 cM on LG A2, and for protein content in 89-98 cM on LG G (FIG. 2). *Sclerotinia* stem rot disease severity index was correlated with plant height (r=0.54, P<0.001) and maturity (r=0.67, P<0.001) in the study by Kim and Diers (2000). Shorter plant and earlier maturity were associated with greater resistance to *Sclerotinia* stem rot, which was considered an escape mechanism (Kim and Diers 2000). However, the QTLs co-localized with plant height on LG D1b and LG F and with maturity on LG L were for physiological resistance to *Sclerotinia* stem rot (Arahana et al. 2001). Therefore, the resistance associated with shorter plant and earlier maturity may also involve physiological resistance. A significant correlation (r=0.40, P<0.05) between *Sclerotinia* stem rot disease severity index and protein content was reported by Hoffman et al. (1998). There is no report of any correlation between *Sclerotinia* stem rot resistance and SCN resistance.

QTLs for SCN resistance were co-localized with QTLs for sudden death syndrome (SDS) near 4-6 cM on LG G, for brown stem rot resistance in 67-79 cM on LG J, for oil content in 33-36 cM on LG E, and for *Sclerotinia* stem rot resistance as described above. Coinheritance of SDS resistance with SCN resistance was reported by Chang et al. (1997) and the locus underlying the coinheritance was assigned to the region on LG G where the major SCN resistance was located (Chang et al. 1997). The region on LG J is known to contain multiple resistance genes to different pathogens (Bachman et al. 2001). Correlation of SCN resistance with oil content was not reported in the literature. Qiu et al. (1999) carried out a QTL mapping study in a population that was segregating for both SCN resistance and oil content. A marker on LG H was found to be associated with both SCN resistance and oil content.

QTLs for corn earworm resistance were co-localized with QTLs for plant height in 107-113 cM on LG C2 and in 15-22 cM on LG J. There is no known correlation between corn earworm resistance and plant height in soybean.

Future Opportunities for QTL Discovery in Soybean Germplasm.

Over a thousand SNP markers were recently added to the integrated soybean linkage map (Choi et al. 2007) and research is ongoing to add several more thousands of SNP markers to the map. High-throughput SNP genotyping systems have been developed and are commercially available. For example, the Illumina BeadStation 500 (Shen et al. 2005) can analyze 1536 SNP loci in parallel in 192 DNA samples in three days. The addition of thousands of SNP markers to the integrated linkage map and the availability of high-throughput SNP genotyping systems will significantly reduce the time needed to genotype mapping populations and accelerate QTL discovery in soybean.

The first draft sequence of the whole soybean genome was released in 2008 (JGI 2008). The availability of a whole genome sequence will allow scientists to fine-map QTLs and eventually pinpoint the specific mutations that cause the phenotypic variations.

The development of new statistical approaches and computer software that allow joint analysis of multiple populations will also increase the power to identify real QTLs, especially QTLs with small effects. Bink et al. (2008) developed a pedigree-based approach that jointly analyzes the data from multiple populations that are related through their common ancestors in the pedigree. This approach is currently implemented in the computer software FlexQTL™. Jourjon et al. (2005) developed a computer software package, MCQTL, that can perform QTL mapping in multi-cross designs.

The major limitation to QTL discovery in soybean is the difficulty in obtaining accurate measurement of the traits with low heritability. For certain traits such as field resistance to *Sclerotinia* stem rot, reliable measurement is difficult to obtain even with efforts to provide the optimum conditions to induce the disease. Large experiments with multiple locations in multiple years are often required to obtain the phenotypic data.

Consensus QTL Regions in Soybean

Using the integrated linkage map developed by Song et al. (2004) as a reference map, when QTLs identified in different mapping populations for the same trait are less than 10 cM from one another, the region containing these QTLs can be considered a consensus QTL region for the trait. These consensus QTL regions are used to determine the true location of the QTL. Tables A-G and FIG. 14 summarize the consensus QTL regions for each trait based on the QTL data collected in SoyBase. The chromosome length in cm (centimorgan) generally covered by a single marker associated with a QTL on the consensus map, is contemplated as an arbitrary 2 cM interval with 1 cM on either side of the marker defined as the QTL region, for example, as shown for QTL mapping in SoyBase. Thus the true QTL position (i.e. the actual gene (DNA sequence) controlling the mapped trait) may be outside the arbitrary 2 cM region. For use in the present inventions the arbitrary 2 cM region was used for each marker, such that the actual region identified by the markers of the present inventions may extend at least 1 cM before and after the most distant areas identified, for example, in Tables X1-X2, FIG. 14, preferably 10 cM before and after the most distant areas identified herein. Another example of determining the location of a true QTL position is shown in Table X and in the text for other Soybean QTLs, for example, the true QTL may be in a position at least 1 cM before the start position and 1 cM after the end position.

TABLE G

Consensus regions for QTLs Soybean QTLs that were less than 10 cM apart but were identified in different populations for the same trait.

| Trait/QTL | LG[a] | Start position[b] | End position[b] | Mapping parent 1 | Mapping parent 2 | Reference |
|---|---|---|---|---|---|---|
| Yield | | | | | | |
| Sd yld 11-1 | C2 | 39 | 41 | Minsoy | Noir 1 | Specht et al. (2001) |
| Yld/SW 2-2 | C2 | 45 | 47 | Archer | Noir 1 | Orf et al. (1999b) |
| Sd yld 15-1 | C2 | 97 | 99 | BSR 101 | LG82-8379 | Kabelka et al. (2004) |
| Sd yld 5-1 | C2 | 107 | 109 | Archer | Noir 1 | Orf et al. (1999b) |

TABLE G-continued

Consensus regions for QTLs Soybean QTLs that were less than 10 cM apart but were identified in different populations for the same trait.

| Trait/QTL | LG[a] | Start position[b] | End position[b] | Mapping parent 1 | Mapping parent 2 | Reference |
|---|---|---|---|---|---|---|
| Yld/Ht 2-1 | C2 | 107 | 109 | Archer | Minsoy | Orf et al. (1999b) |
| Sd yld 16-3 | C2 | 112 | 114 | IA2008 | PI 468916 | Wang et al. (2004a) |
| Sd yld 3-2 | C2 | 117 | 119 | PI 27890 | PI 290136 | Mansur et al. (1996) |
| Yld/Ht 4-2 | C2 | 117 | 119 | Minsoy | Noir 1 | Orf et al. (1999b) |
| Sd yld 5-2 | D2 | 47 | 49 | Archer | Noir 1 | Orf et al. (1999b) |
| Yld/Ht 2-4 | D2 | 53 | 55 | Archer | Minsoy | Orf et al. (1999b) |
| Sd yld 10-1 | I | 31 | 33 | Parker | PI 468916 | Yuan et al. (2002) |
| Sd yld 9-1 | I | 34 | 36 | A81356022 | PI 468916 | Yuan et al. (2002) |
| Sd yld 14-1 | I | 36 | 37 | A3733 | PI 437088A | Chung et al. (2003) |
| Yld/Ht 4-1 | J | 11 | 13 | Minsoy | Noir 1 | Orf et al. (1999b) |
| Yld/Ht 1-3 | J | 20 | 22 | PI 27890 | PI 290136 | Mansur et al. (1996) |
| Sd yld 16-1 | K | 36 | 38 | IA2008 | PI 468916 | Wang et al. (2004a) |
| Sd yld 12-1 | K | 46 | 47 | Essex | Forrest | Yuan et al. (2002) |
| Sd yld 13-1 | K | 47 | 50 | Flyer | Hartwig | Yuan et al. (2002) |
| Sd yld 8-1 | L | 70 | 72 | Archer | Minsoy | Orf et al. (1999a) |
| Sd yld 11-6 | L | 88 | 90 | Minsoy | Noir 1 | Specht et al. (2001) |
| Yld/Ht 1-1 | L | 91 | 93 | PI 27890 | PI 290136 | Mansur et al. (1996) |
| Yld/Ht 3-1 | L | 94 | 96 | Archer | Noir 1 | Orf et al. (1999b) |
| Sd yld 6-1 | M | 18 | 20 | Minsoy | Noir 1 | Orf et al. (1999b) |
| Yld/Ht 2-2 | M | 18 | 20 | Archer | Minsoy | Orf et al. (1999b) |
| Yld/SW 1-1 | M | 35 | 37 | Archer | Minsoy | Orf et al. (1999b) |
| Sd yld 3-1 | M | 38 | 40 | PI 27890 | PI 290136 | Mansur et al. (1996) |
| Protein content | | | | | | |
| Prot 2-1 | A1 | 93 | 95 | PI 27890 | PI 290136 | Mansur et al. (1996) |
| Prot 12-1 | A1 | 94 | 96 | Minsoy | Noir 1 | Specht et al. (2001) |
| Prot 21-1 | A2 | 145 | 147 | BSR 101 | LG82-8379 | Kabelka et al. (2004) |
| Prot 14-1 | A2 | 149 | 151 | M91-212006 | SZG9652 | Vollmann et al. (2002) |
| Prot 3-2 | B1 | 28 | 30 | A87296011 | C1763 | Brummer et al. (1997) |
| Prot 16-1 | B1 | 35 | 37 | Essex | Williams | Chapman et al. (2003) |
| Prot 4-11 | B2 | 28 | 30 | PI 416937 | Young | Lee et al. (1996b) |
| Prot 1-6 | B2 | 32 | 34 | A81356022 | PI 468916 | Diers et al. (1992) |
| Prot 4-10 | B2 | 43 | 46 | PI 416937 | Young | Lee et al. (1996b) |
| Prot 9-2 | C1 | 9 | 11 | Minsoy | Noir 1 | Orf et al. (1999b) |
| Prot 4-4 | C1 | 20 | 22 | PI 416937 | Young | Lee et al. (1996b) |
| Prot 12-2 | C1 | 32 | 34 | Minsoy | Noir 1 | Specht et al. (2001) |
| Prot 3-3 | C1 | 90 | 92 | A87296011 | C1763 | Brummer et al. (1997) |
| Prot 4-3 | C1 | 96 | 98 | PI 416937 | Young | Lee et al. (1996b) |
| Prot 21-2 | C1 | 123 | 125 | BSR 101 | LG82-8379 | Kabelka et al. (2004) |
| Prot 4-2 | C1 | 126 | 128 | PI 416937 | Young | Lee et al. (1996b) |
| Prot 17-1 | C2 | 117 | 119 | Essex | Williams | Hyten et al. (2004) |
| Prot 13-2 | C2 | 121 | 123 | Ma. Belle | Proto | Csanadi et al. (2001) |
| Prot 4-6 | E | 26 | 28 | PI 416937 | Young | Lee et al. (1996b) |
| Prot 3-6 | E | 30 | 32 | A87296011 | C1763 | Brummer et al. (1997) |
| Prot 18-1 | E | 30 | 32 | Coker 237 | PI 97100 | Fasoula et al. (2004) |
| Prot 1-8 | G | 89 | 91 | A81356022 | PI 468916 | Diers et al. (1992) |
| Prot 3-10 | G | 96 | 98 | A87296011 | C1763 | Brummer et al. (1997) |
| Prot 11-1 | I | 31 | 33 | Parker | PI 468916 | Yuan et al. (2002) |
| Prot 1-3 | I | 31 | 33 | A81356022 | PI 468916 | Diers et al. (1992) |
| Prot 3-12 | I | 31 | 33 | A87296011 | C1763 | Brummer et al. (1997) |
| Prot 10-1 | I | 34 | 36 | A81356022 | PI 468916 | Yuan et al. (2002) |
| Prot 15-1 | I | 36 | 37 | A3733 | PI 437088A | Chung et al. (2003) |
| Prot 1-2 | I | 38 | 40 | A81356022 | PI 468916 | Lark et al. (1994) |
| Prot 5-4 | K | 31 | 33 | Coker237 | PI 97100 | Lee et al. (1996b) |
| Prot 12-3 | K | 40 | 42 | Minsoy | Noir 1 | Specht et al. (2001) |
| Prot 12-4 | M | 33 | 35 | Minsoy | Noir 1 | Specht et al. (2001) |
| Prot 13-3 | M | 33 | 35 | Ma. Belle | Proto | Csanadi et al. (2001) |
| Prot 7-1 | M | 38 | 40 | Archer | Minsoy | Orf et al. (1999b) |
| Oil content | | | | | | |
| Oil 8-1 | A1 | 88 | 90 | Archer | Minsoy | Orf et al. (1999b) |
| Oil 4-3 | A1 | 91 | 93 | A87296011 | C1763 | Brummer et al. (1997) |
| Oil 3-2 | A1 | 93 | 95 | PI 27890 | PI 290136 | Mansur et al. (1996) |
| Oil 13-1 | A1 | 94 | 96 | Minsoy | Noir 1 | Specht et al. (2001) |
| Oil 9-1 | C1 | 9 | 11 | Archer | Noir 1 | Orf et al. (1999b) |
| Oil 8-2 | C1 | 9 | 11 | Archer | Minsoy | Orf et al. (1999b) |
| Oil 5-1 | E | 23 | 25 | PI 416937 | Young | Lee et al. (1996b) |
| Oil 2-9 | E | 34 | 36 | A81356022 | PI 468916 | Diers et al. (1992) |
| Oil 17-2 | H | 86 | 88 | Coker 237 | PI 97100 | Fasoula et al. (2004) |
| Oil 19-2 | H | 89 | 91 | N87-984-16 | TN93-99 | Panthee et al. (2005) |
| Oil 14-3 | I | 22 | 24 | Ma. Belle | Proto | Csanadi et al. (2001) |
| Oil 12-1 | I | 31 | 33 | Parker | PI 468916 | Yuan et al. (2002) |
| Oil 11-1 | I | 31 | 33 | A81356022 | PI 468916 | Yuan et al. (2002) |
| Oil 13-4 | I | 34 | 36 | Minsoy | Noir 1 | Specht et al. (2001) |

TABLE G-continued

Consensus regions for QTLs Soybean QTLs that were less than 10 cM apart but were identified in different populations for the same trait.

| Trait/QTL | LG[a] | Start position[b] | End position[b] | Mapping parent 1 | Mapping parent 2 | Reference |
|---|---|---|---|---|---|---|
| Oil 15-1 | I | 36 | 37 | A3733 | PI 437088A | Chung et al. (2003) |
| Oil 2-2 | I | 38 | 40 | A81356022 | PI 468916 | Diers et al. (1992) |
| Oil 4-11 | K | 98 | 100 | A87296011 | C1763 | Brummer et al. (1997) |
| Oil 14-2 | K | 104 | 106 | Ma. Belle | Proto | Csanadi et al. (2001) |
| Oil 18-2 | L | 34 | 36 | PI 416937 | Young | Fasoula et al. (2004) |
| Oil 2-7 | L | 36 | 38 | A81356022 | PI 468916 | Diers et al. (1992) |
| Oil 5-3 | L | 36 | 38 | PI 416937 | Young | Lee et al. (1996b) |
| Oil 3-1 | L | 91 | 93 | PI 27890 | PI 290136 | Mansur et al. (1996) |
| Oil 16-1 | L | 93 | 95 | Essex | Williams | Hyten et al. (2004) |
| Oil 9-3 | L | 94 | 96 | Archer | Noir 1 | Orf et al. (1999b) |
| Oil 16-2 | M | 35 | 37 | Essex | Williams | Hyten et al. (2004) |
| Oil/Prot 1-2 | M | 38 | 40 | PI 27890 | PI 290136 | Lark et al. (1994) |

[a]LG = linkage group. The linkage group names are from the integrated map by Song et al. (2004).
[b]The start positions and end positions are from the integrated map by Song et al. (2004). When only a single marker that was associated with a QTL in a published study could be placed on the consensus map, an arbitrary 2 cM interval with 1 cM on either side of the marker was defined as the QTL region in SoyBase

SUMMARY

The inventors used 123 SSR markers and a subset of 94 soybean lines, for the construction of a linkage map of 25 linkage groups, which covered the majority of the soybean genome except for some regions where no polymorphic markers were found in this study. For LGs A2, B2, F, L, M, each LG was consisting of two unlinked segments. Based on the consensus map (Song et al. 2004); the intervals between two unlinked segments were about 30 cM or more. These intervals are contemplated to be exaggerated due to the small size of the subset. Since there were no polymorphic SSR loci in these intervals for this study, it was difficult to connect these unlinked segments. Three markers, Satt194 (LG C1), Sat.sub 130 (LG C2), and Satt353 (LG H), were unlinked because of the lack of polymorphic loci around them. These three markers are about 46 cM, 59 cM, and 56 cM away from the rest of mapped markers in this study based on the soybean consensus map (Song et al. 2004), respectively. Additionally, the top half of the LG E had no polymorphic markers (about 40 cM). In this study, a subset of lines was used to perform the whole genome scan first, which saved a large amount of time and resources. The maps for LGs F and M constructed using the whole population were similar to the maps using the subset of 94 lines (FIG. 14), which indicates the effectiveness of the subset of lines used in this study.

In this study, two QTLs for controlling the aphid resistance in PI 567541B were identified using a mapping population that was inoculated with either the natural mixed aphids in the Field trial or the single-clone aphid in the green house two unlinked segments. Based on the consensus map (Song et al. 2004); the intervals between two unlinked segments were about 30 cM or more. These intervals could be exaggerated due to the small size of the subset. Since there were no polymorphic SSR loci in these intervals for this study, it was difficult to connect these unlinked segments. Three markers, Satt194 (LG C1), Sat 130 (LG C2), and Satt353 (LG H), were unlinked because of the lack of polymorphic loci around them. These three markers are about 46 cM, 59 cM, and 56 cM away from the rest of mapped markers in this study based on the soybean consensus map (Song et al. 2004), respectively. Additionally, the top half of the LG E had no polymorphic markers (about 40 cM).

In this study, two QTLs for controlling the aphid resistance in PI 567541B were identified using a mapping population that was inoculated with either the natural mixed aphids in the Field trial or the single-clone aphid in the explained a large portion of the phenotypic variation. This major QTL was tightly linked to marker Satt299, which has not been mapped before. In this study, Satt299 was only about 3 cM away from Satt435, which was the closely linked marker for the aphid resistance genes identified in Dowling and Jackson (Li et al. 2007). Thus, the major QTL identified in this study is coincidentally located in a similar genomic region as the resistance genes in Dowling and Jackson, which indicates that they are either allelic at the same locus or different genes, but tightly linked to each other. Kim et al. (2008) recently found that PI 567541B was resistant to the aphids from Ohio while both Dowling and Jackson were susceptible. Our results suggest that the better resistance of PI 567541B compared with Dowling and Jackson could be due to one or more of the following three factors: (1) the existence of the other resistance gene, (2) a different resistance allele conferring better resistance at the same locus on LG M as the resistance genes in Dowling and Jackson, and (3) a new resistance locus conferring better resistance on LG M that is closely linked to the resistance genes in Dowling and Jackson. Understanding the allelic relationship between the major QTL in PI 567541B and the resistance genes found in Dowling and Jackson could be important for soybean breeders to determine if these genes from different resistance sources can be pyramided. However, an allelic test using progenies from the cross of PI 567541B by Dowling or Jackson might not resolve the question because of the confounding effects of the additional resistance gene in PI 567541B and its interaction with the major gene. Therefore, fine mapping or gene cloning might be necessary to determine their allelic relationship.

The other QTL was identified on LG F in this study and had a smaller effect than the one on LG M. Aphid or other insect resistance genes have not been reported in that region yet, but a QTL for leaf phosphorus content was reported at a similar region (Li et al. 2005). The relationship between leaf phosphorus content and soybean aphid resistance is unknown. However, potassium content in leaf has been related to the soybean aphid resistance in several studies (Myers et al. 2005; Myers and Gratton 2006; Walter and Difonzo 2007), which concluded that the deficiency of potassium could increase the reproduction of the soybean aphid. Phosphorus is an essential element for all the living cells; therefore, it is possible that the deficiency of phosphorus in leaf tissues might also affect the soybean aphid. Interestingly, in the greenhouse trial, the QTL on LG F only explained very little phenotypic variation while the major QTL on LG M explained the majority of the genetic variation (over 94%). Most likely the aphid resistance in PI 567541B in the greenhouse trial is mainly controlled by a single gene, the major QTL on LG M. Although the QTL on LG F had very little affect in the greenhouse trial, it was detected and validated in the Field trials. This QTL even explained a relatively large portion of the phenotypic variation in the Field trial, over 25% for the 4-week rating in either mapping or validation population. This indicates that the QTL on LG F might be critical in the Field resistance. The two QTLs combined with their interaction explained the majority of the phenotypic variation in the Field trial. Thus, the aphid resistance in PI 567541B might be mainly controlled by these two genes under the Field conditions. Therefore, this study demonstrates that the two resistance genes in PI 567541B were expressed differently in the Field and greenhouse trials. Only the major gene on LG M was needed for providing aphid resistance in the greenhouse trial while both genes were required in the Field trial. This difference might be due to the different inoculum used in the trials. The aphids used in the greenhouse trial were a single clone aphid, which was collected from the Field in 2002 and maintained in the greenhouse thereafter. In contrast, the aphids used in the Field trial were a mixture of the natural aphids collected from the infested Fields during the year of the Field trial. It is possible that the aphids used in the Field trials had a different biotype, which caused different reactions of the resistance genes in PI 567541B.

Recently, Kim et al. (2008) reported a new soybean aphid biotype in Ohio, which has overcome the resistance genes in Dowling and Jackson. In 2006, Dowling was also found susceptible to aphids in the Field while PI 567541B was resistant (Mensah et al. 2007). This might be evidence of a new soybean aphid biotype occurrence in the Fields of Michigan. This study was the First to map genes conferring resistance to mixed natural aphids using a Field trial. Our results indicate that the QTL on LG F might have played an important role in providing resistance to an unknown new aphid biotype in Michigan. However, further investigation is warranted to determine the role of the QTL on LG F in the Field aphid resistance.

Evaluation of aphid resistance usually requires artificial infestation, which is laborious and time consuming. The infestation of aphid might also be complicated by the environmental conditions, such as heavy rainfalls and strong winds. Marker-assisted selection (MAS) can be a useful and powerful tool for breeders to select aphid resistance lines even without the aphid infestation. The two aphid resistance QTLs identified in PI 567541B could be ready for MAS since they have been validated in different genetic backgrounds in this study. Moreover, the resistance genes found in PI 567541B may confer broader resistance to various biotypes of aphids than the ones in Dowling and Jackson because PI 567541B provides resistance to some new aphid biotypes that have overcome the resistance in Dowling and Jackson (Kim et al. 2008; Mensah et al. 2007).

The following references are herein incorporated by reference.

Akkaya M S, Shoemaker R C, Specht J E, Bhagwat A A, Cregan P B (1995) Integration of simple sequence DNA markers into a soybean linkage map. Crop Sci 35:1439-1445

Apuya N R, Frazier B L, Keim P, Roth E J, Lark K G (1988) Restriction fragment length polymorphisms as genetic markers in soybean, *Glycine max* (L.) Merrill. Theor Appl Genet. 75:889-901

Arahana V S, Graefa G L, Spechta J E, Steadmanb J R, Eskridgec K M (2001) Identification of QTLs for resistance to *Sclerotinia sclerotiorum* in soybean. Crop Sci 41:180-188

Bachman M S, Tamulonis J P, Nickell C D, Bent A F (2001) Molecular markers linked to brown stem rot resistance genes, Rbs1 and Rbs2, in soybean. Crop Sci 41:527-535

Bink M C A M, Boer M P, ter Braak C J F, Jansen J, Voorrips R E, van de Weg W E (2008) Bayesian analysis of complex traits in pedigreed plant populations. Euphytica 161:85-96

Brucker E, Carlson S, Wright E, Niblack T, Diers B (2005) Rhg1 alleles from soybean PI 437654 and PI 88788 respond differentially to isolates of *Heterodera glycines* in the greenhouse. TAG Theoretical and Applied Genetics 111:44-49

Brummer E C, Graef G L, Orf J, Wilcox J R, Shoemaker R C (1997) Mapping QTL for seed protein and oil content in eight soybean populations. Crop Sci 37:370-378

Burnham K D, Dorrancek A E, VanToai T T, St-Martin S K (2003) Quantitative trait loci for partial resistance to *Phytophthora sojae* in soybean. Crop Sci 43:1610-1671

Chang S J C, Doubler T W, Kilo V, Suttner R, Klein J, Schmidt M E, Gibson P T, Lightfoot D A (1996) Two additional loci underlying durable field resistance to soybean sudden death syndrome (SDS). Crop Sci 36:1684-1688

Chang S J C, Doubler T W, Kilo V Y, Abu Thredeih J, Prabhu R, Freire V, Suttner R, Klein J, Schmidt M E, Gibson P T, Lightfoot D A (1997) Association of loci underlying field resistance to soybean sudden death syndrome (SDS) and cyst nematode (SCN) race 3. Crop Sci 37:965-971

Chapman A, Pantalone V R, Ustun A, Allen F L, Landau-Ellis D, Trigiano R N, Gresshoff P M (2003) Quantitative trait loci for agronomic and seed quality traits in an F2 and F4:6 soybean population. Euphytica 129:387-393

Choi I Y, Hyten D L, Matukumalli L K, Song Q J, Chaky J M, Quigley C V, Chase K, Lark K G, Reiter R S, Yoon M S, Hwang E Y, Yi S I, Young N D, Shoemaker R C, Tassell C Pv, Specht J E, Cregan P B (2007) A soybean transcript map: gene distribution, haplotype and single-nucleotide polymorphism analysis. Genetics 176:685-696

Chung J, Babka H L, Graef G L, Staswick P E, Lee D J, Cregan P B, Shoemaker R C, Specht J E (2003) The seed protein, oil, and yield QTL on soybean linkage group I. Crop Sci 43:1053-1067

Concibido V C, Denny R L, Boutin S R, Hautea R, Orf J H, Young N D (1994) DNA marker analysis of loci underlying resistance to soybean cyst nematode (*Heterodera glycines* Ichinohe). Crop Sci 34:240-246

Concibido V C, Diers B W, Arelli P R (2004) A decade of QTL mapping for cyst nematode resistance in soybean. Crop Sci 44:1121-1131

Concibido V C, Lange D A, Denny R L, Orf J H, Young N D (1997) Genome mapping of soybean cyst nematode resistance genes in 'Peking', PI 90763, and PI 88788 using DNA markers. Crop Sci 37:258-264

Concibido V C, Young N D, Lange D A, Denny R L, Danesh D, Orf J H (1996) Targeted comparative genome analysis and qualitative mapping of a major partial-resistance gene to the soybean cyst nematode. Theor Appl Genet. 93:234-241

Cregan P B, Jarvik T, Bush A L, Shoemaker R C, Lark K G, Kahler A L, Kaya N, VanToai T T, Lohnes D G, Chung J, Specht J E (1999) An integrated genetic linkage map of the soybean genome. Crop Sci 39:1464-1490

Csanadi G, Vollmann J, Stift G, Lelley T (2001) Seed quality QTLs identified in a molecular map of early maturing soybean. Theor Appl Genet. 103:912-919

Diers B W, Keim P, Fehr W R, Shoemaker R C (1992) RFLP analysis of soybean seed protein and oil content. Theor Appl Genet. 83:608-612

Fasoula V A, Harris D K, Boerma H R (2004) Validation and designation of quantitative trait loci for seed protein, seed oil, and seed weight from two soybean populations. Crop Sci 44:1218-1225

Fu S X, Wang H, Wu J J, Liu H, Gai J Y, Yu D Y (2007) Mapping insect resistance QTLs of soybean with RIL population. Hereditas Beijing 29:1139-1143

Glover K D, Wang D, Arelli P R, Carlson S R, Cianzio S R, Diers B W (2004) Near isogenic lines confirm a soybean cyst nematode resistance gene from PI 88788 on linkage group J. Crop Sci 44:936-941

Grant D, Imsande M I, Shoemaker R C (2008) SoyBase, The USDA-ARS Soybean Genome Database. http://soybase.agron.iastate.edu. Cited 14 Jul. 2008

Guo B, Sleper D A, Arelli P R, Shannon J G, Nguyen H T (2005) Identification of QTLs associated with resistance to soybean cyst nematode races 2, 3 and 5 in soybean PI 90763. Theor Appl Genet. 111:965-971

Hoffman D D, Hartman G L, Mueller D S, Leitz R A, Nickell C D, Pedersen W L (1998) Yield and seed quality of soybean cultivars infected with *Sclerotinia sclerotiorum*. Plant Dis 82:826-829

Hyten D L, Pantalone V R, Sams C E, Saxton A M, Landau-Ellis D, Stefaniak T R, Schmidt M E (2004) Seed quality QTL in a prominent soybean population. Theor Appl Genet. 109:552-561

JGI (2008) Phytozome: *Glycine max*. http://www.phytozome.net/soybean. Cited 14 Jul. 2008

Jourjon M F, Jasson S, Marcel J, Ngom B, Mangin B (2005) MCQTL: multi-allelic QTL mapping in multi-cross design. Bioinformatics (Oxford) 21:128-130

Kabelka E A, Diers B W, Fehr W R, LeRoy A R, Baianu I C, You T, Neece D J, Nelson R L (2004) Putative alleles for increased yield from soybean plant introductions. Crop Sci 44:784-791

Keim P, Diers B W, Olson T C, Shoemaker R C (1990a) RFLP mapping in soybean: association between marker loci and variation in quantitative traits. Genetics 126:735-742

Keim P, Diers B W, Shoemaker R C (1990b) Genetic analysis of soybean hard seededness with molecular markers. Theor Appl Genet. 79:465-469

Keim P, Schupp J M, Travis S E, Clayton K, Zhu T, Shi L, Ferreira A, Webb DM (1997) A high-density soybean genetic map based on AFLP markers. Crop Sci 37:537-543

Keim P, Shoemaker R C, Palmer R G (1989) Restriction fragment length polymorphism diversity in soybean. Theor Appl Genet. 77:786-792

Kim H S, Diers B W (2000) Inheritance of partial resistance to *Sclerotinia* stem rot in soybean. Crop Sci 40:55-61

Lark K G, Chase K, Adler F, Mansur L M, Orf J H (1995) Interactions between quantitative trait loci in soybean in which trait variation at one locus is conditional upon a specific allele at another. Proc Natl Acad Sci USA 92:4656-4660

Lark K G, Orf J, Mansur L M (1994) Epistatic expression of quantitative trait loci (QTL) in soybean (*Glycine max* (L.) Merr.) determined by QTL association with RFLP alleles. Theor Appl Genet. 88:486-489

Lark K G, Weisemann J M, Matthews B F, Palmer R, Chase K, Macalma T (1993) A genetic map of soybean (*Glycine max* L.) using an intraspecific cross of two cultivars: 'Minsoy' and 'Noir 1'. Theor Appl Genet. 86:901-906

Lee S H, Bailey M A, Mian M A R, Carter T E, Jr., Ashley D A, Hussey R S, Parrott W A, Boerma H R (1996a) Molecular markers associated with soybean plant height, lodging, and maturity across locations. Crop Sci 36:728-735

Lee S H, Bailey M A, Mian M A R, Carter T E, Jr., Shipe E R, Ashley D A, Parrott W A, Hussey R S, Boerma H R (1996b) RFLP loci associated with soybean seed protein and oil content across populations and locations. Theor Appl Genet. 93:649-657

Lee S H, Bailey M A, Mian M A R, Shipe E R, Ashley D A, Parrott W A, Hussey R S, Boerma H R (1996c) Identification of quantitative trait loci for plant height, lodging, and maturity in a soybean population segregating for growth habit. Theor Appl Genet. 92:516-523

Lewers K S, Crane E H, Bronson C R, Schupp J M, Keim P, Shoemaker R C (1999) Detection of linked QTL for soybean brown stem rot resistance in 'BSR 101' as expressed in a growth chamber environment. Mol Breed 5:33-42

Liu F, Zhuang B C, Zhang J S, Chen S Y (2000) Construction and analysis of soybean genetic map. Acta Genetica Sinica 27:1018-1026

Mahalingam R, Skorupska H T (1995) DNA markers for resistance to *Heterodera glycines* I. Race 3 soybean cultivar Peking. Breeding Sci 45:435-443

Mansur L M, Lark K G, Kross H, Oliveira A (1993) Interval mapping of quantitative trait loci for reproductive, morphological, and seed traits of soybean (*Glycine max* L.). Theor Appl Genet. 86:907-913

Mansur L M, Orf J H, Chase K, Jarvik T, Cregan P B, Lark K G (1996) Genetic mapping of agronomic traits using recombinant inbred lines of soybean. Crop Sci 36:1327-1336

Matthews B F, Devine T E, Weisemann J M, Beard H S, Lewers K S, MacDonald M H, Park Y B, Maiti R, Lin J J, Kuo J, Pedroni M J, Cregan P B, Saunders J A (2001) Incorporation of sequenced cDNA and genomic markers into the soybean genetic map. Crop Sci 41:516-521

Meksem K, Doubler T W, Chancharoenchai K, Njiti V N, Chang S J C, Arelli A P R, Cregan P E, Gray L E, Gibson P T, Lightfoot D A (1999) Clustering among loci underlying soybean resistance to *Fusarium solani*, SDS and SCN in near-isogenic lines. Theor Appl Genet. 99:1131-1142

Meksem K, Pantazopoulos P, Njiti V N, Hyten L D, Arelli P R, Lightfoot D A (2001) 'Forrest' resistance to the soybean cyst nematode is bigenic: saturation mapping of the Rhg1 and Rhg4 loci. Theor Appl Genet. 103:710-717

Mian M A R, Ashley D A, Vencill W K, Boerma H R (1998) QTLs conditioning early growth in a soybean population segregating for growth habit. Theor Appl Genet. 97:1210-1216

Narvel J M, Walker D R, Rector B G, All J N, Parrott W A, Boerma H R (2001) A retrospective DNA marker assessment of the development of insect resistant soybean. Crop Sci 41:1931-1939

Neto AL d-F, Hashmi R, Schmidt M, Carlson S R, Hartman G L, Li S, Nelson R L, Diers B W (2007) Mapping and confirmation of a new sudden death syndrome resistance QTL on linkage group D2 from the soybean genotypes PI 567374 and 'Ripley'. Mol Breed 20:53-62

Njiti V N, Meksem K, Iqbal M J, Johnson J E, Kassem M A, Zobrist K F, Kilo V Y, Lightfoot DA (2002) Common loci underlie field resistance to soybean sudden death syndrome in Forrest, Pyramid, Essex, and Douglas. Theor Appl Genet. 104:294-300

Orf J H, Chase K, Adler F R, Mansur L M, Lark K G (1999a) Genetics of soybean agronomic traits: II. Interactions between yield quantitative trait loci in soybean. Crop Sci 39:1652-1657

Orf J H, Chase K, Jarvik T, Mansur L M, Cregan P B, Adler F R, Lark K G (1999b) Genetics of soybean agronomic traits: I. Comparison of three related recombinant inbred populations. Crop Sci 39:1642-1651

Panthee D R, Pantalone V R, West D R, Saxton A M, Sams C E (2005) Quantitative trait loci for seed protein and oil concentration, and seed size in soybean. Crop Sci 45:2015-2022

Prabhu R R, Njiti V N, Bell-Johnson B, Johnson J E, Schmidt M E, Klein J H, Lightfoot D A (1999) Selecting soybean cultivars for dual resistance to soybean cyst nematode and sudden death syndrome using two DNA markers. Crop Sci 39:982-987

Qiu B X, Arelli P R, Sleper D A (1999) RFLP markers associated with soybean cyst nematode resistance and seed composition in a 'Peking' X 'Essex' population. Theor Appl Genet. 98:356-364

Rafalski A, Tingey S (1993) RFLP map of soybean (*Glycine max*). In: O'Brien S J (ed) Genetic maps: Locus maps of complex genomes. Cold Spring Harbor Press Lab. Press, New York, pp 6149-6156

Rector B G, All J N, Parrott W A, Boerma H R (1999) Quantitative trait loci for antixenosis resistance to corn earworm in soybean. Crop Sci 39:531-538

Rector B G, All J N, Parrott W A, Boerma H R (2000) Quantitative trait loci for antibiosis resistance to corn earworm in soybean. Crop Sci 40:233-238

Schuster I, Abdelnoor R V, Marin S R R, Carvalho V P, Kiihl R A S, Silva J F V, Sediyama C S, Barros E G, Moreira M A (2001) Identification of a new major QTL associated with resistance to soybean cyst nematode (*Heterodera glycines*). Theor Appl Genet. 102:91-96

Shen R, Fan J-B, Campbell D, Chang W, Chen J, Doucet D, Yeakley J, Bibikova M, Garcia E-W, McBride C, Steemers F, Garcia F, Kermani B-G, Gunderson K, Oliphant A (2005) High-throughput SNP genotyping on universal bead arrays. Mutat Res 573:70-82

Shoemaker R C, Olson T C (1993) Molecular linkage map of soybean (*Glycine max* L. Merr.). In: O'Brien S J (ed) Genetic maps: Locus maps of complex genome. Cold Spring Harbor Laboratory Press, Cold Spring Harbor, N.Y., pp 6.131-6.138

Song Q J, Marek L F, Shoemaker R C, Lark K G, Concibido V C, Delannay X, Specht J E, Cregan P B (2004) A new integrated genetic linkage map of the soybean. Theor Appl Genet. 109:122-128

Specht J E, Chase K, Macrander M, Graef G L, Chung J, Markwell J P, Germann M, Orf J H, Lark K G (2001) Soybean response to water: a QTL analysis of drought tolerance. Crop Sci 41:493-509

Terry L I, Chase K, Jarvik T, Orf J, Mansur L, Lark K G (2000) Soybean quantitative trait loci for resistance to insects. Crop Sci 40:375-382

Thomson Scientific Inc (2008) Biological Abstracts®. http://thomsonscientific.com/support/faq/wok3new/Biological-Abstracts/. Cited 14 Jul. 2008

Vaghchhipawala Z, Bassuner R, Clayton K, Lewers K, Shoemaker R, Mackenzie S (2001) Modulations in gene expression and mapping of genes associated with cyst nematode infection of soybean. Mol Plant Microbe Interactions 14:42-54

Vierling R A, Faghihi J, Ferris V R, Ferris J M (1996) Association of RFLP markers with loci conferring broad-based resistance to the soybean cyst nematode (*Heterodera glycines*). Theor Appl Genet. 92:83-86

Vollmann J, Schausberger H, Bistrich H, Lelley T (2002) The presence or absence of the soybean Kunitz trypsin inhibitor as a quantitative trait locus for seed protein content. Plant Breeding 121:272-274

Wang D, Arelli P R, Shoemaker R C, Diers B W (2001) Loci underlying resistance to Race 3 of soybean cyst nematode in *Glycine soja* plant introduction 468916. Theor Appl Genet. 103:561-566

Wang D, Graef G L, Procopiuk A M, Diers B W (2004a) Identification of putative QTL that underlie yield in interspecific soybean backcross populations. Theor Appl Genet. 108:458-467

Wang H L, Yu D Y, Wang Y J, Chen S Y, Gai J Y (2004b) Mapping QTLs of soybean root weight with RIL population NJRIKY. Hereditas Beijing 26:333-336

Wang H L, Yu D Y, Wang Y J, Chen S Y, Gai J Y (2004c) Mapping QTLs of soybean root weight with RIL population NJRIKY. Yichuan 26:333-336

Wang Y J, Dong Fang Y, Wang X Q, Yang Y L, Yu D Y, Gai J Y, Wu X L, He C Y, Zhang J S, Chen S Y (2004d) Mapping of five genes resistant to SMV strains in soybean. Acta Genetica Sinica 31:87-90

Webb D M, Baltazar B M, Rao-Arelli A P, Schupp J, Clayton K, Keim P, Beavis W D (1995) Genetic mapping of soybean cyst nematode race-3 resistance loci in the soybean PI 437.654. Theor Appl Genet. 91:574-581

Wu X L, He C Y, Wang Y J, Zhang Z Y, Dong Fang Y, Zhang J S, Chen S Y, Gai J Y (2001) Construction and analysis of a genetic linkage map of soybean. Acta Genetica Sinica 28:1051-1061

Yamanaka N, Ninomiya S, Hoshi M, Tsubokura Y, Yano M, Nagamura Y, Sasaki T, Harada K (2001) An informative linkage map of soybean reveals QTLs for flowering time, leaflet morphology and regions of segregation distortion. DNA Research 8:61-67

Yuan J, Njiti V N, Meksem K, Iqbal M J, Triwitayakorn K, Kassem M A, Davis G T, Schmidt M E, Lightfoot D A (2002) Quantitative trait loci in two soybean recombinant inbred line populations segregating for yield and disease resistance. Crop Sci 42:271-277

Yue P, Arelli P R, Sleper D A (2001a) Molecular characterization of resistance to *Heterodera glycines* in soybean PI 438-489B. Theor Appl Genet. 102:921-928

Yue P, Sleper D A, Arelli P R (2001b) Mapping resistance to multiple races of *Heterodera glycines* in soybean PI 89772. Crop Sci 41:1589-1595

Zhu S, Walker D R, Boerma H R, All J N, Parrott W A (2006) Fine mapping of a major insect resistance QTL in soybean and its interaction with minor resistance QTLs. Crop Sci 46:1094-1099

EXPERIMENTAL

The following examples are provided in order to demonstrate and further Illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); ° C. (degrees Centigrade/Celsius).

EXAMPLE 1

Materials and Methods

Soybean plant introductions (PI) from MG 0 to III were obtained from the USDA Soybean Germplasm Collection in Urbana, Ill. (Table 1). A total of 2,147 PIs were evaluated in 2002 and 2003, including 5 MG 0 accessions (PI 468920 to PI 597467), 530 MG I accessions (FC 03609 to PI 612761E), 979 MG II accessions (PI 253650A to PI 612758E), and 633 MG III accessions (FC 02108 to PI 612759D). Accessions originally from northern China were selected, as the climatic conditions are similar to those in the northern USA, where the soybean aphid over-winters, and because soybeans in that region have been exposed to aphids over the years. 'Williams 82' was included as a susceptible check in these experiments and one or more of the three resistant genotypes, 'Dowling', 'Jackson', and PI 71506 (Hill et al., (2004) Crop Sci. 44: 98-106), were included as resistant checks. Both the susceptible and resistant checks were obtained from Dr. Glen Hartman, USDA-ARS at Urbana, Ill., United States.

TABLE 1

Total number of plant introductions (FC and PI numbers) evaluated in each maturity group (MG) in 2002 and 2003.

| MG | Range from which evaluated Accessions where selected | Total Number |
|---|---|---|
| 0 | PI 468920 to PI 597467 | 5 |
| I | FC 03609 to PI 612761E | 530 |
| II | PI 253650A to PI 612758E | 979 |
| III | FC 02108 to PI 612759D | 633 |
| Total | | 2147 |

PIs and checks were first evaluated in choice tests (Davis, (1985) Insect Sci Appl 6:391-400), in which the aphids colonized genotypes they preferred, to identify PIs with either antixenosis or antibiosis. The resistant PIs were then re-evaluated in no-choice tests (Davis, (1985) Insect Sci Appl 6:391-400), in which aphids were confined on plants of one genotype, to identify PIs with antibiosis resistance. The insects have no choice but to feed on the genotype on which they are confined. The no-choice test is also conducted to overcome the uneven distribution of insects, which normally occurs in choice tests, resulting in escapes (Saxena and Khan, (1984) Crop Sci. 24:1204-1206).

Experiments were carried out on the campus of Michigan State University (MSU), East Lansing, Mich. Soybean aphids were obtained from nearby naturally infested soybean fields for summer fieldwork, and from a colony maintained in growth chambers at the Field Crops Entomology Laboratory at MSU for winter greenhouse work. The experiments were set up as a randomized complete block design with two replications.

During vegetative growth of soybean, aphid colonies were usually found at the growing points e.g., partially expanded young trifoliate, petioles, and stems. At the reproductive stage the aphids became more widely dispersed on the plant and could be found on the underside of mature leaves, on lower stems, lateral branches, petioles, and pods (Ragsdale et al., (2004) Ann. Entomol. Soc. Am. 97:204-208). Based on experiments conducted during the course of the present invention, most aphid colonies stayed on inoculated trifoliates for more than 10 days after inoculation, with the inoculated leaves still not overcrowded. Therefore, an estimate of the increase of the aphid population in the first 10 days can be obtained by counting aphids on the inoculated trifoliate 10 days after inoculation.

Five seeds per accession were planted in the field in a 0.30 m long plot (Greenhouse: 3 seeds, gallon-sized plastic pots). Inoculation of plants was 2 weeks after planting (early vegetative stage), two plants per accession inoculated with 2 aphids on the new trifoliate. Counting of aphid population was done 10 days after inoculation using a hand counter. Four weeks after inoculation the plants were rated visually using the rating method of Zhuang (Zhuang, (1999) Biological studies of Chinese wild soybean. 1st ed., Science Publisher, Beijing, China). Weekly visual ratings using the method of Zhuang (1999), supra, showed that there was a clear difference in susceptibility or resistance among accessions four weeks after inoculation when aphid densities reached their peak. Thus DI values four weeks after inoculation were used to determine susceptibility of the PIs. Visual rating data two weeks after inoculation were not used because of low aphid populations. Two weeks after inoculation, the method of Zhuang (supra) categorizes the plants as either a '1' or '2' and the results are similar to counting aphids 10 days after inoculation. On the other hand, five weeks after inoculation, the aphid populations started to decline due to overcrowding and development of winged aphids, which left the plants. Therefore, visual rating data five weeks after inoculation were not used in the analysis.

Lin et al. (Lin et al., (1992) Soybean Science, 11(4):318-321) showed that the soybean aphid colonizes soybeans in China at the early vegetative stage. Aphid populations increase gradually and reach a 10 to 15 day exponential growth phase coinciding with late vegetative to early reproductive stage of the plants. Ten days after inoculation, at the early vegetative stage, a high percentage of test plants had very few aphids per leaflet. Correlations were low between the numbers of aphids per leaflet 10 days after inoculation and the DI four weeks after inoculation in the first and the second years of evaluation (r=0.16 and r=0.20, respectively). These low correlation values indicate that counting aphids on the inoculated trifoliate 10 days after infestation in the early vegetative stage is not an optimal method for determining the resistance or susceptibility of an accession. Counting the total number of aphids on the whole plant 10 days after inoculation would also not have helped to separate resistant from susceptible accessions because most aphid colonies did not move away from the inoculated trifoliate during the first 10 days after inoculation. It is advisable to count aphids on the whole plants in the late vegetative or early reproductive stage in order to identify truly resistant accessions. However, counting aphids is very tedious and time consuming. For further large-scale evaluation of aphid resistance such as progeny evaluation in a breeding program, the preferred method is described in Zhuang (Zhuang, 1999, Biological studies of Chinese wild soybean. 1st ed., Science Publisher, Beijing, China).

Summer Field Evaluation

Choice Test

Two experiments were carried out in the summers of 2002 and 2003 to evaluate soybean germplasm for aphid resistance.

Summer plantings were done at the Agronomy Farm, Michigan State University (MSU), in 12.2.times.18.3 m (40×60 feet seed cage) polypropylene cages with a 0.49 mm mesh size (Redwood Empire Awning Co., Santa Rosa, Calif.) that are aphid- and predator-proof. Results showed Low correlations (r=0.16, n=1017, p<0.0001) in 2002 and (r=0.20, n=1108, p<0.0001) in 2003 between the average number of aphids per leaflet and the DI of an accession. Specifically, 6 PI s—Aphid 1, Aphid 2, Aphid 3, Aphid 4, Aphid 5, and Aphid 6 Aphid 5 and Aphid 6 showed some resistance to the soybean aphid (SBA).

In 2002, 1,043 PIs, the susceptible check (Williams 82), and a resistant check (Jackson) were evaluated in the field cage. The PIs and checks were planted on 26 June and each check was treated as an accession in the test. Five seeds per accession were planted in a plot 0.3 m long and with a row spacing of 0.3 meter. Each accession was planted in a single plot without replication. At the V1 stage (Fehr and Caviness, 1977, Iowa State University, No. 80), two plants per accession were inoculated with two wingless aphids each on the partially expanded trifoliate, using a camel-hair brush. Aphids were obtained from naturally infested fields on the Agronomy Farm, MSU. The aphids were left to multiply and move among plants.

In 2003, a new set of 1,103 PIs, the resistant checks (Dowling, Jackson, and PI 71506), and the susceptible check (Williams 82), were evaluated in two field cages. In each cage, a complete set of the PIs plus the checks were planted as a randomized complete block. Each check was treated as an accession in the test. The lines were sown on 30 May in one cage (planting 1) and on 6 June in the second cage (planting 2). The methods of inoculation plot sizes, and evaluation procedures were the same as for the 2002 field evaluation.

Winter Greenhouse Evaluation

Choice and No-Choice Tests

A winter evaluation was carried out in a large greenhouse with temperatures between 22 and 25° C. to verify the results obtained in the field in 2002. The PIs planted in the field in 2002 were evaluated. Seeds were planted on 21 Nov. 2002 in the greenhouses at the Horticulture Research Farm at MSU. Three seeds of each genotype were planted in a plastic pot 22 cm in diameter and 23 cm deep. Each genotype was planted in a single pot without replication and the pots of genotypes were randomly laid out on the benches in the greenhouse. The soil used in greenhouse tests was Baccto High Porosity Professional Planting mix (Michigan Peat Company. Houston, Tex.). Two of the three plants were inoculated at the V1 stage (Fehr and Caviness, 1977, Iowa State University, No. 80) with two wingless aphids each on the partially expanded trifoliate.

A no-choice test was carried out in the greenhouse from December 2003 to February 2004, to determine the type of resistance of each resistant source. Each pot was set up as described for the 2002 greenhouse plantings with two replications and in a randomized complete block design. Each pot was isolated by the use of a no-see-um mesh cage (Venture Textiles, Inc. Braintree, Mass.). The entries in the no-choice test were the resistant PIs identified in the 2002 and 2003 evaluation in choice tests, the resistant check (Jackson), the susceptible check (Williams 82), and two soybean varieties (cultivars), Titan and Loda.

Confirmation of Resistance

In the summer of 2004, PIs previously identified as potentially aphid resistant after two years of evaluation, and Williams 82, were evaluated in the field to confirm the resistance found in previous tests. The experiment was set up as a randomized complete block design with three replications. Ten seeds were planted in each 0.6 m plot. Ten plants were inoculated at the V1 stage (Fehr and Caviness, 1977, Iowa State University, No. 80) with wingless aphids as described earlier.

Data Collection

In these studies, except the confirmation of resistance test, aphid populations on inoculated trifoliate were counted 10 days after inoculation when the plants were at the V3 stage (Fehr and Caviness, 1977, Iowa State University, No. 80). Four weeks after inoculation, the plants in each accession were visually rated for susceptibility to soybean aphid using the rating scale shown in FIG. 1 (Zhuang, 1999, Biological studies of Chinese wild soybean. 1st ed., Science Publisher, Beijing, China). A damage index (DI) for each accession was calculated using the following formula (Zhuang, 1999, Biological studies of Chinese wild soybean. 1st ed., Science Publisher, Beijing, China): DI=.SIGMA. (Scale value-.times.No. of plants in the category)/(4.times. Total no. of plants evaluated).times. 100. The DI ranges between 0% for no infestation and 100% for the most severe damage. In early studies a DI was the susceptibility of the plant to aphid infestation expressed as a percentage, with 25% or less as resistant and greater than 25% to 100% as susceptible. However in later studies a DI of 30% or less was classified as resistant, whereas a DI of 30% or more was classified as susceptible. The 30% break point was chosen based on the observation that a soybean genotype with a DI value less than 30% never showed symptoms of damage under high aphid pressure until the end of the season. In the second year of field evaluation, the plants were visually rated weekly from the second week through the fifth week after inoculation to determine and confirm the best time to carry out the visual rating.

Statistical Analysis

The data for each year were analyzed using the PROC GLM procedure in the SAS statistical package V8 (SAS Institute, 1999, Software release 8, SAS Institute, Inc. Cary, N.C.). Means were separated by least significant difference (LSD) at the 5% probability level. Linear correlations between the average number of aphids per leaflet ten days after inoculation and the DI were calculated with PROC CORR.

Genetic Studies of Aphid Resistance for Linkage Group Analysis

Linkage group analysis was used for identifying the linkage groups comprising aphid resistance germplasm. F2 populations from crosses between aphid resistant soybean and aphid susceptible soybean were evaluated for aphid resistance then tested with simple sequence repeat (SSR) DNA markers for identifying J, K, B2, D1a and D1b Linkage Groups comprising aphid resistant germplasm.

Evaluation of soybean plants for resistance to soybean aphids was carried out as described in Mensah, et al. 2005 (Crop Sci. 45:2228-2233) as described herein. Aphid damage data were collected weekly two weeks after inoculation until the fourth week. Data collected at weeks 3 and 4 were used to identify DNA markers associated with aphid resistance. Data collected at week 4 were used to test the segregation ratios.

Chi-square tests were performed to test the goodness-of-fit of observed segregations among the seven F2 populations with different genetic ratios.

A SOYBASE website hosted by Iowa State University was used for providing PCR sequences, forward and reverse, for amplifying Satt SSR markers and for providing linkage group identification using Satt SSR marker information, (Tables 5-11 and FIGS. 9-16).

Evaluation of the soybean plants with SSR markers: PCR amplification of SSR markers was carried out as described in Comelious, et al. ((2005) (Mol. Breed. 16:103-112)). The PCR products were analyzed in a 6% non-denaturing polyacrylamide gel system as described by Wang, et al. ((2003) (Crop Sci. 43:1828-1832)).

Sequences for Satt PCR Primers Used to Amplify SSR Loci in Soybean are described in Zhu et al. Single-nucleotide polymorphisms in soybean, Genetics 2003 March; 163(3): 1123-34. Sequences for Satt PCR Primers Used to Amplify SSR markers for identifying associations with aphid resistant germplasm are as follows:

```
Satt271
(SEQ ID NO: 01 Forward primer: GTT GCA GTT GTG CGT GGG AGA GAG
and

SEQ ID NO: 02 Reverse primer: GCG ACA TAG CTA ATT AAG TAA GTT),

Satt280
(SEQ ID NO: 03 Forward primer GCG GAA TCT GCT TAT TCA TTG TGT G
and

SEQ ID NO: 04 Reverse primer GCG CCA TGC TGT AAC ACG TCA AT),

Satt304
(SEQ ID NO: 05 Forward primer GGG TAG TGA CGT ATT TCA TGG TC
and

SEQ ID NO: 06 Reverse primer GCG TAA AAA CAT TCG TTG ACT ACA TAA),

Satt439
(SEQ ID NO: 07 Forward primer GCG AAA ATG ATT AAA TTG TTT TCT CAA G
and

SEQ ID NO: 08 Reverse primer GCG GCA CGT TGC CAT ATA AGA TAA AGG),

Satt468
(SEQ ID NO: 09 Forward primer GCG TCT CTT ATT TTG ACC TTT TTA ACT T
and

SEQ ID NO: 10 Reverse primer GCG TTT TGT ATT TGG TCT ATC TGC TTA G),

Satt529
(SEQ ID NO: 11 Forward primer GCG CAT TAA GGC ATA AAA AAG GAT A
and

SEQ ID NO: 12 Reverse primer GCA CAA TGA CAA TCA CAT ACA),

Satt628
(SEQ ID NO: 13 Forward primer CTA CCT TTA AGG TCG TTT TCA AGT
and

SEQ ID NO: 14 Reverse primer GCA TGC TCC TTT TAT GCT CCT TTT),
and

Satt686
(SEQ ID NO: 15 Forward primer ACG GAA AAT AAA TGA AAC TAA GA
and

SEQ ID NO: 16 Reverse primer: GCG CTA TCA GAT AGA GAA GCA GAA GAA T).
```

A method of PCR amplification using Satt primers PCR Reagents for Soybean SSR Amplification is provided as follows: a PCR reaction mixture is provided comprising 30 ng genomic soybean DNA, buffer (50 mM KCl, 10 mM Tris-HCl (pH 9.0 at 25° C.), and 0.1% Triton X-100) 1.5 mM $MgCl_2$, 0.15 mM for each of the NTPs, and 1 unit Taq DNA Polymerase. Thermocycling Profile for Amplification of Soybean SSRs is 1 cycle of 2 min at 95° C., 33 cycles of: Denaturation: 92° C. then annealing (optimum temperature or 47° C.) then extension at 68° C.

Associations of SSR markers with resistance to soybean aphids were determined with the single marker analysis method in WinQTLcart Version 2.5 (Wang, et al. (2005) Windows QTL Cartographer 2.5. Department of Statistics, North Carolina State University, Raleigh, N.C.).

EXAMPLE 2

Illustration of the Visual Rating Scale Used to Establish the Damage Index (DI)

The following index was used for establishing a Damage Index rating. 0=No aphids, plant appears normal and healthy; 1=Less than 100 aphids per plant, plant appears normal and healthy; 2=101-300 aphids per plant, mostly on the young leaves and the tender stem at top of plant, plant appears normal and healthy; 3=301-800 aphids per plant, leaves slightly curly and shiny, young leaves and stems covered with aphids; 4=More than 800 aphids per plant, plants stunted, leaves severely curled, yellow, covered with sooty mold and cast skins. (FIG. 1).

EXAMPLE 3

Choice Tests in 2002

In the first year of evaluation in the field cage, the average number of aphids per leaflet ranged from 0 to 500. In the greenhouse, the average number of aphids per leaflet ranged from 0 to 170. Results from the visual rating and calculation of the DI showed that 1008 and 973 of the accessions evaluated in the field and greenhouse, respectively, were susceptible to the soybean aphid (DI>30%). Twenty-eight and 62 accessions did not germinate in the field and the greenhouse, respectively. The correlation between the average number of aphids per leaflet 10 days after inoculation and the DI of an accession was low (r=0.16, n=1043, p<0.0001). Seven of the 1043 accessions appeared to be resistant (DI<30%) to the aphid in the field cage, while eight accessions showed resistance in the greenhouse (Table 2).

Three of these accessions were resistant in both the field and greenhouse evaluations. The accessions that showed resistance in one test, field or greenhouse, were replanted in the greenhouse in the spring of 2003 and found to be susceptible. The resistant check, Jackson, had a DI of 55% in the field and 25% in the greenhouse. After the first year of evaluation, accessions PI 567543C, PI 567597C, PI 567541B and PI 567598B appeared to be resistant to the soybean aphid.

TABLE 2

Number of accessions in Each DI category
For 2002 (n = 1043) and 2003 (n = 1108)

| Year and Location/replication | Damage Index | | | |
|---|---|---|---|---|
| | ≦30% | 31 to 50% | 51 to 75% | >75% |
| Field (2002) | 7 | 10 | 56 | 942 |
| Greenhouse (2002) | 8 | 27 | 200 | 746 |
| Field Rep. 1 (2003) | 12 | 14 | 164 | 753 |
| Field Rep. 2 (2003) | 10 | 12 | 127 | 856 |

EXAMPLE 4

Choice Tests in 2003

In the second year of evaluation, the number of aphids per leaflet ranged from 0 to 326 for the first planting and 0 to 244 for the second planting. Based on DI, 931 and 995 of the plants were found to be susceptible (DI>30%) in plantings 1 and 2 respectively. As in the previous year, the DI value four weeks after inoculation did not reflect the aphid population 10 days after inoculation. The correlation between the average number of aphids per leaflet 10 days after inoculation and the DI value 4 weeks after inoculation was low (r=0.20, n=1103, p<0.0001) in 2003. (Table 3).

Eight accessions were rated as resistant in planting 1 and ten accessions were rated as resistant in planting 2. The difference in numbers of accessions rated as resistant was due to some accessions failing to germinate in both plantings. However there were two accessions, PI 603392 and PI 603418C, which had a DI of <30% in both plantings. Resistant checks had a DI of 25% in both plantings. In cases where germination did not occur in both plantings, the accessions were replanted in the greenhouse in the winter of 2003 and found to be susceptible.

TABLE 3

Results of the no-choice test for the six resistant accessions, Resistant and susceptible checks, and varieties in 2003.

| Entry | Maturity group | Average No. of aphids per leaflet[1] | Damage index (%)[2] |
|---|---|---|---|
| PI 567543C: Aphid-R1 | III | 8 ab | 56 b[3] |
| PI 567597C: Aphid-R2 | III | 1 a | 62 b |
| PI 567541B: Aphid-R3 | III | 1 a | 25 a |
| PI 567598B: Aphid-R4 | III | 11 bc | 25 a |
| PI 603392: Aphid-R5 | III | 5 a | 81 c |
| PI 603418C: Aphid-R6 | III | 12 c | 77 c |
| Jackson | VII | 2 a | 25 a |
| Titan | I | 17 c | 71 c |
| Loda | II | 19 c | 83 c |
| Williams 82 | III | 19 c | 100 d |
| Mean | | 9.4 | 60.5 | note
[1]The data are the averages of 12 leaflets from two replications with two plants per replication and three leaflets per plant taken 10 days after inoculation.
[2]Averages of two replications.
[3]Means followed by the same letters are not significantly different by the least significant difference test (p = 0.05).

A brief summary of 2003 No-Choice results reveals that soybean plants Aphid-R3 and Aphid-R4 showed antibiosis while Aphid-R1, Aphid-R2, Aphid-R5 and Aphid-R6 demonstrated antixenotic properties.

EXAMPLE 5

No-Choice Test

The six MG III accessions classified as resistant in evaluation trials, PI 567543C, PI 567597C, PI 567541B, PI 567598B, PI 603392 and PI 603418C, were identified in field and greenhouse choice tests. The no-choice test showed that PI 567541B and PI 567598B had adverse effects on the aphid and thus possessed antibiosis as defined by Painter (Painter, 1951, Insect Resistance in Crop Plants, Macmillan). The high DIs obtained in no-choice test for PI 567543C and PI 567597C (which were classified resistant in choice tests) is likely due to the change in feeding response of the aphid in choice and no-choice tests as found by Smith et al. (Smith, et al., 1994, Techniques for evaluating insect resistance in crop plants, CRC Press, Inc.). Also, it is possible for a genotype classified as resistant in a choice test to be declared susceptible in a no-choice test (Tingey, 1986, Techniques for evaluating plant resistance to insects, in insect-plant interactions, Springer-Verlag, New York). Soybean plants PI 567543C and PI 567597C, while having lower DI values than Williams 82, are not resistant (Table 1). The high (r=0.63, p=0.048) correlation between the average number of aphids per leaflet 10 days after inoculation and the DI of an entry in the no-choice test is attributed to the fact that the entries chosen for this test were truly susceptible or resistant as found in previous evaluations. The inconsistent average numbers of aphids per leaflet for PI 567598B and PI 603392 (Table 1) strengthens the fact that counting of aphids 10 days after inoculation is not optimal for selecting aphid resistant plants. The method of Zhuang (Zhuang, 1999, Biological studies of Chinese wild soybean. 1st ed., Science Publisher, Beijing, China) would still be the best to use in experiments with few entries.

The test conducted to confirm the resistance after two years of evaluation revealed that PI 603392 and PI 603418C, both from Liaoning province, were not resistant to the soybean aphid. These plants, when evaluated in 2003 in the field cages, did not show symptoms of severe aphid infestation. According to Painter (Painter, 1951, Insect Resistance in Crop Plants, Macmillan), the type of resistance that enables a host plant to withstand infestation by insects without suffering severe damage is tolerance. PI 603392 and PI 603418C plants might be tolerant, but tolerance can be confirmed with further yield and dry matter studies. These two accessions were not considered resistant after their poor performance in the confirmation test. Smith (Smith, 1989, Plant resistance to insects: A fundamental approach, Wiley, New York) also observed that pseudo-resistance or false resistance may occur in normally susceptible plants. Resistance may have been induced temporarily by variations in temperature, day length, soil chemistry, plant or soil water content, or internal plant metabolism. Susceptible plants may simply escape damage because of incomplete infestation.

EXAMPLE 6

Confirmation of Resistance

Resistance in the four accessions (PI 567543C, PI 567597C, PI 567541B, and PI 567598B) identified in the choice tests in 2002 was confirmed in 2004 (Table 2). At three and four weeks after inoculation, highly significant differences ($p<0.0001$) were found between the DIs for these four accessions and the DIs for PI 603392 and PI 603418C, identified in choice tests in 2003. The amount of damage to the plant as a result of aphid feeding was greater on the susceptible check than on PI 603392 or PI 603418C four weeks after inoculation. The susceptible check appeared stunted, and its leaves were curled and covered with black sooty mold, while PI 603392 and PI 603418C showed none of these symptoms. (Table 4).

TABLE 4

Damage Index (DI) based on three replications in 2004 for six putative resistant accessions, identified after two years of screening, and a susceptible check three and four weeks after inoculation.

| Entry | Damage Index (%) | |
|---|---|---|
| | Three weeks after Inoculation | Four weeks after Inoculation |
| PI 567543C: Aphid-R1 | 25 a[1] | 25 a |
| PI 567597C: Aphid-R2 | 26 a | 26 a |
| PI 567541B: Aphid-R3 | 25 a | 25 a |
| PI 567598B: Aphid-R4 | 26 a | 26 a |
| PI 603392: Aphid-R5 | 75 b | 79 b |
| PI 603418C: Aphid-R6 | 75 b | 79 b |
| Williams 82 | 83 c | 100 c |
| Mean | 46.86 | 51.43 |

[1]Mean of three replications of a maximum of 10 plants each. Means followed by the same letters are not significantly different by the least significant difference test (P = 0.05).

A brief summary of 2004 results supports the resistance of Aphid-R1, Aphid-R2, Aphid-R3 and Aphid-R4 to SBAs while Aphid-R5 and Aphid-R6 showed low level resistance as tolerance.

Therefore the inventors discovered four resistant PI s in MG III found (2 have antibiotic and 2 have antixenotic properties). Further refinements of the methods were made for subsequent studies such that before inoculation aphids maintained in growth chamber were acclimated to field or greenhouse conditions, counting of aphid populations were made at the late vegetative to early reproductive stage due to low correlation between the average number of aphids per leaflet and the DI of an accession at the early vegetative stage, and the rating method of Zhuang (1999), supra, used at 3, 4, 5 weeks after inoculation were continued.

EXAMPLE 7

Transfer Aphid Resistance from the Aphid Resistant Germplasm to Elite Soybean Germplasm Inventors' preliminary data showed that aphid resistance in their elite soybean cultivars is a dominant trait. A backcross method as shown in FIG. 3 will be an efficient method to transfer the resistant gene(s) from the aphid resistant PIs (plant introductions) to elite soybean germplasm. The aphid resistant accession PIs are: PI 567543C, PI 567597C, PI 567541B, and PI 567598B. The elite variety can be any soybean varieties. To shorten the total time needed for the transfer process, greenhouses or winter nurseries can be used to carry out the activities of any season in FIG. 3. Progress for up to three seasons per year can be made. To minimize the transfer of undesirable genes from the PIs to the elite germplasm, DNA markers can be used to select progenies with minimum proportion of the genome from the PIs. Forty to eighty simple sequence repeat (SSR) DNA markers evenly spaced on the soybean linkage map can be used to assist the selection. Computer simulation showed that 93% of the genome of the recurrent parent can be recovered in two cycles of backcrosses if DNA markers are used to assist the selection (Frisch et al., (1999) Crop Science 39:1295-1301.

Evaluation of progenies for aphid resistance can be carried out as described by Mensah, et al. 2005 (Crop Sci. 45:2228-2233). Evaluation of progenies for their genome compositions using SSR DNA markers can be carried out as described by Wang et al., (2003) Crop Sci. 43: 1828-1832, herein incorporated by reference.

Variations of the method described above:

The method outlined in FIG. 3 can be modified. The following are examples of modifications:

Modification 1:

In season 3, self-pollinate the selected $BC_1F_1$ (BC=backcross) to obtain $BC_1F_2$. In season 4, select $BC_1F_2$ individuals that are aphid resistant and have the highest percentage of elite genome based on DNA fingerprinting data. In season 5 and after, evaluate progenies of selected individuals for aphid resistance and agronomic performance and release the lines that are homozygous for aphid resistance and acceptable in agronomic performance as new varieties or germplasm.

Modification 2:

In season 2, self-pollinate the $F_1$ to obtain $F_2$. In season 3, select $F_2$ individuals that are aphid resistant and have the highest percentage of elite genome based on DNA fingerprinting data. In season 4 and after, evaluate progenies of selected individuals for aphid resistance and agronomic performance and release the lines that are homozygous for aphid resistance and acceptable in agronomic performance as new varieties or germplasm.

Modification 3:

Use the method outlined in FIG. 3 with the modifications 1 and 2 described above without fingerprinting with SSR DNA markers and/or without selection based on DNA fingerprinting data, an example of soybean SSR mapping is provided in U.S. Patent Appln. No. 20020133852, herein incorporated by reference. Marker-assisted selection is generally described in the following U.S. Pat. Nos. 5,536,901, 5,612,191, 5,606,823, 5,574,210, 5,492,547, 5,491,081, 5,476,524, and 5,385,835, the entire contents of each of which are herein incorporated by reference.

EXAMPLE 8

Genetics of Aphid Resistance

Crosses of an aphid susceptible parent with an aphid resistant parent (PI 567541B or PI 567598B) were done for determining whether aphid resistance segregated as a Medelian dominant or recessive trait. Following crosses, the No. of resistant $F_1$ vs. No. of susceptible $F_1$ progeny plants were identified and counted.

The results in Table 5 show that antibiosis resistance in PI 567541B and PI 567598B is recessive.

TABLE 5

F1 plants from the crosses between aphid resistant parents (PI 567541B and PI 567598B) and an aphid a susceptible parent (E00075) were shown to be susceptible to soybean aphids, which is the expected result for a recessive trait.

| Cross ID | Parents | No. of $F_1$ plant | No. of resistant $F_1$ plant | No. of susceptible $F_1$ plant |
|---|---|---|---|---|
| 040129 | E00075 × PI 567541B | 6 | 0 | 6 |
| 040130 | E00075 × PI 567598B | 12 | 0 | 12 |

Further segregation breeding studies, as described below, were done in order to identify the number of recessive genes contributing to aphid resistance. These results show that aphid resistance in both PI 567541B and PI 567598B appeared to be controlled by two recessive genes (see, Table 6).

TABLE 6

Segregation of aphid resistance in $F_2$ populations derived from susceptible × resistant crosses. The segregation data were tested for goodness of fit to a 15:1 (Susceptible:Resistant) ratio, which is the expected ratio for a trait controlled by two recessive genes. The observed ratios for the six populations did not deviate from the expected ratio.

| Population ID | Susceptible parent | Resistant parent | Total | Observed* R | Observed* S | Expected* R | Expected* S | P value of $X^2$ test |
|---|---|---|---|---|---|---|---|---|
| 040129-1 | E00075 | PI 567541B | 155 | 5 | 150 | 9.7 | 145.3 | 0.120 |
| 040129-2 | E00075 | PI 567541B | 98 | 5 | 93 | 6.1 | 91.9 | 0.639 |
| 040130-1 | E00075 | PI 567598B | 100 | 7 | 93 | 6.3 | 93.8 | 0.757 |
| 040130-2 | E00075 | PI 567598B | 126 | 8 | 118 | 7.9 | 118.1 | 0.963 |
| 030104-3 | Titan | PI 567598B | 415 | 26 | 389 | 25.9 | 389.1 | 0.990 |
| 030104-10 | Titan | PI 567598B | 416 | 26 | 390 | 26.0 | 390.0 | 1.000 |

*R = resistant, S = Susceptible

The following breeding study and analysis described below for determining a resistant: susceptible ratio in F2:3 lines was done in order to determine whether the two recessive genes are the same or different genes. The results show that resistant loci in PI 567541B and PI 567598B appeared to be two different sets of resistance genes (see, Table 7).

TABLE 7

The progenies from the cross between the two aphid resistant soybean genotypes (PI 567541B and PI 567598B) were segregating for aphid resistance at a 47:209 (resistant:susceptible) ratio, indicating the two resistance sources have two different sets of resistance genes. The 47:209 ratio was the expected results of the following genotypic configuration: aabbCCDD × AABBccdd 47:209 (Resistant:Susceptible). Resistant: aabb----, ----ccdd, aa--cc--. Susceptible: A-B-C-D-, aaB-C---, A-bb----, A---ccD-, ----C-dd. PI 567597C and PI 567598B appeared to share resistant loci but with different alleles (see, Table 8).

| Population ID | Parents | No. of F2:3 line | No. of resistant F2:3 line | No. of susceptible F2:3 line | P value of X2 test (47R:209S) |
|---|---|---|---|---|---|
| 020138-1 | PI 567598B × PI 567541B | 193 | 34 | 159 | 0.79 |

TABLE 8

Progenies from the cross between PI 567597C and PI 567598B were resistant to soybean aphids indicating they have the same resistant loci. However, the resistant alleles are different because PI 567597C has antixenosis resistance while PI 567598B has antibiosis resistance.

| Population ID | Parents | No. of F2 plant | No. of resistant F2 Plant | No. of susceptible F2 Plant |
|---|---|---|---|---|
| 030100-1 | PI 567598B × PI 567597C | 541 | 541 | 0 |
| 030100-2 | PI 567598B × PI 567597C | 322 | 322 | 0 |
| 030100-3 | PI 567598B × PI 567597C | 356 | 356 | 0 |
| 030100-4 | PI 567598B × PI 567597C | 596 | 596 | 0 |

EXAMPLE 9

Molecular markers were found linked to genes conferring resistance to soybean aphids in PI 567598B and PI 567541B (Tables 9 and 10).

Linkage group analysis was used for identifying the linkage groups comprising aphid resistance germplasm. F2 populations from crosses between aphid resistant soybean and aphid susceptible soybean were evaluated for aphid resistance then tested with simple sequence repeat (SSR) DNA markers for identifying J, K, B2, D1a and D1b Linkage Groups comprising aphid resistant germplasm.

TABLE 9

Markers associated with aphid resistance in PI 567598B in single marker analysis. P-value less than or equal to 0.05 and 0.01 are indicated by * and ** respectively. Linkage group names and marker positions were obtained from the soybean composite map (Song, et al. (2004) Theor. Appl. Genet. 109: 122-128).

| Marker | Linkage Group | Position (cM) | Week 3 P-value | Week 4 P-value |
|---|---|---|---|---|
| Satt304 | B2 | 65.55 | 0.049* | 0.012* |
| Satt271 | D1b | 137.05 | 0.076 | 0.024* |
| Satt280 | J | 38.70 | 0.019* | 0.053 |
| Satt686 | J | 40.50 | 0.016* | 0.007** |
| Satt529 | J | 41.29 | 0.004** | 0.002** |
| Satt628 | K | 49.59 | 0.122 | 0.012* |

These results show that in particular, linkage group J showed the closest association with aphid resistance germplasm in PI 567598B plants.

TABLE 10

Markers associated with aphid resistance in PI 567541B in single marker analysis. P-value less than or equal to 0.05 and 0.01 are indicated by * and ** respectively. Linkage group names and marker positions were obtained from the soybean composite map (Song, et al. (2004) Theor. Appl. Genet. 109: 122-128).

| Marker | Linkage Group | Position (cM) | Week 3 P-value | Week 4 P-value |
|---|---|---|---|---|
| Satt468 | D1a | 69.91 | 0.118 | 0.030* |
| Satt439 | D1a | 72.26 | 0.023* | 0.089 |

These results show that in addition to the above linkage groups, linkage group D1a showed an association with aphid resistance germplasm in PI 567541B plants.

EXAMPLE 10

The inventors developed soybean breeding lines comprising economic and agronomic desirable traits for commercial development. The following Table 11 shows the parents, generation and preference order for development as a commercial soybean plant with aphid resistance.

TABLE 11

Breeding lines with antibiosis resistance to soybean aphids

| Line ID | Parents (Female × Male) | Current generations | Preference order |
|---|---|---|---|
| E06906 | Titan × PI 567598B | F4 derived F5 and F6 | 1 |
| E06902 | Titan × PI 567598B | F3 derived F4 and F5 | 2 |
| E06907 | E99034 × PI 567598B | F4 derived F5 and F6 | 3 |
| E06901 | Titan × PI 567598B | F3 derived F4 and F5 | 4 |
| E06904 | Titan × PI 567598B | F3 derived F4 and F5 | 5 |

EXAMPLE 11

This Example shows exemplary mapping of aphid resistance genes in soybean cultivar PI 567541B using molecular markers. Accession PI 567541B soybean plants were discovered during the course of developing the present inventions, as described herein, as containing aphid resistance germplasm with a plant phenotype that showed early maturity characteristics. Therefore, hundreds of PI 567541B plants, parental susceptible plants, and progeny plants thereof, were used for screening hundreds of markers for identifying regions of DNA in specific linkage groups for identifying polymorphic regions present in aphid resistant soybean plants that were not present in plants susceptible to aphid damage.

During the identification and development of sets of molecular markers useful to methods of the present inventions, a mapping population of at least 228 $F_3$ derived soybean plant lines was investigated for aphid resistance in both field and greenhouse trials. After testing hundreds of markers, the inventors discovered an exemplary set of markers showing unique banding patterns on regions within two quantitative trait loci (QTLs) associated with an aphid resistance phenotype using a composite interval mapping method. These two QTL regions were localized on soybean plant genetic linkage groups (LGs) F and M. After further testing, cultivars of PI 567541B plants were shown to have transferred resistant alleles at both QTL loci to their progeny aphid resistant plants. Therefore, in addition to identifying regions within at least 2 linkage groups associated with an aphid resistant phenotype, an additive X (times) additive interaction between these two QTL regions was identified using this multiple interval mapping method.

The presence of unique banding patterns within QTLs M and F, as a combination in soybean plants with a higher level of resistance than in soybean plants with either one alone, showed their additive interaction. This additive interaction is contemplated to explain the majority of the phenotypic variation in aphid resistance observed and measured in both field and greenhouse trials.

In general, the QTL region on LG F had less effect, less aphid resistance, than the one on LG M, especially in the greenhouse trial. These two QTLs were further validated using an additional independent population (a population of plants different than the mapping population. The effects of these two QTLs were also confirmed using 50 advanced breeding lines, which were all derived from PI 567541B and had various genetic backgrounds.

QTL Mapping
Plant Materials and Aphid Resistance Evaluation

A population of 228 F3-derived F4 lines was developed from the cross of PI 567541B×Skylla by single seed descent and was used for QTL detection. PI 567541B possesses antibiosis resistance to the soybean aphid (Mensah et al. 2005) while 'Skylla' (Wang et al. 2006) is an aphid susceptible cultivar.

Plant Materials and Aphid Resistance Evaluation

A population of 228 F3-derived F4 lines was developed from the cross of PI 567541B X Skylla by single seed descent and was used for QTL detection. PI 567541B possesses antibiosis resistance to the soybean aphid (Mensah et al. 2005) while 'Skylla' (Wang et al. 2006) is an aphidsusceptible cultivar.

One Field and one greenhouse trial were conducted for aphid resistance evaluation. In the summer of 2007, a Field trial was performed on the Agronomy Farm of Michigan State University (MSU). A polypropylene cage with the 0.49-mm size mesh (Redwood Empire Awning Co., Santa Rosa, Calif.), which was aphid- and predator-proof, was constructed over the Field experiment to create conditions for an artificial aphid infestation. The whole population (F3:4 generation) and its parents were randomly arranged in the Field plots without replication. Depending on the seed availability, two to twenty seeds per line were seeded in a single row plot, 60 cm long with a row spacing of 60 cm. The average number of plants per line was about 11 with most plots having at least ten plants. In the spring of 2008, a greenhouse trial was performed in the Plant Science Greenhouse on the MSU campus. In this trial, the whole population (F3:5 generation) and its parents were arranged in a randomized complete block design with two replications. In each replication, six seeds per line were seeded in a plastic pot. The pot size was 105 mm wide×105 mm long×125 mm deep. The greenhouse was maintained at a temperature of 26° C. by day, 15° C. by night, and sodium vapor lights were used to supplement light intensity during the day (14 h).

Both trials were choice tests for aphid resistance evaluation, which identifies resistance genotypes with either antibiosis or antixenosis. Each plant was inoculated with two wingless aphids at the V1 stage. The aphids inoculated in the Field trial were collected from the naturally infested Field on the Agronomy Farm of MSU during that year. The aphid inoculated in the greenhouse trial was a single clone, which was collected from the naturally infested Field on the Agronomy Farm of MSU in 2002 and has been maintained in the greenhouse ever since. Aphid resistance was visually rated for each plant 3 and 4 weeks after inoculation using a scale of 0-4 developed by Mensah et al. (2005, 2008), where 0=no aphids; 0.5=less than 10 aphids per plant, no colony formed; 1=11-100 aphids per plant, plant appears healthy; 1.5=101-150 aphids per plant, plant appears healthy; 2=151-300 aphids per plant, mostly on the young leaves or tender stems, plant appears healthy; 2.5=301-500 aphids per plant, plant appears healthy; 3=501-800 aphids per plant, young leaves and tender stems covered with aphids, leaves slightly curly and shiny; 3.5=more than 800 aphids per plant, plants stunted, leaves curled and slightly yellow, no sooty mold and few cast skins; 4=more than 800 aphids per plant, plant stunted, leaves severely curled and yellow, covered with sooty mold and cast skins. A damage index (DI) for each line was calculated by the following formula (Mensah et al. 2005): DI=(scale value X no. of plants in the category)/(4× total no. of plants)×100. The DI ranges between 0 for no infestation and 100 for the most severe damage. The DI was used as an indicator of aphid resistance and was applied in the following analysis.

DNA Extraction and Marker Analysis

At least ten plants for each line (F3:4 generation) and their parents were grown in the greenhouse for DNA extraction in 2007. The non-expanded trifoliates from each line were bulk-harvested for isolating the genomic DNA. The DNA was extracted with the CTAB (hexadecyltrimethyl ammonium bromide) method as described by Kisha et al. (1997) and the concentration was determined with a ND-1000 Spectrophotometer (NanoDrop Technologies, Inc., Wilmington, Del.). The PCR was performed using the genomic DNA with SSR markers as described by Cregan and Quigley (1997) and run on a MJ Tetrad™ thermal cycler (MJ Research, Waltham, Mass.). The PCR products were separated on 6% non-denaturing polyacrylamide gels using an electrophoresis unit DASG-400-50 (C.B.S. ScientiWc Co., Del Mar, Calif.) as described by Wang et al. (2003). Gels were stained with ethidium bromide, visualized under UV light, and photographed. A total of 1,056 SSR markers were screened for the parental polymorphism, of which 329 markers showed polymorphism. Based on the soybean consensus map (Song et al. 2004); these polymorphic markers covered most of the genomic regions. The SSR primer sequences were provided by Dr. Perry Cregan at USDA-ARS, Beltsville, Md. In order to accelerate the identification of genomic regions for aphid resistance, markers at an approximate distance of 20 cM were used to first genotype a subset of 94 lines, which were randomly selected from the whole population. The markers in regions potentially associated with aphid resistance were genotyped on the remaining lines and these regions were further saturated with more markers.

Statistical and QTL Analysis

The DI data from the Field and greenhouse trials were analyzed separately since their experimental designs and inoculums differed. Analysis of variance (ANOVA) was performed for the greenhouse data using the GLM procedure of SAS (1999). The broad sense heritability of DI in the greenhouse trial was calculated based on entry means according to Fehr (1987). Pearson correlation for the aphid resistance between trials was calculated with the CORR procedure of SAS (1999). Linkage map was constructed with the Kosambi function and a LOD score of 3 or lower (to force some distantly located markers to be linked) using Map Manager QTXb20 (Manly et al. 2001). The maps were drawn using MapChart (Voorrips 2002). Assignment of linkage groups to the specific linkage groups was based on the soybean consensus map (Song et al. 2004). Composite interval mapping (CIM) was performed to detect aphid resistance QTLs using QTL Cartographer V2.5 with the standard model zmapQTL 6 (Wang et al. 2008). Entry means were used in the analysis for the greenhouse trial data. The CIM analysis uses markers other than the interval being tested as cofactors to control the genetic background (Zeng 1994). The forward and backward regression method was used to select markers as cofactors. The walking speed chosen for CIM was 2 cM. The empirical LOD threshold at 5% probability level was determined by a 1,000-permutation test (Churchill and Doerge 1994). The QTL X QTL interaction was further determined using the multiple interval mapping (MIM) method of QTL Cartographer. The whole genome scan was only conducted on the subset of 94 lines.

QTL validation. A population of 51 F3-derived lines was developed by single-seed descent from a cross between PI 567541B and E00003, where E00003 is an elite advanced breeding line and is susceptible to the soybean aphid. This population and another 50 advanced breeding lines were used for the QTL validation. The 50 advanced breeding lines (F4 generation in the 2007 Field trial and F5 in the 2008 greenhouse trial) pre-selected for agronomic traits were derived from different crosses, where the male parent is PI 567541B or F1 progeny derived from PI 567541B, and the female parent is an aphid-susceptible cultivar or breeding line (Table 12). The same type of trials conducted for the mapping population were performed for the validation population and the advanced breeding lines in the summer of 2007 and spring of 2008. However, there was no replication in the greenhouse trial and the aphid resistance was only rated 4 weeks after inoculation in the Field trial. The DNA was extracted with a quick-extraction method (Bell-Johnson et al. 1998). Several markers in the QTL associated regions were genotyped for the validation population. Linkage maps were constructed and QTL analysis was performed in the same way as in the mapping population. For the advanced breeding lines, only markers closely linked to the identified QTLs were genotyped and their allele effects were calculated and compared using at test (P=0.05).

Phenotypic analysis The phenotypic values of the mapping population and its parents are summarized in Table 13. In the Field cage, susceptible parent Skylla was severely damaged by the aphid infestation while resistant parent PI 567541B had relatively lower DI than Skylla for both 3- and 4-week ratings.

TABLE 12

Crosses used for deriving the 50 advanced breeding lines

| Cross ID[a] | Male | Female | Line no. |
|---|---|---|---|
| 050016 | PI 567541B | E00003 | 2 |
| 050023 | (PI) 567541B × SDx00R-39-42) F1 | E00003 | 9 |
| 050027 | PI 567541B | E01260 | 7 |
| 050098 | PI 567541B | SDx00R-39-42 | 9 |
| 050105 | PI 567541B | Skylla | 23 |

[a]Crosses 050016 and 050105 have the same parents as in the mapping and validation population, but they were made independently in a different year.

Thus, in one embodiment, the two QTLs, LG F and LG M, identified and validated herein are contemplated for use in improving soybean aphid resistance by marker-assisted selection for these QTLs. In another embodiment, the marker-assisted selection for identifying the presence of aphid resistant germplasm in LG F and LG M

TABLE 13A [1]

Phenotypic summery of PI 567541B, Skylla, and 228 recombinant inbred lines (RILs) for soybean aphid resistance investigated in the field cage in summer 2007 and in the greenhouse in spring 2008

| Trials | Parents[a] | | RILs population | | | |
|---|---|---|---|---|---|---|
| | PI 567541B | Skylla | Mean | Range | SE | H[2b] |
| Field Cage | | | | | | |
| 3-week rating | 2.4a | 3.8b | 3.3 | 1.3 | 4.0 | — |
| 4-week rating | 3.0a | 4.0b | 3.7 | 2.0 | 4.0 | — |
| Greenhouse | | | | | | |
| 3-week rating | 1.0a | 2.3b | 1.8 | 0.7 | 3.2 | 0.90 |
| 4-week rating | 1.0a | 3.3b | 2.2 | 0.9 | 3.5 | 0.94 |

[a]Means followed different letters within the same row are significantly different at P < 0.05
[b]Broad sense heritability. Unavailable heritability is marked with '—'

TABLE 13B [1]

Phenotypic summery of PI 567541B, Skylla, and 228 recombinant inbred lines (RILs) for soybean aphid resistance investigated in the field cage in summer 2007 and in the greenhouse in spring 2008

| Trials | Parents[a] | | RILs population | | | |
|---|---|---|---|---|---|---|
| | PI 567541B | Skylla | Mean | Range | SE | H[2b] |
| Field Cage | | | | | | |
| 3-week rating | 60.0 | 95.8 | 82.2 | 32.5-100.0 | 16.3 | — |
| 4-week rating | 75.0 | 100.0 | 91.4 | 50.0-100.0 | 13.2 | — |

TABLE 13B [1]-continued

Phenotypic summery of PI 567541B, Skylla, and 228 recombinant inbred lines (RILs) for soybean aphid resistance investigated in the field cage in summer 2007 and in the greenhouse in spring 2008

| Trials | Parents[a] | | RILs population | | | |
|---|---|---|---|---|---|---|
| | PI 567541B | Skylla | Mean | Range | SE | H[2b] |
| Greenhouse | | | | | | |
| 3-week rating | 26.8a | 56.1b | 45.9 | 18.5-77.9 | 17.5 | 0.89 |
| 4-week rating | 25.0a | 81.3b | 55.7 | 22.3-87.9 | 24.1 | 0.93 |

[a]Means followed different letters within the same row are significantly different at P < 0.05
[b]Broad sense heritability. Unavailable heritability is marked with '—'

Figure 13A:
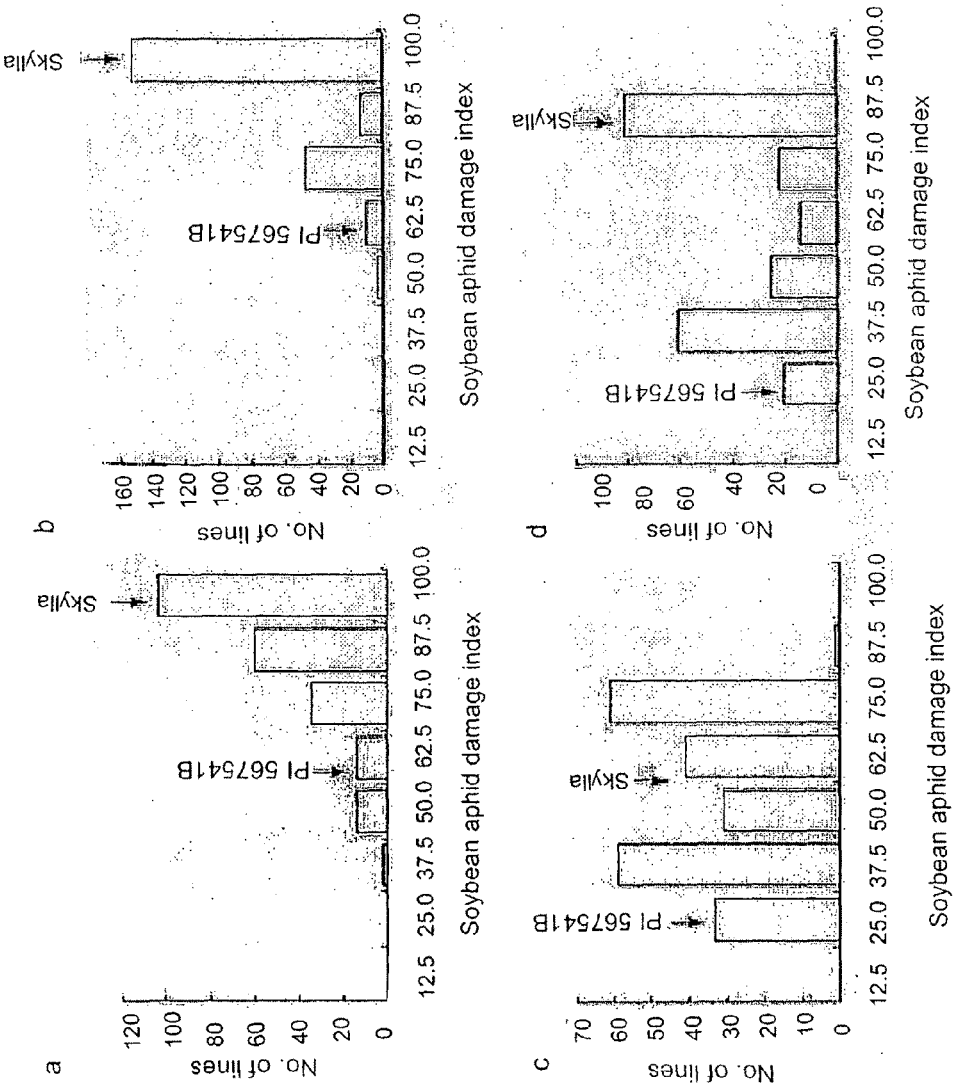
FIG. 13 shows an exemplary frequency distribution of aphid resistance for 228 recombinant inbred lines derived from a cross of PI 567541B×Skylla. A) aphid damage index where parents are shown by arrows. AA: 3-week rating in the Weld trial, AB: 4-week rating in the Field trial, AC: 3-week rating in the greenhouse trial, AD: 4-week rating in the greenhouse trial and B) aphid rating BA: three-week rating in the field trial; BB: four-week rating in the filed trial; BC: three-week rating in the greenhouse trial; BD: four-week rating in the greenhouse trial.
Figure 13B:
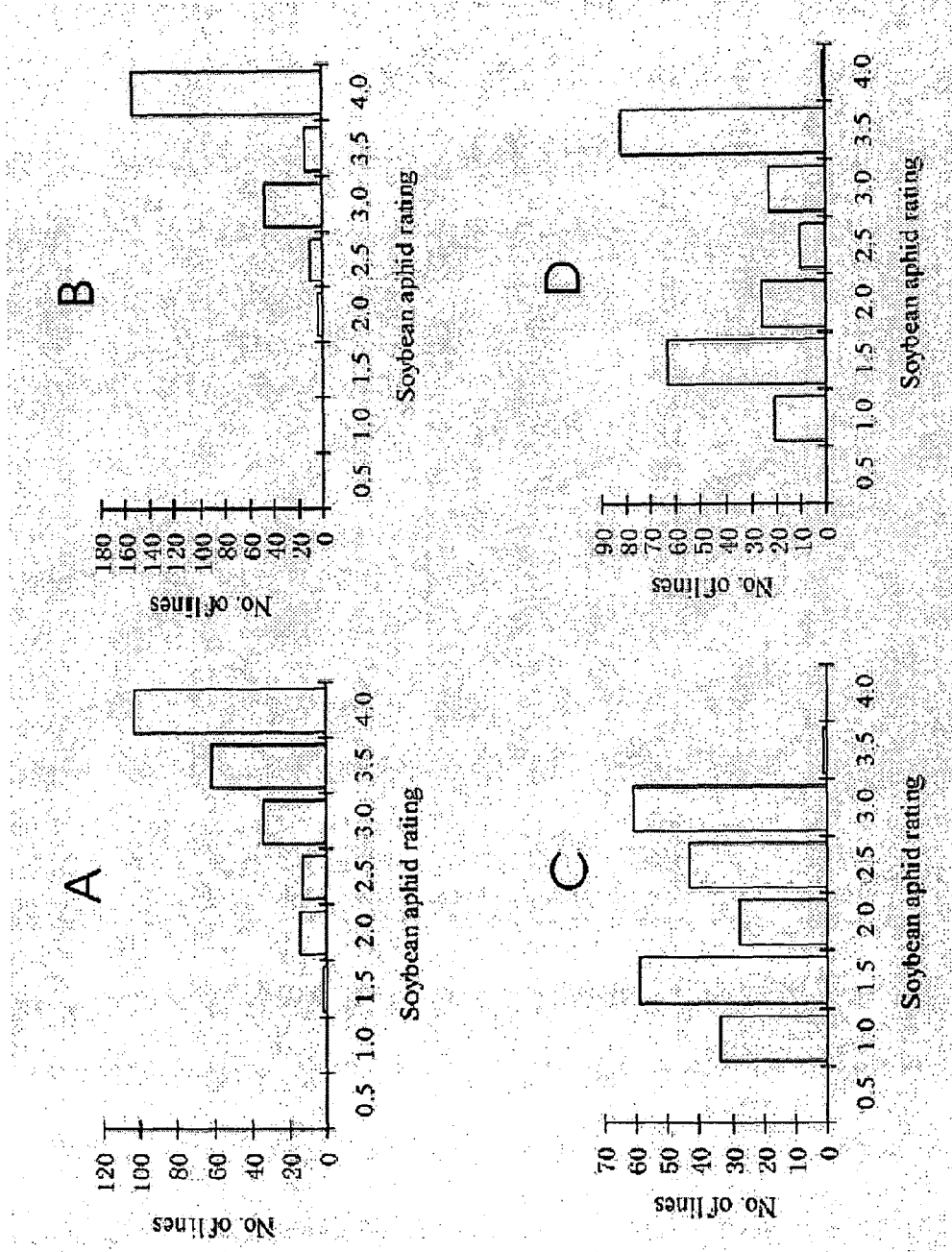

PI 567541B in the greenhouse trial had a significantly (P<0.05) lower DI than Skylla. Highly significant variation (P<0.0001) was observed among the population lines for both 3- and 4-week ratings in the greenhouse trial. The aphid infestation in the Field cage was generally more severe than in the greenhouse, which might be because the Field environment was more favorable for the aphid development. However, correlation coefficients between the Field and greenhouse data were signiWcant (0.68 and 0.66 for the 3- and 4-week ratings, respectively, P<0.0001). The frequency distributions of the Field DI were continuous, but not normal and skewed to the susceptible parent (FIG. 13 Aa, Ab), indicating that more than one recessive gene might control the aphid resistance. However, the frequency distributions of the greenhouse DI appeared more bimodal with a ratio of 1:1 (FIG. 13 Ac, Ad). Additionally, the broad sense heritability for the greenhouse DI was high (0.89 and 0.93 for the 3- and 4-week ratings, respectively) (Table 13). These might indicate that only one gene controls the aphid resistance in the greenhouse trial. QTL mapping using CIM.

A total of 123 SSR markers, which distribute throughout the soybean genome based on the consensus map (Song et al. 2004), were genotyped on the subset of 94 lines. These markers generated 131 loci, of which 124 loci were mapped into 25 linkage groups that were segments of the 20 linkage groups on the consensus map. The linkage map spanned 1,703 cM with an average interval length of 13.7 cM. This map was used to conduct the whole genome scan to identify aphid resistance QTLs with the subset of 94 lines. Two QTLs were detected, which were located on LGs F and M (Table 14). The PI 567541B allele conferred aphid resistance at both loci. The QTL on LG M was consistently detected for both 3- and 4-week ratings in each trial and explained a large portion of phenotypic variations ranging from 43.6 to 85.2%. The QTL on LG F was only associated with the 3-week rating in the Field trial and had much less effect (explained 9.1% of the phenotypic variation) than the one on LG M. However, using the whole population of 228 lines, these two QTLs were both consistently detected for both 3- and 4-week ratings in each trial (Table 14, FIG. 14). The QTL on LG M was closely linked to marker Satt299 or Satt435, which was only 3.6 cM away from Satt299. Its peak position was located at Satt299 or 2 cM below in most cases, but it shifted about 10 cM above for the 4-week rating in the Field trial, which might be due to the limited marker saturation in the region above Satt229. However, the genomic region around Satt299 could be conservatively declared as a major QTL region. The QTL on LG F was closely linked to marker Satt649 or Satt343, which was only 1.8 cM away from Satt649. Its peak position was located at Satt649 or 2 cM below. Although the QTL on LG F was signiWcant in the greenhouse trial, it only explained very little phenotypic variation (1.5 and 0.9% for the 3- and 4-week ratings, respectively) (Table 14). QTL mapping using MIM

TABLE 14A[3]

Summery of QTLs for soybean aphid resistance detected in the mapping population PI 567541B × Skylla using the composite interval mapping method

| Trials | LG[a] | Peak Pos.[b] | Flanking markers[c] | 94 RILs[d] LOD | $R^{2e}$ | $a^f$ | 228 RILs LOD | $R^2$ | a |
|---|---|---|---|---|---|---|---|---|---|
| Field Cage | | | | | | | | | |
| 3-week | M | 33.4 | Satt299 | 14.8 | 40.9 | 0.47 | 29.7 | 43.8 | 0.43 |
| rating | F | 5.1 | Satt649 | 4.9 | 10.3 | 0.24 | 8.2 | 9.5 | 0.14 |
| 4-week | M | 23.5 | Satt150-Satt435 | 25.9 | 77.6 | 0.54 | 34.1 | 79.0 | 0.51 |
| rating | F | 5.1 | Satt649 | — | — | — | 5.5 | 6.7 | 0.20 |
| Greenhouse | | | | | | | | | |
| 3-week | M | 35.4 | Satt299-Sat_244 | 33.2 | 81.7 | 0.65 | 62.0 | 77.2 | 0.61 |
| rating | F | 3.3 | Satt343 | — | — | — | 2.8 | 1.7 | 0.10 |
| 4-week rating | M | 35.4 | Satt299-Sat_244 | 33.2 | 83.2 | 0.73 | 64.1 | 79.6 | 0.70 |

[a] Linkage group
[b] QTL Peak position is expressed in cM and based on the analysis from the whole population (228 lines)
[c] Markers flanking the peak position or the marker at the peak position based on the analysis from the whole population (228 lines)
[d] A subset of 94 recombinant inbred lines. QTL not significant in the subset is marked with '—'
[e] $R^2$, percentage of phenotypic variation explained by QTL
[f] Additive effect. The positive value implies that PI 567541B allele decrease the phenotypic value.

TABLE 14[3]

Summery of QTLs for soybean aphid resistance detected in the mapping population PI 567541B × Skylla using the composite interval mapping method with additional markers.

| Trials | LG[a] | Peak Pos.[b] | Flanking markers[c] | 94 RILs[d] LOD | $R^{2e}$ | $a^f$ | 228 RILs LOD | $R^2$ | a |
|---|---|---|---|---|---|---|---|---|---|
| Field Cage | | | | | | | | | |
| 3-week | M | 33.4 | Satt299 | 15.4 | 43.6 | 12.4 | 30.4 | 44.7 | 10.9 |
| rating | F | 5.1 | Satt649 | 4.4 | 9.1 | 5.6 | 8.0 | 9.2 | 4.9 |
| 4-week | M | 23.5 | Satt150-Satt435 | 26.1 | 76.8 | 13.4 | 35.0 | 79.6 | 12.8 |
| rating | F | 5.1 | Satt649 | — | — | — | 5.2 | 6.3 | 3.3 |
| Greenhouse | | | | | | | | | |
| 3-week | M | 35.4 | Satt299-Sat_244 | 36.2 | 82.9 | 16.3 | 76.2 | 83.2 | 16.1 |
| rating | F | 7.1 | Satt649-Satt348 | — | — | — | 2.1 | 1.5 | 2.1 |
| 4-week | M | 35.4 | Satt299-Sat_244 | 40.8 | 85.2 | 22.4 | 87.9 | 87.7 | 22.5 |
| rating | F | 7.1 | Satt649-Satt348 | — | — | — | 1.8 | 0.9 | 2.3 |

[a] Linkage group
[b] QTL Peak position is expressed in cM and based on the analysis from the whole population (228 lines)
[c] Markers flanking the peak position or the marker at the peak position based on the analysis from the whole population (228 lines)
[d] A subset of 94 lines. The LOD threshold for this subset of lines is 2.8. The LOD threshold for the whole population (228 lines) is 1.8. QTL not significant in the subset is marked with '—'
[e] $R^2$, percentage of phenotypic variation explained by QTL
[f] Additive effect. The positive value implies that PI 567541B allele decrease the phenotypic value.

The data were also subjected to MIM analysis and the MIM results using the whole mapping population are presented in Table 15. The two QTLs identified with the CIM method were also found using the MIM method. Additionally, a significant additive £ additive interaction between these two QTLs was detected using the MIM method. For the 3-week rating in the Field trial, the LOD score of the QTL interaction was 10.3 and it explained 6.5% of the phenotypic variation. The two QTLs combined with their interaction explained 67.4% of the phenotypic variation. For the 4-week rating in the Field trial, the two QTLs combined with their interaction explained 87.2% of the phenotypic variation, of which the interaction explained 24.7%. The QTL position on LG M was refined to 38.4 cM. For the 3-week rating in the greenhouse trial, the two QTLs combined with their interaction explained 85.6% of the phenotypic variation, of which the major QTL on LG M explained 83.8% of the phenotypic variation while the QTL on LG F and the interaction only explained a very small portion (1.6 and 0.2%).

For the 4-week rating in the greenhouse trial, both QTLs were detected, but their interaction was not significant. These two QTLs explained 88.7% of the phenotypic variation, of which the major QTL on LG M explained 88.0%. Given the broad sense heritability of 0.89 and 0.93 for the 3- and 4-week ratings in the greenhouse trial, the major QTL on LG M accounted for 94.2 and 94.6% of the genetic variation, respectively.

TABLE 15A[4]

Summery of QTLs and interactions for soybean aphid resistance detected in the whole mapping population PI 567541B × Skylla and validation population PI 567541B × E00003 using the multiple interval mapping method.

| Population | Trials | LG[a] | Peak Pos.[b] | Flanking markers[c] | LOD | Genetic effect R[2d] | a[e] |
|---|---|---|---|---|---|---|---|
| PI 567541B × Skylla | Field Cage | | | | | | |
| | 3-week rating | M | 33.5 | Satt299-Sat_244 | 38.8 | 49.6 | 0.47 |
| | | F | 8.1 | Satt649-Satt348 | 12.5 | 10.9 | 0.23 |
| | | Interaction | | | 10.4 | 6.5 | 0.21 |
| | | Total | | | | 67.0 | |
| | 4-weak rating | M | 33.5 | Satt299-Sat_244 | 38.5 | 46.1 | 0.37 |
| | | F | 10.1 | Satt649-Satt348 | 13.9 | 14.1 | 0.21 |
| | | Interaction | | | 12.9 | 11.0 | 0.20 |
| | | Total | | | | 71.2 | |
| | Greenhouse | | | | | | |
| | 3-week rating | M | 35.4 | Satt299-Sat_244 | 82.1 | 85.3 | 0.66 |
| | | F | 6.1 | Satt649-Satt348 | 5.4 | 1.4 | 0.10 |
| | | Interaction | | | 1.8 | 0.2 | 0.06 |
| | | Total | | | | 86.9 | |
| | 4-weak rating | M | 35.4 | Satt299-Sat_244 | 95.7 | 89.4 | 0.92 |
| PI 567541B × E00003 | Field Cage | | | | | | |
| | 4-week rating | M | 17.4 | Satt435-Satt245 | 3.0 | 18.6 | 0.19 |
| | | F | 1.0 | Satt343 | 2.4 | 14.8 | 0.17 |
| | | Interaction | | | 2.1 | 14.6 | 0.16 |
| | | Total | | | | 48.0 | |
| | Greenhouse | | | | | | |
| | 3-week rating | M | 20.4 | Satt435-Satt245 | 4.9 | 43.4 | 0.40 |
| | 4-weak rating | M | 13.0 | Satt150-Satt299 | 14.4 | 81.4 | 0.68 |

[a]Linkage group
[b]QTL Peak position is expressed in cM
[c]Markers flanking the peak position or the marker at the peak position
[d]R[2], percentage of phenotypic variation explained by QTL
[e]Additive effect. The positive value implies that PI 567541B allele decrease the phenotypic value.

TABLE 15B[4]

Summary of QTLs and their interactions for soybean aphid resistance detected in the whole mapping population derived from PI 567541B × Skylla and in the validation population derived from PI 567541B × E00003 using the multiple interval mapping method.

| Population | Trials | LG[a] | Peak pos.[b] | Flanking markers[c] | LOD[d] | Genetic effect R[2e] | a[f] |
|---|---|---|---|---|---|---|---|
| PI 567541B × Skylla | Field cage 3-week rating | M | 33.4 | Satt299 | 39.6 | 50.3 | 12.0 |
| | | F | 8.1 | Satt649-Satt348 | 12.2 | 10.6 | 5.7 |
| | | Interaction | | | 10.3 | 6.5 | 5.3 |
| | | Total | | | | 67.4 | |

TABLE 15B[4]-continued

Summary of QTLs and their interactions for soybean aphid resistance detected in the whole mapping population derived from PI 567541B × Skylla and in the validation population derived from PI 567541B × E00003 using the multiple interval mapping method.

| Population | Trials | LG[a] | Peak pos.[b] | Flanking markers[c] | LOD[d] | Genetic effect R[2e] | a[f] |
|---|---|---|---|---|---|---|---|
| | 4-week rating | M | 38.4 | Satt299-Sat_244 | 43.8 | 36.7 | 7.5 |
| | | F | 10.1 | Satt649-Satt348 | 22.2 | 25.8 | 6.4 |
| | | Interaction | | | 21.3 | 24.7 | 6.4 |
| | | Total | | | | 87.2 | |
| | Greenhouse 3-week rating | M | 35.4 | Satt299-Sat_244 | 78.2 | 83.8 | 16.2 |
| | | F | 5.2 | Satt649-Satt348 | 5.7 | 1.6 | 2.6 |
| | | Interaction | | | 1.8 | 0.2 | 1.4 |
| | | Total | | | | 85.6 | |
| | 4-week rating | M | 35.4 | Satt299-Sat_244 | 91.8 | 88.0 | 22.6 |
| | | F | 6.1 | Satt649-Satt348 | 3.8 | 0.7 | 2.6 |
| PI 567541B × E00003 | Field cage 4-week rating | M | 8.1 | Satt150-Satt299 | 21.2 | 30.9 | 6.8 |
| | | F | 4.1 | Satt343 | 21.5 | 29.5 | 7.0 |
| | | Interaction | | | 20.4 | 34.7 | 6.8 |
| | | Total | | | | 95.2 | |
| | Greenhouse 3-week rating | M | 20.4 | Satt435-Satt245 | 4.9 | 43.7 | 9.9 |
| | 4-week rating | M | 13.0 | Satt150-Satt299 | 14.4 | 81.4 | 17.0 |

[a]Linkage group
[b]QTL peak position is expressed in cM
[c]Markers flanking the peak position or the marker at the peak position
[d]Using the same LOD threshold as in the composite interval mapping method. The LOD threshold for the mapping population is 1.8. The LOD threshold for the validation population is 1.7
[e]Percentage of phenotypic variation explained by a QTL
[f]Additive effect. The positive value implies that the PI 567541B allele decreases the phenotypic value QTL validation. Four and five markers around the QTLs identified on LGs F and M using the mapping population were genotyped on the validation population, respectively. The linkage maps for this validation population were similar as the mapping population except that the orders of a few tightly linked markers were switched (FIG. 14), which might be due to the small size of the validation population. Using both CIM and MINI methods, two QTLs were detected at similar regions as in the mapping population (Tables 15, 16; FIG. 14). Both QTLs were detected in the Field trial while only the major QTL on LG M was significant in the greenhouse trial. The interaction between these two QTLs was also significant in the Field trial (Table 16). The two QTLs combined with their interaction explained 95.2% of the phenotypic variation in the Field trial. Hence, the results from the validation population further confirmed the QTLs identified in the mapping population. The 50 advanced breeding lines were genotyped with the markers closely linked to the QTLs identified in the mapping population. The 50 advanced breeding lines were genotyped with the markers closely linked to the QTLs identified in the mapping population, which were Satt299, Satt435, Satt649, and Satt343. Table 17 summarized these allele effects for the aphid resistance. The DI for the breeding lines with the resistant allele (PI 567541B allele) from either Satt435 or Satt299 was significantly (P<0.05) lower than the ones with the corresponding susceptible allele in either Field or greenhouse trials. However, the resistant allele from Satt649 or Satt343 only had effects in the Field trial and for the 3-week rating in the greenhouse trial. This is consistent with our mapping results, where the QTL on LG F explained the least phenotypic variation for the 4-week rating in the greenhouse trial. Therefore, the allele effects in these advanced breeding lines further validated the QTLs identified in the mapping population. Band pattern analysis of markers linked to QTLs for aphid resistance.

Three parental lines, PI 567541B, Skylla, and E00003, together with two other aphid resistance germplasms, Dowling and Jackson, were genotyped using markers Satt299, Satt435, Satt649, and Satt343 that were tightly linked with the QTLs identified in this study. The band patterns of the PCR products from PI 567541B were different from those in Dowling and Jackson for all the four markers (FIG. 15), indicating that PI 567541B is a different resistance source than Dowling and Jackson. However, the band patterns between Dowling and Jackson were the same for each of the four markers. None of the band patterns in the susceptible genotypes Skylla and E00003 were the same as the ones in the three resistant genotypes.

TABLE 16A

Summery of QTLs for soybean aphid resistance detected in the validation population PI 567541B × E00003 using the composite interval mapping method.

| | | Peak | | Genetic effect | | |
|---|---|---|---|---|---|---|
| Trials | LG[a] | Pos.[b] | Flanking markers[c] | LOD | $R^{2d}$ | a[e] |
| Field Cage | | | | | | |
| 4-week rating | M | 16.4 | Satt435 | 2.5 | 16.6 | 0.18 |
| | F | 1.0 | Satt343 | 2.3 | 15.1 | 0.17 |
| Greenhouse | | | | | | |
| 3-week rating | M | 20.4 | Satt435-Satt245 | 5.1 | 40.1 | 0.38 |
| 4-week rating | M | 12.0 | Satt150-Satt299 | 15.6 | 80.5 | 0.68 |

[a]Linkage group
[b]QTL Peak position is expressed in cM
[c]Markers flanking the peak position or the marker at the peak position
[d]$R^2$, percentage of phenotypic variation explained by QTL
[e]Additive effect. The positive value implies that PI 567541B allele decrease the phenotypic value

TABLE 16B

Effects of alternative alleles at four soybean aphid resistance associated markers among the 50 advanced breeding lines, which were all derived from PI 567541B.

| | | | Average phenotypic value[c] | | |
|---|---|---|---|---|---|
| LG[a] | Marker | Allele[b] | Field cage | GH3WK | GH4WK |
| M | Satt299 | R (26) | 2.2a | 2.1a | 2.1a |
| | | S (17) | 2.8b | 2.6b | 3.0b |
| | Satt435 | R (33) | 2.0a | 2.0a | 2.0a |
| | | S (12) | 3.0b | 2.8b | 3.3b |
| F | Satt343 | R (23) | 1.9a | 2.1a | 2.2a |
| | | S (24) | 2.8b | 2.4b | 2.5a |
| | Satt649 | R (27) | 1.9a | 2.1a | 2.2a |
| | | S (23) | 2.8b | 2.4b | 2.5a |

[a]Linkage group
[b]Alternate alleles for each marker. R implies allele from resistant parent PI 567541B. S implies susceptible allele from another parent. The number in the parenthesis indicate the number of the lines, which had the allele
[c]Average phenotypic values from the lines with same allele. Field cage: four-week rating in the field cage trial. GH3WK: three-week rating in the greenhouse trial. GH4WK: four-week rating in the greenhouse trial.
Means from each pair of alleles followed same letter are not significant at P = 0.05

TABLE 17A

Summary of QTLs for soybean aphid resistance detected in the validation population PI 567541B × E00003 using the composite interval mapping method.

| | | Peak | | | Genetic effect | |
|---|---|---|---|---|---|---|
| Trials | LG[a] | Pos.[b] | Flanking markers[c] | $R^{2d}$ | $R^{2d}$ | $R^{2d}$ |
| Field cage | | | | | | |
| 4-week rating | M | 16.4 | Satt435 | 2.5 | 16.6 | 4.6 |
| | F | 1.0 | Satt343 | 2.3 | 15.1 | 4.4 |
| Greenhouse | | | | | | |
| 3-week rating | M | 20.4 | Satt435-Satt245 | 5.1 | 40.0 | 9.6 |
| 4-week rating | M | 12.0 | Satt150-Satt299 | 15.6 | 80.4 | 17.1 |

TABLE 17B

Effects of alternative alleles at four soybean aphid resistance associated markers among the 50 advanced breeding lines, which were all derived from PI 567541B

| | | | | Average phenotypic value[c] | |
|---|---|---|---|---|---|
| LG[a] | Marker | Allele[b] | Field cage | GH3WK | GH4WK |
| M | Satt299 | R (26) | 54.5a | 52.1a | 51.4a |
| | | S (17) | 69.1b | 64.7b | 75.0b |
| | Satt435 | R (33) | 49.1a | 51.7a | 50.3a |
| | | S (12) | 75.0b | 69.0b | 82.2b |
| F | Satt649 | R (27) | 46.8a | 52.7a | 55.3a |
| | | S (23) | 68.8b | 59.7b | 64.2a |
| | Satt343 | R (23) | 46.8a | 52.1a | 55.7a |
| | | S (24) | 67.3b | 59.7b | 63.3a |

[a]Linkage group
[b]Alternate alleles for each marker. R implies allele from resistant parent PI 567541B. S implies susceptible allele from another parent. The number in the parentheses indicates the number of the lines that had the allele
[c]Average soybean aphid damage index for the lines with the same allele. Field cage: 4-week rating in the Weld cage trial. GH3WK: 3-week rating in the greenhouse trial. GH4WK: 4-week rating in the greenhouse trial.
Means from each pair of alleles followed by the same letter are not signifcant at P = 0.05

EXAMPLE 12

This example shows the linkage group makers discovered by the inventors during the development of the present inventions. for identifying the aphid resistant germplasm from each founder aphid resistant cultivar. These linkage groups and markers were used in some embodiments and contemplated for use in other embodiments in compositions and methods of the present inventions.

TABLE 18

Markers linked to aphid resistance genes in soybean plant cultivars PI 567541B.

| Marker name | Linkage Group on consensus map by Song et al. 2004*. | Position on consensus map by Song et al. 2004. cm | P value in single marker analysis | P value in composite interval mapping |
|---|---|---|---|---|
| Satt343 | F | 3.04 cm | <0.001 | <0.0001 |
| Satt193 | F | 3.42 cm | <0.004 | <0.0001 |
| Satt649 | F | 5.36 cm | <0.0001 | <0.0001 |
| Satt150 | M | 18.58 cm | <0.002 | <0.001 |
| Satt435 | M | 38.94 cm | <0.0001 | <0.0001 |
| Satt299 | M | 42.23** cm | <0.0001 | <0.0001 |

*Song, et al., (2004) Theor Appl Genet 109: 122-128, herein incorporated by reference.
**Estimated position on consensus map by Song et al. 2004, supra.

TABLE 19

Markers linked to aphid resistance genes in soybean plant cultivars PI 567543C.

| Marker name | Linkage Group on consensus map by Song et al. 2004. | Position on consensus map by Song et al. 2004. cm | P value in single marker analysis | P value in composite interval mapping |
|---|---|---|---|---|
| Sat_339 | J | 27.97 cm | <0.0001 | <0.0001 |
| Satt414 | J | 37.04 cm | <0.0001 | <0.0001 |
| Satt654 | J | 38.1 cm | <0.0001 | <0.0001 |
| Satt596 | J | 39.64 cm | <0.0001 | <0.0001 |
| Satt686 | J | 40.5 cm | <0.0001 | <0.0001 |
| Satt622 | J | 42.25 cm | <0.0001 | <0.0001 |

*Song, et al., (2004) Theor Appl Genet 109: 122-128, herein incorporated by reference.
**Estimated position on consensus map by Song et al. 2004, supra.

TABLE 20

Markers linked to aphid resistance genes in soybean plant cultivars PI 567597C.

| Marker name | Linkage Group on consensus map by Song et al. 2004. | Position on consensus map by Song et al. 2004. cm | P value in single marker analysis | P value in composite interval mapping |
|---|---|---|---|---|
| Satt380 | J | 38.70 cm | <0.0001 | na |
| Satt596 | J | 39.64 cm | <0.0001 | <0.0001 |
| Satt456 | J | 40.83 cm | <0.0001 | <0.0001 |
| Satt529 | J | 41.90 cm | <0.0001 | <0.003 |
| Satt183 | J | 42.51 cm | <0.0001 | <0.0001 |
| Satt215 | J | 44.08 cm | <0.0001 | na |
| Sat_366 | J | 52.84 cm | <0.0001 | na |
| Sat_350 | J | 55.73 cm | <0.0001 | na |

TABLE 21

Markers linked to aphid resistance genes in soybean plant cultivars PI 567598B.

| Marker name | Linkage Group on consensus map by Song et al. 2004. | Position on consensus map by Song et al. 2004. cm | P value in single marker analysis | P value in composite interval mapping |
|---|---|---|---|---|
| Sct_046 | J | 23.8 cm | <0.005 | na |
| Sat_228 | J | 24.1 cm | 0.159 | na |
| Satt285 | J | 25.51 cm | <0.0001 | <0.003 |
| Satt414 | J | 37.04 cm | <0.006 | na |
| Sct_065 | J | 39.81 cm | <0.001 | na |
| Satt406 | J | 41.05 cm | <0.0001 | na |
| Satt596 | J | 42.59 cm | <0.0001 | <0.003 |
| Satt529 | J | 44.59 cm | <0.0001 | <0.0001 |
| Satt380 | J | 45.41 cm | <0.0001 | <0.042 |
| Sat_255 | J | 46.03 cm | <0.0001 | na |
| Satt215 | J | 46.43 cm | <0.0001 | na |
| Satt280 | J | 49.14 cm | <0.0001 | <0.004 |
| Sat_366 | J | 55.73 cm | <0.0001 | na |
| Satt540 | M | 32.17 cm | <0.0001 | na |
| Satt567 | M | 33.47 cm | <0.003 | <0.037 |
| Satt435 | M | 38.94 cm | <0.006 | <0.041 |
| satt463 | M | 47.45 cm | <0.0001 | na |

*Song, et al., (2004) Theor Appl Genet 109: 122-128, herein incorporated by reference.
**Estimated position on consensus map by Song et al. 2004, supra.

TABLE 22

Sequence of PCR Primers for Markers linked to aphid resistance genes in PI 567541B.

| Marker name * | Linkage Group * | Forward primer (F) * | Reverse primer (R) * | SEQ ID NOs: F-R |
|---|---|---|---|---|
| Satt343 | F | CATGGCGGAAAGCGAAACA | TCCCAATTCACCTCTTCA | SEQ ID NOs: 17-18 |
| Satt193 | F | GCGTTTCGATAAAAATGTTACACCTC | TGTTCGCATTATTGATCAAAAAT | SEQ ID NOs: 19-20 |
| Satt649 | F | TTACTGGCCGTGTTTACCCGTGTAA | GCGGACGTTATAAGATTTTTTTATCATG | SEQ ID NOs: 21-22 |
| Satt150 | M | AAGCTTGAGGTTATTCGAAAATGAC | TGCCATCAGGTTGTGTAAGTGT | SEQ ID NOs: 23-24 |
| Satt435 | M | GCGGTGAAACGGCTCTCTTTGATAGTGA | GCGTTGGATTAATTAATTAAATTATTTT | SEQ ID NOs: 25-26 |
| Satt299 Sat_299 | M | GCGACAAGGCACTCACATCTCTTCTC | GCGCTACCCATAACAAAAGTTCAAATC | SEQ ID NOs: 27-28 |

* Grant et al., (2008) SoyBase, The USDA-ARS Soybean Genome Database. (soybase.agron.iastate.edu.) Cited Oct. 30, 2008; Cregan, et al., Crop Sci 39: 1464-1490 (1999), (soybase.org/resources/ssr.php#misc); all of which is herein incorporated by reference in their entirety. hypertext transfer protocol site: crop.scijournals.org/cgi/content/full/39/5/1464?ijkey=3943de8a8b441cf631d216d7f70b4497e2c65ec3

TABLE 23

Sequence of PCR Primers for Markers linked to aphid resistance genes in PI 567543C.

| | | | | |
|---|---|---|---|---|
| Sat_339 | J | GCGTTCATCGAAATGCGTTTAGGATA | GCGACTGATATGCACCTCTAAGTCTCAA | SEQ ID NOs: 29-30 |
| Satt414 | J | GCGTATTCCTAGTCACATGCTATTTCA | GCGTCATAATAATGCCTAGAACATAAA | SEQ ID NOs: 31-32 |
| Satt654 | J | AGACGCGCACACAAGCATATA | GCTGGGACTCCTCATGTC | SEQ ID NOs: 33-34 |

TABLE 23-continued

Sequence of PCR Primers for Markers linked to aphid resistance genes in PI 567543C.

| Marker | | Forward | Reverse | SEQ ID |
|---|---|---|---|---|
| Satt596 | J | TCCCTTCGTCCACCAAAT | CCGTCGATTCCGTACAA | SEQ ID NOs: 35-36 |
| Satt686 | J | ACGGAAAATAAATGAAACTAAGA | GCGCTATCAGATAGAGAAGCAGAAGAAT | SEQ ID NOs: 37-38 |
| Satt622 | J | GCGGTGTAGGTAATAATTTTAATTCTCAT | GCGGTGTAGGTTTCACACTTCATTCAC | SEQ ID NOs: 39-40 |

* Grant et al., (2008) SoyBase, The USDA-ARS Soybean Genome Database. (soybase.agron.iastate.edu.) Cited Oct. 30, 2008; Cregan, et al., Crop Sci 39: 1464-1490 (1999), (soybase.org/resources/ssr.php#misc); all of which is herein incorporated by reference in their entirety.

TABLE 24

Sequence of PCR Primers for Markers linked to aphid resistance genes in PI 567597C.

| Marker | | Forward | Reverse | SEQ ID |
|---|---|---|---|---|
| Satt380 | J | GCGAGTAACGGTCTTCTAACAAGGAAAG | GCGTGCCCTTACTCTCAAAAAAAAA | SEQ ID NOs: 41-42 |
| Satt596 | J | TCCCTTCGTCCACCAAAT | CCGTCGATTCCGTACAA | SEQ ID NOs: 43-44 |
| Satt456 | J | GGGCCTTCGTTTGAGTTCATAG | GGGATCATTGGTTAATTGTTGTAAGA | SEQ ID NOs: 45-46 |
| Satt529 | J | GCGCATTAAGGCATAAAAAAGGATA | GCACAATGACAATCACATACA | SEQ ID NOs: 47-48 |
| Satt183 | J | TAGGTCCCAGAATTTCATTG | CACCAACCAGCACAAAA | SEQ ID NOs: 49-50 |
| Satt215 | J | GCGCCTTCTTCTGCTAAATCA | CCCATTCAATTGAGATCCAAAATTAC | SEQ ID NOs: 51-52 |
| Sat_366 | J | GCGGCACAAGAACAGAGGAAACTATT | GCGGACATGGTACATCTATATTACGAGTATT | SEQ ID NOs: 53-54 |
| Sat_350 | J | GCGTAAGAGCATCTCCAAACCATCAAACTCA | GCGATTTATTACATTTAACAATTGTTATTTA | SEQ ID NOs: 55-56 |

* Grant et al., (2008) SoyBase, The USDA-ARS Soybean Genome Database. (soybase.agron.iastate.edu.) Cited Oct. 30, 2008; Cregan, et al., Crop Sci 39: 1464-1490 (1999), (soybase.org/resources/ssr.php#misc); all of which is herein incorporated by reference in their entirety.

TABLE 25

Sequence of PCR Primers for Markers linked to aphid resistance genes in PI 567598B.

| Marker | | Forward | Reverse | SEQ ID |
|---|---|---|---|---|
| Sct_046 Satt046 | J | AAAATAACTAAAATGTCTTCTCA | TTGGTCAGATTATTATAAGATTG | SEQ ID NOs: 57-58 |
| Sat_228 | J | GCGTGACTACGGGAAGTTGGAAC | GCGTTGGCGGTAAGAGCACTATA | SEQ ID NOs: 59-60 |
| Satt285 | J | GCGACATATTGCATTAAAAACATACTT | GCGGACTAATTCTATTTTACACCAACAAC | SEQ ID NOs: 61-62 |
| Satt414 | J | GCGTATTCCTAGTCACATGCTATTTCA | GCGTCATAATAATGCCTAGAACATAAA | SEQ ID NOs: 63-64 |

TABLE 25-continued

Sequence of PCR Primers for Markers linked to aphid resistance genes in PI 567598B.

| | | | | |
|---|---|---|---|---|
| Sct_065 | J | CCCTGTGTTTCCCTCT | GAAAAGTTTTATGTTCTGAGTG | SEQ ID-NOs: 65-66 |
| Satt406 | J | GCGTGAGCATTTTTGTTT | TGACGGGTTTAATAGCAT | SEQ ID-NOs: 67-68 |
| Satt596 | J | TCCCTTCGTCCACCAAAT | CCGTCGATTCCGTACAA | SEQ ID-NOs: 69-70 |
| Satt529 | J | GCGCATTAAGGCATAAA AAAGGATA | GCACAATGACAATCACATACA | SEQ ID-NOs: 71-72 |
| Satt380 | J | GCGAGTAACGGTCTTCTA ACAAGGAAAG | GCGTGCCCTTACTCTCAAAAAA AAA | SEQ ID-NOs: 73-74 |
| Sat_255 | J | GCGGCATGTCATGGTATA CGTAACTTTAGA | GCGCAACTGAAGCAAGAAAAG AAACCT | SEQ ID NOs: 75-76 |
| Satt215 | J | GCGTAGCAACAAAGCAA TCTACAG | GCGTCCCATTTTATTCCACACT ATGTAAT | SEQ ID-NOs: 77-78 |
| Satt280 | J | GGCGGTGGATATGAAAC TTCAATAACTACAA | GGCGGGCTTCAAATAATTACTA TAAAACTACGG | SEQ ID-NOs: 79-80 |
| Sat_366 | J | GCGGCACAAGAACAGAG GAAACTATT | GCGGACATGGTACATCTATATT ACGAGTATT | SEQ ID-NOs: 81-82 |
| Satt540 | M | CTGGCGAATCAAGCTTTG TAAC | CCGTGATTGCGAAGAGGATATT | SEQ ID-NOs: 83-84 |
| Satt567 | M | GGCTAACCCGCTCTATGT | GGGCCATGCACCTGCTACT | SEQ ID-NOs: 85-86 |
| Satt435 | M | CAAGCTCAAGCCTCACAC AT | TGACCAGAGTCCAAAGTTCATC | SEQ ID-NOs: 87-88 |
| satt463 | M | TTGGATCTCATATTCAAA CTTTCAAG | CTGCAAATTTGATGCACATGTG TCTA | SEQ ID-NOs: 89-90 |

* Grant et al., (2008) SoyBase, The USDA-ARS Soybean Genome Database. (soybase.agron.iastate.edu.) Cited Oct. 30, 2008; Cregan, et al., Crop Sci 39: 1464-1490 (1999), (soybase.org/resources/ssr.php#misc); all of which is herein incorporated by reference in their entirety.

All publications and patents mentioned in the above specification are herein Incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method of breeding soybean for aphid resistance, comprising,
    a) providing,
        i) a first soybean plant comprising aphid resistant germplasm, wherein said first soybean plant is selected from the group consisting of accession PI567598B, accession PI567543C, accession PI567541B, accession PI567597C, line E06902 deposited under ATCC accession No: PTA-8794, and progeny thereof,
        ii) a second soybean plant, wherein said second soybean plant is an elite soybean plant, and
        iii) a molecular marker, wherein said marker is selected from the group consisting of a marker that identifies a region of a linkage group, wherein said linkage group is selected from the group consisting of F, M, and J, and a DNA marker, wherein said DNA marker is selected from the group consisting of Satt343, Satt193, Satt649, Satt150, Satt435, Sat_299, Sat_339, Satt414, Satt654, Satt596, Satt622, Satt380, Satt596, Satt456, Satt183, Satt215, Sat_366, and Sat_350; and
    b) crossing said first soybean plant with said second soybean plant for breeding a progeny soybean plant with aphid resistance, and
    c) using said molecular marker for identifying germplasm associated with aphid resistance in said progeny soybean plant.

2. The method of claim 1, wherein said marker for linkage group F is selected from the group consisting of Satt343, Satt193, and Satt649.

3. The method of claim 1, wherein said marker for linkage group M is selected from the group consisting of Satt150, Satt435, and Sat_299.

4. The method of claim 1, wherein said second soybean plant is an elite soybean plant selected from the group consisting of aphid resistant soybean plants and aphid susceptible soybean plants.

5. The method of claim 1, wherein said crossing further comprises one or more of a backcrossing, an outcrossing, and a self-crossing.

6. The method of claim 1, wherein said crossing creates soybean seed.

7. The method of claim 1, wherein said seed is germinated and grown into progeny soybean plants.

8. The method of claim 7, wherein said progeny soybean plants provide germplasm for use with said markers.

9. The method of claim 1, wherein said using said markers is identifying the aphid resistant germplasm in the first soybean plants.

10. A method for identifying aphid resistant soybean germplasm, comprising,
    a) providing,
        i) a soybean plant comprising aphid resistant germplasm, wherein said soybean plant is selected from the group consisting of accession PI567598B, accession PI567543C, accession PI567541B, accession PI567597C, line E06902 deposited under ATCC accession No: PTA-8794, and progeny thereof,
        ii) a molecular marker, wherein said marker is selected from the group consisting of a marker that identifies a region of a linkage group, wherein said linkage group is selected from the group consisting of F, M, and J, and a DNA marker, wherein said DNA marker is selected from the group consisting of Satt343, Satt193, Satt649, Satt150, Satt435, Sat_299, Sat_339, Satt414, Satt654, Satt596, Satt622, Satt380, Satt596, Satt456, Satt183, Satt215, Sat_366 and Sat_350, and
    b) using said molecular marker for identifying aphid resistant germplasm in a soybean plant.

11. The method of claim 10, further comprising testing a line of said soybean plants for an aphid resistant phenotype.

12. The method of claim 1, further comprising the step of testing said progeny soybean plant for an aphid resistant phenotype using a molecular marker selected from the group consisting of Satt271, Satt280, Satt304, Satt439, Satt468, Satt529, Satt628, and Satt686.

* * * * *

SEQUENCE LISTING

<160> NUMBER OF SEQ ID NOS: 90

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
gttgcagttg tgcgtgggag agag                                      24

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
gcgacatagc taattaagta agtt                                      24

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
gcggaatctg cttattcatt gtgtg                                     25

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
gcgccatgct gtaacacgtc aat                                       23

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
gggtagtgac gtatttcatg gtc                                       23

<210> SEQ ID NO 6
<211> LENGTH: 27
<212> TYPE: DNA
<213> ORGANISM: Artificial Sequence
<220> FEATURE:
<223> OTHER INFORMATION: Synthetic

<400> SEQUENCE: 6
gcgtaaaaac attcgttgac tacataa                                   27

<210> SEQ ID NO 7
<211> LENGTH: 28
<212> TYPE: DNA
<213> ORGANISM: Artificial Sequence
<220> FEATURE:
<223> OTHER INFORMATION: Synthetic

<400> SEQUENCE: 7
gcgaaaatga ttaaattgtt ttctcaag                                  28

```
<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
gcggcacgtt gccatataag ataaagg                                    27

<210> SEQ ID NO 9
<211> LENGTH: 28
<212> TYPE: DNA
<213> ORGANISM: Artificial Sequence
<220> FEATURE:
<223> OTHER INFORMATION: Synthetic

<400> SEQUENCE: 9
gcgtctctta ttttgacctt tttaactt                                   28

<210> SEQ ID NO 10
<211> LENGTH: 28
<212> TYPE: DNA
<213> ORGANISM: Artificial Sequence
<220> FEATURE:
<223> OTHER INFORMATION: Synthetic

<400> SEQUENCE: 10
gcgttttgta tttggtctat ctgcttag                                   28

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
gcgcattaag gcataaaaaa ggata                                      25

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
gcacaatgac aatcacatac a                                          21

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
ctacctttaa ggtcgttttc aagt                                       24

<210> SEQ ID NO 14
<211> LENGTH: 24
<212> TYPE: DNA
<213> ORGANISM: Artificial Sequence
<220> FEATURE:
<223> OTHER INFORMATION: Synthetic
```

-continued

<400> SEQUENCE: 14
gcatgctcct tttatgctcc tttt                                          24

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
acggaaaata aatgaaacta aga                                           23

<210> SEQ ID NO 16
<211> LENGTH: 28
<212> TYPE: DNA
<213> ORGANISM: Artificial Sequence
<220> FEATURE:
<223> OTHER INFORMATION: Synthetic

<400> SEQUENCE: 16
gcgctatcag atagagaagc agaagaat                                      28

<210> SEQ ID NO 17
<211> LENGTH: 19
<212> TYPE: DNA
<213> ORGANISM: Artificial Sequence
<220> FEATURE:
<223> OTHER INFORMATION: Synthetic

<400> SEQUENCE: 17
catggcggaa agcgaaaca                                                19

<210> SEQ ID NO 18
<211> LENGTH: 18
<212> TYPE: DNA
<213> ORGANISM: Artificial Sequence
<220> FEATURE:
<223> OTHER INFORMATION: Synthetic

<400> SEQUENCE: 18
tcccaattca cctcttca                                                 18

<210> SEQ ID NO 19
<211> LENGTH: 26
<212> TYPE: DNA
<213> ORGANISM: Artificial Sequence
<220> FEATURE:
<223> OTHER INFORMATION: Synthetic

<400> SEQUENCE: 19
gcgtttcgat aaaaatgtta cacctc                                        26

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20
tgttcgcatt attgatcaaa aat                                           23

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
ttactggccg tgtttacccg tgtaa                                         25

<210> SEQ ID NO 22
<211> LENGTH: 28
<212> TYPE: DNA
<213> ORGANISM: Artificial Sequence
<220> FEATURE:
<223> OTHER INFORMATION: Synthetic

<400> SEQUENCE: 22
gcggacgtta taagattttt ttatcatg                                      28

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23
aagcttgagg ttattcgaaa atgac                                         25

<210> SEQ ID NO 24
<211> LENGTH: 22
<212> TYPE: DNA
<213> ORGANISM: Artificial Sequence
<220> FEATURE:
<223> OTHER INFORMATION: Synthetic

<400> SEQUENCE: 24
tgccatcagg ttgtgtaagt gt                                            22

<210> SEQ ID NO 25
<211> LENGTH: 28
<212> TYPE: DNA
<213> ORGANISM: Artificial Sequence
<220> FEATURE:
<223> OTHER INFORMATION: Synthetic

<400> SEQUENCE: 25
gcggtgaaac ggctctcttt gatagtga                                      28

<210> SEQ ID NO 26
<211> LENGTH: 28
<212> TYPE: DNA
<213> ORGANISM: Artificial Sequence
<220> FEATURE:
<223> OTHER INFORMATION: Synthetic

<400> SEQUENCE: 26
gcgttggatt aattaattaa attattttt                                     28

<210> SEQ ID NO 27
<211> LENGTH: 26
<212> TYPE: DNA
<213> ORGANISM: Artificial Sequence
<220> FEATURE:
<223> OTHER INFORMATION: Synthetic

<400> SEQUENCE: 27
gcgacaaggc actcacatct cttctc                                        26

<210> SEQ ID NO 28
<211> LENGTH: 28
<212> TYPE: DNA
<213> ORGANISM: Artificial Sequence
<220> FEATURE:
<223> OTHER INFORMATION: Synthetic

<400> SEQUENCE: 28
gcgctaccca taacaaaaag ttcaaatc                                      28

<210> SEQ ID NO 29
<211> LENGTH: 26
<212> TYPE: DNA
<213> ORGANISM: Artificial Sequence
<220> FEATURE:
<223> OTHER INFORMATION: Synthetic

<400> SEQUENCE: 29
gcgttcatcg aaatgcgttt aggata                                        26

<210> SEQ ID NO 30
<211> LENGTH: 28
<212> TYPE: DNA
<213> ORGANISM: Artificial Sequence
<220> FEATURE:
<223> OTHER INFORMATION: Synthetic

<400> SEQUENCE: 30
gcgactgata tgcacctcta agtctcaa                                      28

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
gcgtattcct agtcacatgc tatttca                                       27

<210> SEQ ID NO 32
<211> LENGTH: 27
<212> TYPE: DNA
<213> ORGANISM: Artificial Sequence
<220> FEATURE:
<223> OTHER INFORMATION: Synthetic

<400> SEQUENCE: 32
gcgtcataat aatgcctaga acataaa                                       27

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
agacgcgcac acaagcatat a                                             21

```
<210> SEQ ID NO 34
<211> LENGTH: 18
<212> TYPE: DNA
<213> ORGANISM: Artificial Sequence
<220> FEATURE:
<223> OTHER INFORMATION: Synthetic

<400> SEQUENCE: 34
gctgggactc ctcatgtc                                                 18

<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35
tcccttcgtc caccaaat                                                 18

<210> SEQ ID NO 36
<211> LENGTH: 17
<212> TYPE: DNA
<213> ORGANISM: Artificial Sequence
<220> FEATURE:
<223> OTHER INFORMATION: Synthetic

<400> SEQUENCE: 36
ccgtcgattc cgtacaa                                                  17

<210> SEQ ID NO 37
<211> LENGTH: 23
<212> TYPE: DNA
<213> ORGANISM: Artificial Sequence
<220> FEATURE:
<223> OTHER INFORMATION: Synthetic

<400> SEQUENCE: 37
acggaaaata aatgaaacta aga                                           23

<210> SEQ ID NO 38
<211> LENGTH: 28
<212> TYPE: DNA
<213> ORGANISM: Artificial Sequence
<220> FEATURE:
<223> OTHER INFORMATION: Synthetic

<400> SEQUENCE: 38
gcgctatcag atagagaagc agaagaat                                      28

<210> SEQ ID NO 39
<211> LENGTH: 29
<212> TYPE: DNA
<213> ORGANISM: Artificial Sequence
<220> FEATURE:
<223> OTHER INFORMATION: Synthetic

<400> SEQUENCE: 39
gcggtgtagg taataatttt aattctcat                                     29

<210> SEQ ID NO 40
<211> LENGTH: 27
<212> TYPE: DNA
<213> ORGANISM: Artificial Sequence
<220> FEATURE:
<223> OTHER INFORMATION: Synthetic
```

```
<400> SEQUENCE: 40
gcggtgtagg tttcacactt cattcac                                          27

<210> SEQ ID NO 41
<211> LENGTH: 28
<212> TYPE: DNA
<213> ORGANISM: Artificial Sequence
<220> FEATURE:
<223> OTHER INFORMATION: Synthetic

<400> SEQUENCE: 41
gcgagtaacg gtcttctaac aaggaaag                                         28

<210> SEQ ID NO 42
<211> LENGTH: 25
<212> TYPE: DNA
<213> ORGANISM: Artificial Sequence
<220> FEATURE:
<223> OTHER INFORMATION: Synthetic

<400> SEQUENCE: 42
gcgtgcccct actctcaaaa aaaaa                                            25

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
tcccttcgtc caccaaat                                                    18

<210> SEQ ID NO 44
<211> LENGTH: 17
<212> TYPE: DNA
<213> ORGANISM: Artificial Sequence
<220> FEATURE:
<223> OTHER INFORMATION: Synthetic

<400> SEQUENCE: 44
ccgtcgattc cgtacaa                                                     17

<210> SEQ ID NO 45
<211> LENGTH: 22
<212> TYPE: DNA
<213> ORGANISM: Artificial Sequence
<220> FEATURE:
<223> OTHER INFORMATION: Synthetic

<400> SEQUENCE: 45
gggccttcgt ttgagttcat ag                                               22

<210> SEQ ID NO 46
<211> LENGTH: 26
<212> TYPE: DNA
<213> ORGANISM: Artificial Sequence
<220> FEATURE:
<223> OTHER INFORMATION: Synthetic

<400> SEQUENCE: 46
gggatcattg gttaattgtt gtaaga                                           26
```

```
<210> SEQ ID NO 47
<211> LENGTH: 25
<212> TYPE: DNA
<213> ORGANISM: Artificial Sequence
<220> FEATURE:
<223> OTHER INFORMATION: Synthetic

<400> SEQUENCE: 47
gcgcattaag gcataaaaaa ggata                                       25

<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48
gcacaatgac aatcacatac a                                           21

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
taggtcccag aatttcattg                                             20

<210> SEQ ID NO 50
<211> LENGTH: 17
<212> TYPE: DNA
<213> ORGANISM: Artificial Sequence
<220> FEATURE:
<223> OTHER INFORMATION: Synthetic

<400> SEQUENCE: 50
caccaaccag cacaaaa                                                17

<210> SEQ ID NO 51
<211> LENGTH: 21
<212> TYPE: DNA
<213> ORGANISM: Artificial Sequence
<220> FEATURE:
<223> OTHER INFORMATION: Synthetic

<400> SEQUENCE: 51
gcgccttctt ctgctaaatc a                                           21

<210> SEQ ID NO 52
<211> LENGTH: 26
<212> TYPE: DNA
<213> ORGANISM: Artificial Sequence
<220> FEATURE:
<223> OTHER INFORMATION: Synthetic

<400> SEQUENCE: 52
cccattcaat tgagatccaa aattac                                      26

<210> SEQ ID NO 53
<211> LENGTH: 26
<212> TYPE: DNA
<213> ORGANISM: Artificial Sequence
<220> FEATURE:
<223> OTHER INFORMATION: Synthetic
```

```
<400> SEQUENCE: 53
gcggcacaag aacagaggaa actatt                                          26

<210> SEQ ID NO 54
<211> LENGTH: 31
<212> TYPE: DNA
<213> ORGANISM: Artificial Sequence
<220> FEATURE:
<223> OTHER INFORMATION: Synthetic

<400> SEQUENCE: 54
gcggacatgg tacatctata ttacgagtat t                                    31

<210> SEQ ID NO 55
<211> LENGTH: 31
<212> TYPE: DNA
<213> ORGANISM: Artificial Sequence
<220> FEATURE:
<223> OTHER INFORMATION: Synthetic

<400> SEQUENCE: 55
gcgtaagagc atctccaaac catcaaactc a                                    31

<210> SEQ ID NO 56
<211> LENGTH: 31
<212> TYPE: DNA
<213> ORGANISM: Artificial Sequence
<220> FEATURE:
<223> OTHER INFORMATION: Synthetic

<400> SEQUENCE: 56
gcgatttatt acatttaaca attgttattt a                                    31

<210> SEQ ID NO 57
<211> LENGTH: 23
<212> TYPE: DNA
<213> ORGANISM: Artificial Sequence
<220> FEATURE:
<223> OTHER INFORMATION: Synthetic

<400> SEQUENCE: 57
aaaataacta aaatgtcttc tca                                             23

<210> SEQ ID NO 58
<211> LENGTH: 23
<212> TYPE: DNA
<213> ORGANISM: Artificial Sequence
<220> FEATURE:
<223> OTHER INFORMATION: Synthetic

<400> SEQUENCE: 58
ttggtcagat tattataaga ttg                                             23

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
gcgtgactac gggaagttgg aac                                             23
```

<210> SEQ ID NO 60
<211> LENGTH: 23
<212> TYPE: DNA
<213> ORGANISM: Artificial Sequence
<220> FEATURE:
<223> OTHER INFORMATION: Synthetic

<400> SEQUENCE: 60
gcgttggcgg taagagcact ata                                          23

<210> SEQ ID NO 61
<211> LENGTH: 27
<212> TYPE: DNA
<213> ORGANISM: Artificial Sequence
<220> FEATURE:
<223> OTHER INFORMATION: Synthetic

<400> SEQUENCE: 61
gcgacatatt gcattaaaaa catactt                                      27

<210> SEQ ID NO 62
<211> LENGTH: 29
<212> TYPE: DNA
<213> ORGANISM: Artificial Sequence
<220> FEATURE:
<223> OTHER INFORMATION: Synthetic

<400> SEQUENCE: 62
gcggactaat tctattttac accaacaac                                    29

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
gcgtattcct agtcacatgc tatttca                                      27

<210> SEQ ID NO 64
<211> LENGTH: 27
<212> TYPE: DNA
<213> ORGANISM: Artificial Sequence
<220> FEATURE:
<223> OTHER INFORMATION: Synthetic

<400> SEQUENCE: 64
gcgtcataat aatgcctaga acataaa                                      27

<210> SEQ ID NO 65
<211> LENGTH: 16
<212> TYPE: DNA
<213> ORGANISM: Artificial Sequence
<220> FEATURE:
<223> OTHER INFORMATION: Synthetic

<400> SEQUENCE: 65
ccctgtgttt ccctct                                                  16

<210> SEQ ID NO 66
<211> LENGTH: 22
<212> TYPE: DNA
<213> ORGANISM: Artificial Sequence
<220> FEATURE:
<223> OTHER INFORMATION: Synthetic

```
<400> SEQUENCE: 66
gaaaagtttt atgttctgag tg                                          22

<210> SEQ ID NO 67
<211> LENGTH: 18
<212> TYPE: DNA
<213> ORGANISM: Artificial Sequence
<220> FEATURE:
<223> OTHER INFORMATION: Synthetic

<400> SEQUENCE: 67
gcgtgagcat ttttgttt                                               18

<210> SEQ ID NO 68
<211> LENGTH: 18
<212> TYPE: DNA
<213> ORGANISM: Artificial Sequence
<220> FEATURE:
<223> OTHER INFORMATION: Synthetic

<400> SEQUENCE: 68
tgacgggttt aatagcat                                               18

<210> SEQ ID NO 69
<211> LENGTH: 18
<212> TYPE: DNA
<213> ORGANISM: Artificial Sequence
<220> FEATURE:
<223> OTHER INFORMATION: Synthetic

<400> SEQUENCE: 69
tcccttcgtc caccaaat                                               18

<210> SEQ ID NO 70
<211> LENGTH: 17
<212> TYPE: DNA
<213> ORGANISM: Artificial Sequence
<220> FEATURE:
<223> OTHER INFORMATION: Synthetic

<400> SEQUENCE: 70
ccgtcgattc cgtacaa                                                17

<210> SEQ ID NO 71
<211> LENGTH: 25
<212> TYPE: DNA
<213> ORGANISM: Artificial Sequence
<220> FEATURE:
<223> OTHER INFORMATION: Synthetic

<400> SEQUENCE: 71
gcgcattaag gcataaaaaa ggata                                       25

<210> SEQ ID NO 72
<211> LENGTH: 21
<212> TYPE: DNA
<213> ORGANISM: Artificial Sequence
<220> FEATURE:
<223> OTHER INFORMATION: Synthetic

<400> SEQUENCE: 72
gcacaatgac aatcacatac a                                           21
```

<210> SEQ ID NO 73
<211> LENGTH: 28
<212> TYPE: DNA
<213> ORGANISM: Artificial Sequence
<220> FEATURE:
<223> OTHER INFORMATION: Synthetic

<400> SEQUENCE: 73
gcgagtaacg gtcttctaac aaggaaag                                    28

<210> SEQ ID NO 74
<211> LENGTH: 25
<212> TYPE: DNA
<213> ORGANISM: Artificial Sequence
<220> FEATURE:
<223> OTHER INFORMATION: Synthetic

<400> SEQUENCE: 74
gcgtgccctt actctcaaaa aaaaa                                       25

<210> SEQ ID NO 75
<211> LENGTH: 30
<212> TYPE: DNA
<213> ORGANISM: Artificial Sequence
<220> FEATURE:
<223> OTHER INFORMATION: Synthetic

<400> SEQUENCE: 75
gcggcatgtc atggtatacg taactttaga                                  30

<210> SEQ ID NO 76
<211> LENGTH: 27
<212> TYPE: DNA
<213> ORGANISM: Artificial Sequence
<220> FEATURE:
<223> OTHER INFORMATION: Synthetic

<400> SEQUENCE: 76
gcgcaactga agcaagaaaa gaaacct                                     27

<210> SEQ ID NO 77
<211> LENGTH: 24
<212> TYPE: DNA
<213> ORGANISM: Artificial Sequence
<220> FEATURE:
<223> OTHER INFORMATION: Synthetic

<400> SEQUENCE: 77
gcgtagcaac aaagcaatct acag                                        24

<210> SEQ ID NO 78
<211> LENGTH: 29
<212> TYPE: DNA
<213> ORGANISM: Artificial Sequence
<220> FEATURE:
<223> OTHER INFORMATION: Synthetic

<400> SEQUENCE: 78
gcgtcccatt ttattccaca ctatgtaat                                   29

<210> SEQ ID NO 79
<211> LENGTH: 31
<212> TYPE: DNA
<213> ORGANISM: Artificial Sequence
<220> FEATURE:
<223> OTHER INFORMATION: Synthetic

<400> SEQUENCE: 79
ggcggtggat atgaaacttc ataactaca a                                31

<210> SEQ ID NO 80
<211> LENGTH: 33
<212> TYPE: DNA
<213> ORGANISM: Artificial Sequence
<220> FEATURE:
<223> OTHER INFORMATION: Synthetic

<400> SEQUENCE: 80
ggcgggcttc aaataattac tataaaacta cgg                             33

<210> SEQ ID NO 81
<211> LENGTH: 26
<212> TYPE: DNA
<213> ORGANISM: Artificial Sequence
<220> FEATURE:
<223> OTHER INFORMATION: Synthetic

<400> SEQUENCE: 81
gcggcacaag aacagaggaa actatt                                     26

<210> SEQ ID NO 82
<211> LENGTH: 31
<212> TYPE: DNA
<213> ORGANISM: Artificial Sequence
<220> FEATURE:
<223> OTHER INFORMATION: Synthetic

<400> SEQUENCE: 82
gcggacatgg tacatctata ttacgagtat t                               31

<210> SEQ ID NO 83
<211> LENGTH: 22
<212> TYPE: DNA
<213> ORGANISM: Artificial Sequence
<220> FEATURE:
<223> OTHER INFORMATION: Synthetic

<400> SEQUENCE: 83
ctggcgaatc aagctttgta ac                                         22

<210> SEQ ID NO 84
<211> LENGTH: 22
<212> TYPE: DNA
<213> ORGANISM: Artificial Sequence
<220> FEATURE:
<223> OTHER INFORMATION: Synthetic

<400> SEQUENCE: 84
ccgtgattgc gaagaggata tt                                         22

<210> SEQ ID NO 85
<211> LENGTH: 18
<212> TYPE: DNA
<213> ORGANISM: Artificial Sequence
<220> FEATURE:
<223> OTHER INFORMATION: Synthetic

<400> SEQUENCE: 85
ggctaacccg ctctatgt                                              18

```
<210> SEQ ID NO 86
<211> LENGTH: 19
<212> TYPE: DNA
<213> ORGANISM: Artificial Sequence
<220> FEATURE:
<223> OTHER INFORMATION: Synthetic

<400> SEQUENCE: 86
gggccatgca cctgctact                                                  19

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
caagctcaag cctcacacat                                                 20

<210> SEQ ID NO 88
<211> LENGTH: 22
<212> TYPE: DNA
<213> ORGANISM: Artificial Sequence
<220> FEATURE:
<223> OTHER INFORMATION: Synthetic

<400> SEQUENCE: 88
tgaccagagt ccaaagttca tc                                              22

<210> SEQ ID NO 89
<211> LENGTH: 26
<212> TYPE: DNA
<213> ORGANISM: Artificial Sequence
<220> FEATURE:
<223> OTHER INFORMATION: Synthetic

<400> SEQUENCE: 89
ttggatctca tattcaaact ttcaag                                          26

<210> SEQ ID NO 90
<211> LENGTH: 26
<212> TYPE: DNA
<213> ORGANISM: Artificial Sequence
<220> FEATURE:
<223> OTHER INFORMATION: Synthetic

<400> SEQUENCE: 90
ctgcaaattt gatgcacatg tgtcta                                          26
```